US006830748B1

(12) United States Patent
Jin et al.

(10) Patent No.: US 6,830,748 B1
(45) Date of Patent: Dec. 14, 2004

(54) RECOMBINANT RSV VIRUS EXPRESSION SYSTEMS AND VACCINES

(75) Inventors: Hong Jin, Cupertino, CA (US); Roderick Tang, San Carlos, CA (US); Shengqiang Li, Palo Alto, CA (US); Martin Bryant, Carlisle, MA (US)

(73) Assignee: MedImmune Vaccines, Inc., Mountain View, CA (US)

( * ) Notice: Subject to any disclaimer, the term of this patent is extended or adjusted under 35 U.S.C. 154(b) by 0 days.

(21) Appl. No.: 09/368,076

(22) Filed: Aug. 3, 1999

Related U.S. Application Data

(63) Continuation-in-part of application No. 09/161,122, filed on Sep. 25, 1998, now abandoned.
(60) Provisional application No. 60/089,207, filed on Jun. 12, 1998, provisional application No. 60/084,133, filed on May 1, 1998, and provisional application No. 60/060,153, filed on Sep. 26, 1997.

(51) Int. Cl.[7] .............................. C12N 7/00; C12N 7/04; A61K 39/12; A61K 39/155; C07H 21/02
(52) U.S. Cl. .................. 424/93.2; 424/93.1; 424/204.1; 424/205.1; 424/211.1; 435/235.1; 435/236; 435/239; 536/23.7; 536/23.72
(58) Field of Search .......................... 424/184.1, 199.1, 424/204.1, 205.1, 211.1, 93.1, 93.2, 936; 435/5, 69.1, 69.3, 235.1, 236, 237, 239, 320.1, 440, 471, 238, 172.1, 328.1, 325; 536/23.1, 23.7, 23.72

(56) References Cited

U.S. PATENT DOCUMENTS

| | | | |
|---|---|---|---|
| 5,166,057 A | 11/1992 | Palese et al. .............. | 435/69.1 |
| 5,843,451 A | 12/1998 | Compans et al. | |
| 5,993,824 A * | 11/1999 | Murphy et al. .......... | 424/211.1 |
| 6,033,886 A | 3/2000 | Conzelmann | |
| 6,060,308 A | 5/2000 | Parrington | |
| 6,168,943 B1 | 1/2001 | Rose | |
| 6,376,171 B1 * | 4/2002 | Hardy et al. ................... | 435/5 |

FOREIGN PATENT DOCUMENTS

| | | |
|---|---|---|
| EP | 0 440 219 | 8/1991 |
| WO | WO 91/03552 | 3/1991 |
| WO | WO 93/06218 | 4/1993 |
| WO | WO 95/08634 | 3/1995 |
| WO | WO 96/10632 | 1/1996 |
| WO | WO 96/40945 | 12/1996 |
| WO | WO97/12032 | 4/1997 |
| WO | WO 97/12032 * | 4/1997 |
| WO | WO 98/02179 | 1/1998 |
| WO | WO 98/02530 * | 1/1998 |
| WO | WO 98/50405 | 11/1998 |
| WO | WO 98/53078 | 11/1998 |
| WO | WO 99/57284 | 11/1999 |
| WO | WO 99/63064 | 12/1999 |
| WO | WO 00/18929 | 4/2000 |
| WO | WO 00/53786 | 9/2000 |

OTHER PUBLICATIONS

Tang et al., Journal of Virology, vol. 76 No 23, pp. 11328–11335 (Dec. 2001).*

Bukreyev et al. Recovery of infectious respiratory syncytial virus expressing an additional, foreign gene. J Virol. 1996 Oct.;70(10):6634–41.
Firestone et al. Nucleotide sequence analysis of the respiratory syncytial virus subgroup A cold–passaged (cp) temperature sensitive (ts) cpts–248/404 live attenuated virus vaccine candidate. Virology. Nov. 15, 1996;225(2):419–22.
Murphy et al. An update on approaches to the development of respiratory syncytial virus (RSV) and parainfluenza virus type 3 (PIV3) vaccines. Virus Res. Apr. 1994;32(1):13–36. Review.
Tolley et al. Identification of mutations contributing to the reduced virulence of a modified strain of respiratory syncytial virus. Vaccine. Dec. 1996;14(17–18):1637–46.
Whitehead et al. Replacement of the F and G proteins of respiratory syncytial virus (RSV) subgroup A with those of subgroup B generates chimeric live attenuated RSV subgroup B vaccine candidates. J Virol. Dec. 1999; 73(12):9773–80.
Lodish et al., Molecular Cell Biology, Third Edition, Scientific American Books, 1995.
Frillingos et al., "Cys–Scanning Mutageneis: A novel Approach to Structure–Function Reltionships in polytopic membrane proteins, FASEB," Journal, 12:1281–1299 (1998).
Collins et al., "Support Plasmids and Suppoet Proteins Required for Recovery of Recombinant REspiratory Syncytial Virus," Virology, vol. 259, pp. 251–255 (1999).
Hardy et al., The Cys3–His1 Motif of te REspiratory Syncytial Virus M2–1 Protein is Essential for Protein Function, Journal of Virology, vol. 74, 5880–5885 (2000).
Atreya, P. L. et et al., 1998, J. Virol. 72:1452–1461.
Baron & Barrett, 1997, J. virol. 71:1265–1271.
Beeler and Coelingh, 1988, J. Virol. 63:2941–2950.
Brown et al.,1967, J. Virol. 1:368–373.
Buchholz, U. J.et al.,1999, J Virol 73(1): 251–259.
Bukreyev, A.et al.,1997, J Virol 71(12):8973–82.
Castrucci et al., 1995, J. Virol. 69(5):2725–2728.
Chin et et al.,1969, Am. J. Epidemiol. 89:449–463.
Coates, H.V. et al.,1965, AM. J. Epid. 83:299–313.
Collins et al., 1984. J. Virol. 49:572–578.
Collins et al.,1990, Vaccine 8:164–168.
Collins, 1991, The paramyxoviruses pp. 103–162. D.W. Kingsbury (ed.) Plenum Press New York.

(List continued on next page.)

Primary Examiner—James Housel
Assistant Examiner—Zachariah Lucas
(74) Attorney, Agent, or Firm—Jones Day

(57) ABSTRACT

The present invention relates to genetically engineered recombinant respiratory syncytial viruses and viral vectors which contain deletions of various viral accessory gene(s) either singly or in combination. In accordance with the present invention, the recombinant respiratory syncytial viral vectors and viruses are engineered to contain complete deletions of the M2-2, NS1, NS2, or SH viral accessory genes or various combinations thereof. In addition, the present invention relates to the attenuation of respiratory syncytial virus by mutagenisis of the M2-1 gene.

8 Claims, 25 Drawing Sheets

OTHER PUBLICATIONS

Figure 1:
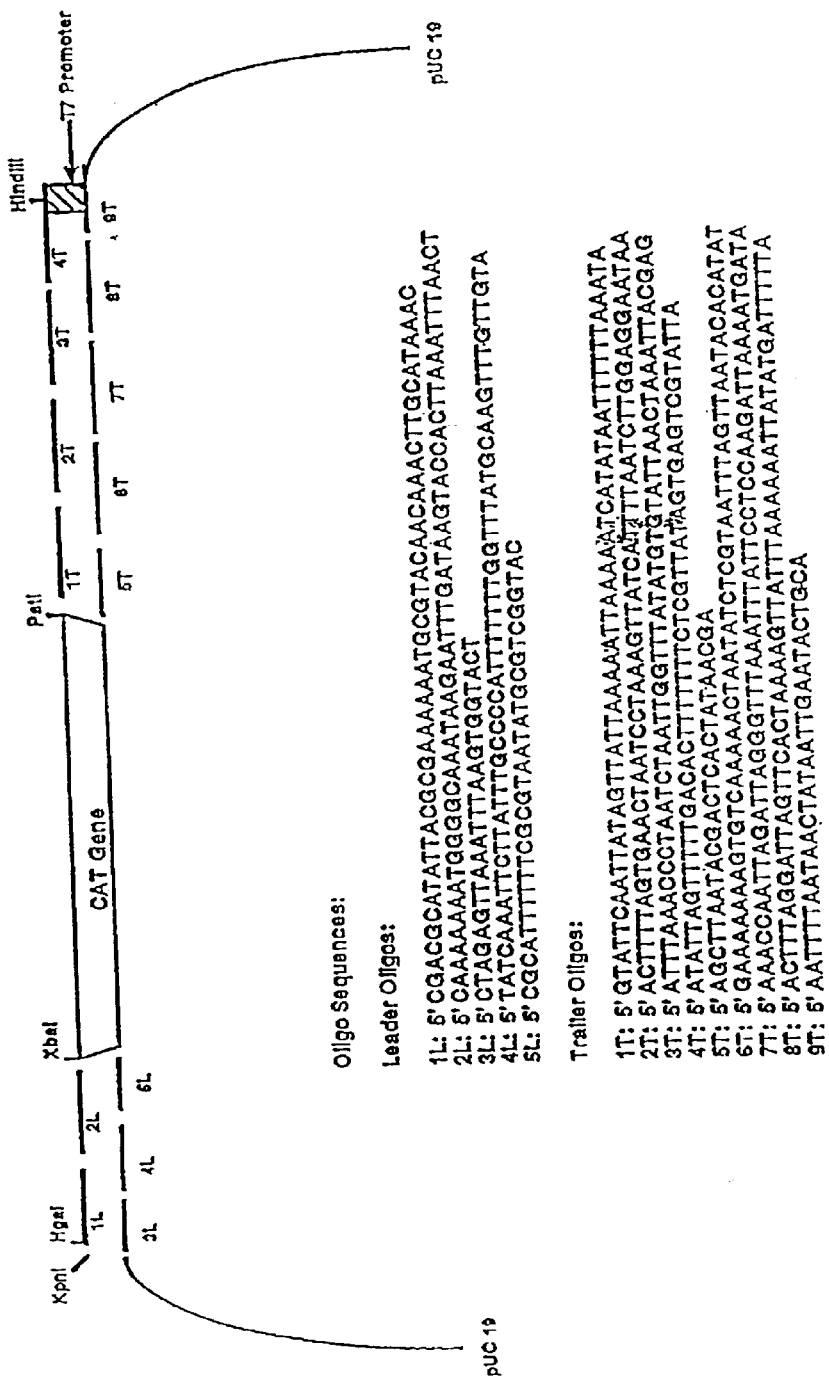

Collins et al., 1991, Proc. Natl. Acad. Sci. USA 88:9663–9667.
Collins et al., 1993, Virology 195:252–256.
Collins et al., 1995. Proc. Natl. Acad. Sci. USA 92:11563–11567.
Collins, P.L. et al.,1996, pp 1313–1351 of vol. 1, Fields Virology, et al.,Eds. 3rd ed., Raven Press.
Collins, P. L. et al.,1996, Proc. Natl. Acad. Sci. U S A 93, 81–85.
Crowe et al.,1994, Vaccine 12:691–699.
Crowe et al.,1995, Vaccine 13(4):415–421.
Current Protocols in Molecular Biology, vol. 1: Chapter 9.6.2.
Durbin et al.,1997, Virology 235:323–332.
Elango, N. et al.,1989, J Virol 63(3):1413–5.
Enami et al., 1990, Proc. Natl. Acad. Sci. USA 92:11563–11567.
Garcia et al., 1993, Virology 195:243–247.
Gharpure et al.,1969, J. Virol. 3: 414–421.
Gorman, et al.,(1982) Mol. Cell. Biol. 2:1044–1051.
Grosfeld, H. et al.,1995, J. Virol. 69:5677–5686.
Hardy, R. W. et al., 1998, J. Virol. 72, 520–526.
He et al.,1997, Virology 237:249–260.
Hiebert, S. W. et al.,1985, J Virol 55(3):744–51.
Hodes et al.,1974, Proc. Soc. Exp. Biol. Med. 145:1158–1164.
Hoffman & Banerjee, 1997, J. Virol. 71:4272–4277.
International Search Report PCT/US98/20230.
Jin, H. et al., 1997, Embo J. 16(6):1236–47.
Jin, H. et al., 1998, Virology 251:206–214.
Kapikian et al.,1969, Am. J. Epidemiol. 89:405–421.
Karron, R. A. et al.,1997, J. Infect. Dis. 176:1428–1436.
Kato et al., 1996, Genes to Cells 1:569–579.
Kim et al., 1973, Pediatrics 52:56–63.
Kingsbury et al.,1987, Virology 156:396–403.
Krystal et al.,1986, Proc. Natl. Acad. Sci. USA 83:2709–2713.
Kunkel, 1985, Proc. Natl. Acad. Sci. U.S.A. 82:488–492.
Lawson et al.,1995, Proc. Natl. Acad. Sci USA 92:4477–4481.
Luytjes et al., 1989, Cell 59:1107–1113.
McIntosh and Chanock. 1990 "Respiratory Syncytial Virus" 2nd ed. Virology (D. M. Knipe et al., Ed.) Raven Press. Ltd.. N.Y. 1045–1072.
Mink et al.,1991, Virology 185:615–624.
Nayak et al.,1983, Genetics of Influenza Viruses, P. Palese and D. W. Kingsbury, eds., Springer–Verlag, Vienna, pp. 255–279.
Olmsted et al., 1986, Proc. Natl. Acad. Sci. 83:7462–7466.
Park et al., 1991, Proc. Natl. Acad. Sci. USA 88:5537–5541.
Radecke et al., 1995, EMBO J. 14:5773–5784.
Sambrook et al.,Molecular Cloning—A Laboratory Manual, Cold Spring Harbor laboratory Press, Cold Spring Harbor, NY, 1989.
Schnell et al., 1994, EMBO J. 13:4195–4203.
Teng, M. N., et al., 1999, J Virol 73(1):466–473.
Wang et al., 1989, Proc. Natl. Acad. Sci. 88:9717–9721.
Worthington et et al., 1996, Proc. Natl. Acad. Sci. 93:13754–13759.
Wright et al., 1976, J. Pediatrics 88:931–936.
Yu et al., 1995 J. Virol. 69:2412–2419.
Howorka and Bayley, 1998, Improved protocol for high–throughput cysteine scanning mutagenesis. BioTechniques. 25(5):764–6, 768, 770 passim.
Teng and Collins, 1998, Identification of the respiratory syncytial virus proteins required for formation and passage of helper–dependent infectious particles. J. Virol. 72(7):5707–16.
Dudas RA, Karron RA. Respiratory syncytial virus vaccines. Clin Microbiol Rev. 1998 Jul;11(3):430–439.
Crowe et al. A further attenuated derivative of a cold–passaged temperature–sensitive mutant of human respiratory syncytial virus retains immunogenicity and protective efficacy against wild–type challenge in seronegative chimpanzees. Vaccine. Jul. 1994; 12(9):783–790.
Prince et al. Efficacy and safety studies of a recombinant chimeric respiratory syncytial virus FG glycoprotein vaccine in cotton rats. J Virol. Nov. 2000;74(22):10287–10292.
Tang et al. Effects of human metapneumovirus and respiratory syncytial virus antigen insertion in two 3' proximal genome positions of bovine/human parainfluenza virus type 3 on virus replication and immunogenicity. J Virol. Oct. 2003;77(20):10819–10828.

* cited by examiner

A. RSVB-GF

ATCAGGATCCACAATAACATTGGGGCAAATGCAACC ―

FIGS. 6A-B

FIG. 9

```
MDPIINGNSANVILT DSYLKGVISFSECNA LGSYIFNGPYLKNDY TNLISRQMPLIEHMN LKKLNITQSLISKYH                75
KGEIKLEEPTYFQSL LMTYKSMTSSEQIAT TNLLKKIIRRAIEIS DVKVYAILNKLGLAE KDKIKSNNGQDEDNS               150
VITTIIKDDILSAVK DNQSHLKADRNHSTK QKDTIKTLLKKLMC  SMQHPPSWLIHWFNL YTKLNNILTQYRSNE               225
VKNHGFTLIDNQTLS GFQFTLNQYGCIVYH KELARITVTTNQFL  TWKDISLSRINVCLI  TWISNCIANTLNKSLG              300
LRCGFNNVLTQLFL  YGDCILKLFHNEGFY IIKEVEGFIMSLIIN ITEEDQFEKKFYNSM  LNNITDAANKAQKNL              375
LSRVCHTLLDKTVSD NIINGRWIIILSKEL KLIKLAGDNNLANLS ELYFLFRIFGHPMVD  ERQAMDAVKINCNET              450
KFYLLSSLSMLRGAF TYRIIKGFVNNYNRW PTLRNAIVLPLRMLT YYKLNTYPSLLELTE  PDLIVLSGLRFYREF              525
RLPKKVDLEMIINDK AISPPKNLIWTSFPR NYMPSHIQNYIEHEK LKFSESDKSRKVLEY  YLRDNKFNECDLYNC              600
VVNQSYLNNENHVYS LIGKERELSVGRMFA MQPGMFRQVQILAEK MIAENILQFFPESLT  RYGDLELQKILELKA              675
GISNKSNRYMDNYNN YISKCSIITDLSKFN QAFRYETSCICSDVL DELHGVQSLFSWLHL  TIPHVTICTYRHAP               750
PYIGDHIVDLNNVDE QSGLYRYHMGGIEGW CQKLWTIERAISLLDL ISLKGKFSITALING  DNQSIDISKPIRLME              825
GQTHAQADYLLALNS LKLIYKEYAGIGHKL KGTETYISRDMQFMS KTIQHNGVYYPASIK  KVLRVGPWINTILDD              900
FKVSLESIGSLTQEL EYRGESLLCSLIIFRN VMLXNQIALQLKNHA LCNNKLYLDILKVLK  HLKTFFNLDNIDIAL              975
TLXMNLPMLFGGGDP NLLYRSFYRRTPDFL TEAIVHSVFILSYYT NHDLKDKLQDLSDDR  LNKFLTCIITPDKNP              1050
NAEFVTLMRDPQALG SERQAKITSEINRLA VTEVLSTAPNKIFSK SAQHYTTTEIDLNDI  MQNIEPTYPHGLRVV              1125
YESLPFYKAEKIVNL ISGTKSTTNTLEKTS AIDLIDIDRATEMMR KNITLLIRILPLDCN  RDKREILSMENLSIT              1200
ELSKYVFERSWSLSN TVGVTSPSIMYTMDI KYTTSTISSGIIIEK YNVNSLTRGERGPTK  FWVGSSTQEKRTMPV              1275
YNRQVLNKKQRDQID LLAKLDWYASIDNK  DEFMEELSIGTLGLT YEKAKKLFPQYLSVN  YLHRLITVSSRPCEFP             1350
ASIPAYRITNYHFDT SPINRILHEKGDED  IDIVFQNCISFGLSL MSVVBQFTNVCPNRI  ILIPKLNEIHLMKPP              1425
IFTGDVDIHKLKQVI QKQHMFLPDKISLTQ YVELFLSNKTLKSGS HVNSNLILAHKISDY  FHNTYILSTNLAGHW              1500
LLIIQLMKDSKGIFE KPWGEGYITDHMFTN LKVFFNAYKTYILCF HKGYGKAKLECDMNT  SDLLCVLELIDSSYW              1575
KSMSKVFLEQKVIKY ILSQDASLHRVKGCH SFKLMFLKRLNVAEF TVCPWVVNIDYHPTH  MKAILTYIDLVRMGL              1650
INIDRIHIKNHLKFN DEFYTSNLFYINVNF SDNTHLLTLKHIRIAN SELENNYNKLYHPTP BTLENILANPIKSND             1725
KRTLNDYICIGKNVDS IMLPLLSNKLLIKSS AMIRTNYSKQDLYNL FPMVVIDRIIDHSGN  TAKSNQLYTTTSHQI              1800
SLVFNSTSLYCMLPW HHINRRTNFVFSSTGC KISIEYLKDLKTKD  PNCIAFIGEGAGNLL  LRTVBLHPDIRYIY               1875
RSLKDQNDHSLPIEF LRLYANGHINIDYGEN LTIPATDATNNIHWS YLHIKFAEPISLFVC DAELSVTVNWSKIII              1950
EWSKGVRKCKYCSSV NKCMLIVKVHAQDDI DFKLDNITILKTVC  LGSKLKGSEVYLVLT  IGPANIFPVFNVVQN              2025
AKLILSRTKNFIMFK KADLKESIDANIKSLI PFLCYPITKKGINTA LSKLKSVSGDILSY  SLAGRNEVFSNKLIN              2100
HKHMNILKWFNHVLN FRSTELNYNFHLYMVE STYPYLSELINSLTT NELKKLIKITGSLLY  NFHNE                       2165
```

☐ Charged Clusters (Amino Acids that are underlined were changed to alanines)
☐ Mutations in cpts-248/404
■ Mutation in cpts530

FIG. 10

```
MDPIINGNSANVLT DSYLKGVISFSECNA LGSYIFNGPYLKNDY TNLISRQNPLIEHMN LKKLNITQSLISKYH      75
KGEIKLEEPTYFQSL LMTYKSMTSSEQIAT TNLLKKLIRRAIEIS DVKVYAILNKLGLKE KDKIKSNNGQDEDNS    150
VITTIKDDILSAVK  DNQSELKADKNHSTK QKDTIKTTLIKKLMC SMQHPPSWLIHWFNL YTKLNNILTQYRSNE   225
VKNHGFTLIDNQTLS GFQFILNQXGCIVYH KELKRITVTTYNQFL TWKDISLSRLNVCLI TWISNCINTLNKSLG   300
LRCGFNNVLLQLFL  YGDCILKLFHNEGFY IIKEVEGFIMSLIIN ITEEDQFRKRFYNSM LNNITDAANKAQKNL   375
LSRVCHTLLDKTVSD NIINGRWILLSKFL  KLIKLAGDNNINNLS ELYFLFRIFGHPMVD ERQAMDAVKINCNET   450
KFYILSSLSMLRGAF IYRIIKGFVNNYNRW PTLRNAIVLPLRWLT YXKLANTYPSLLELTE RDLIVLSGLRFYREF   525
RLPKKVDLEMIINDK AISPPKNLIWTSFPR NYMPSHIQNYIEHEK LKFSESDKSRRVLEY YLRDNKFNECDLYNC    600
VVNQSYINNENHVVS LTGKERELSVGRMFA MQPGMFRQVQILAEK MIAENLLQFFPESLT RYGDLELQKILELKA   675
GISNKSNRYNDNYNN YISKCSIITDLSKFN QAFRYETSCICSDVL DELHGVQSLFSWLHL TIPHVTIICTYRHAP   750
PYIGDHIVDLNNVDE QSGLYRXHMGGIEGM CQXLWTIEAISLLDL ISLKGKFSITALING DNQSIDISKPIRLME    825
GQTHAQADYLLALNS LKILLYKEYAGIGHKL KGTETYIISRDMQFMS KTIQHNGVYYPASIK KVLRVGPWINTILDD    900
FKVSLESIGSLIQEL EYRGESLLQSLIFRN VWLXNQIALQLKNHA LCNNKLYLDILKVLK HLKTFFNLDNIDTAL   975
TLYMNLPMLFGGGDP NLLXRSFYRRTPDFL TEAIVHSVFILSYYT NHDLKDKLQDLSDDR LNKFLTCIITFDKNP   1050
NAEFVTLMRDPQALG SERQAKITSEINRLA VTEVLSTAPNKIFSK SAQHYTTEIDLNDI MQNIEPTYPHGLRVV   1125
YESLPFYKDEKIVNL ISGTKSITNIIEKTS AIDLMDIDRATEMMR KNITLLIRILPLDQN RDKREILSMENLSIT   1200
ELSKYVRERSWSLSN IVGVTSPSIMYIMDI KYTTSTISSGIIIEK DEFMEELSIGTLGLT YEKAKKLFPQYLSVN   PWGSSTQEKKTMPV  1275
YNRQVLTKKQRDQID LLAKLDWVXASIDNK DEFMEELSIGTLGLT YEKAKKLFPQYLSVN YLHRLTVSSRPQEFP   1350
ASIPAYRYTNYHFDT SPINRILTEKYGDED IDIVFQNCISFGLSL MSVVEQFTNVCPNRI ILIPKLNEIHLMKPP   1425
IFTGDVDIHKLKQVI QKQHMFLPDKISLTQ YVELFLSNKTIKSGS HVNSNLILAHKISDY FHNTYILSTNLAGHW   1500
ILIQLMDSKGIFE   KDWGEGYITDHMFIN LKVFFNAYKTYLLCF HKGYGKAKLECDMNT SDLLCVLELIDSSYW   1575
KSMSKVFLEQKVIKY ILSQDASLHRVKGCH SFKLWFLKRLNVAEF TVCPWVVNIDYHPTH MKAILTYIDLVRMGL   1650
INIDRIHIKNKHKFN DEFYTSMLFYINANF SDNTHLLTKHIRIAN SELENNYNKLYHPTP ETLENILANPIKSND   1725
KKTLNDYCIGKNVDS IMLPLLSNKKLIKSS AMIRTNYSKQDLYNL  FPMVVIDRIIDHSGN TAKSNQLYTTSHQI   1800
SLVHNSTSLYCMLPW HHIMRFNFVFSSTGC KISIEYILKDLKIKD PNCIAFIGEGAGNLL LRMVVELHPDIRYIY   1875
RSLKDCNDHSLPIEF LRLYNGHINLDYGEN LTIPATDATNNIEWS YLHIKFAEPISLFVC DAELSVTVNWSKIII   1950
EWSKHVRKCKYCSSV NKCMLIVKYHAQDDI DFKLDNITILKTYVC LGSKLKGSEVLVLT  IGPANIFPVFNVVQN   2025
AKLILSRIKNFIMPK KADKESIDANIKSLI PFLCYPITKKGINTA LSKLKSVVSGDILSY SIAGRNEVFSNKLLIN  2100
HKHMNILKWFNHVLN FRSTELNYNHLYMVE STYPYLSELLNSLTT NELKKLIKITGSLLY NFHNE             2165 c   Cysteine residues
c̲   Cysteine residues that were changed to valine or aspartic acid
ć   Cysteine residue deleted
```

FIG. 11

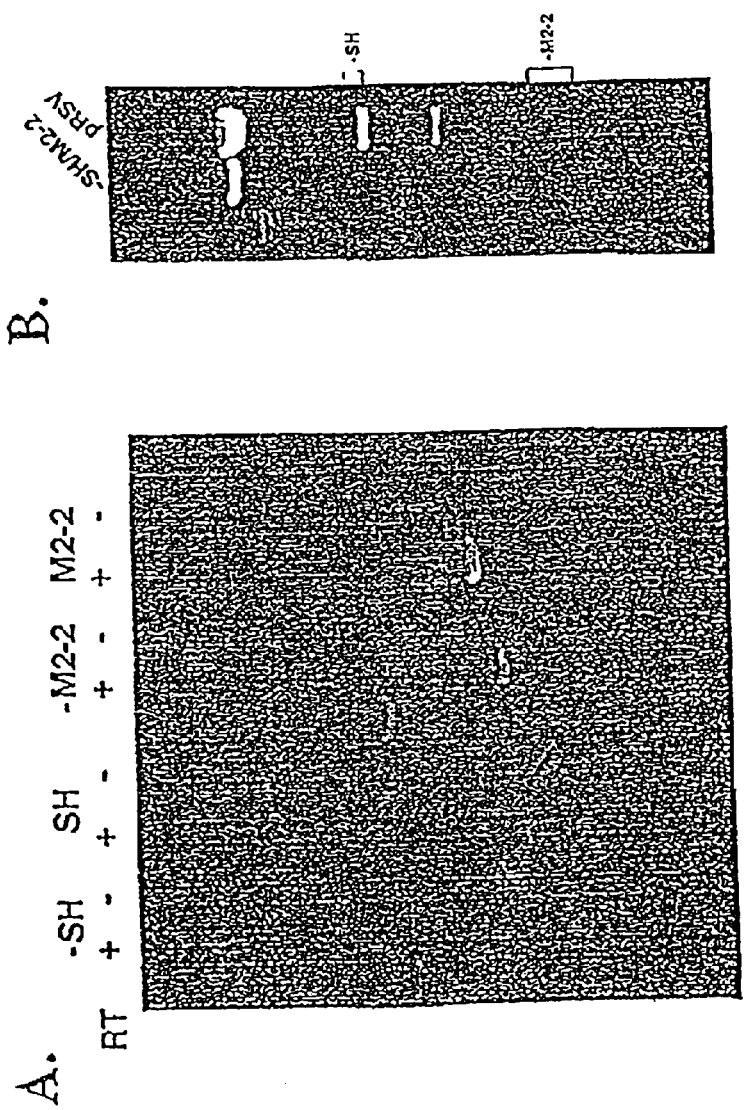
FIGS. 12A-B

A.
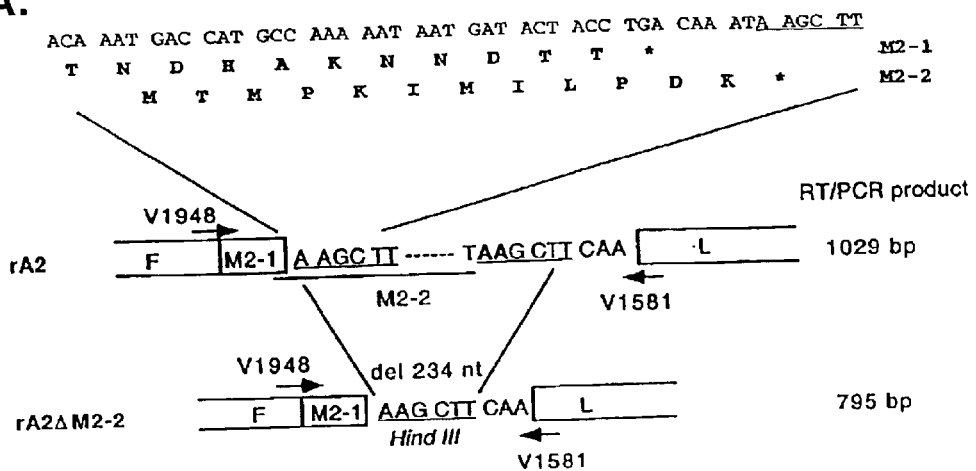
B.
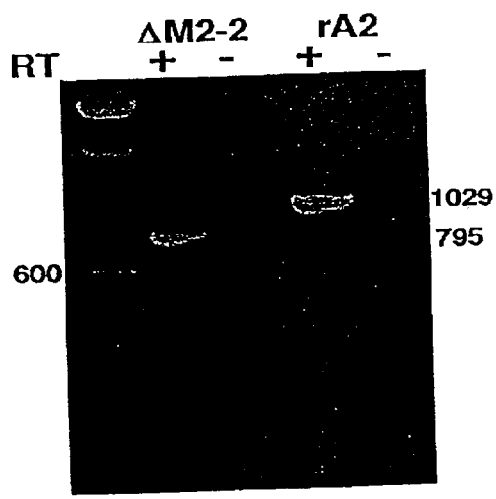
FIG. 13

SEQUENCE LISTING

```
<160> NUMBER OF SEQ ID NOS: 56

<210> SEQ ID NO 1
<211> LENGTH: 46
<212> TYPE: DNA
<213> ORGANISM: Artificial Sequence
<220> FEATURE:
<223> OTHER INFORMATION: Oligonucleotide

<400> SEQUENCE: 1
cgacgcatat tacgcgaaaa aatgcgtaca acaaacttgc ataaac               46

<210> SEQ ID NO 2
<211> LENGTH: 50
<212> TYPE: DNA
<213> ORGANISM: Artificial Sequence
<220> FEATURE:
<223> OTHER INFORMATION: Oligonucleotide

<400> SEQUENCE: 2
caaaaaaatg gggcaaataa gaatttgata agtaccactt aaatttaact           50

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
ctagagttaa atttaagtgg tact                                       24
```

```
<210> SEQ ID NO 4
<211> LENGTH: 50
<212> TYPE: DNA
<213> ORGANISM: Artificial Sequence
<220> FEATURE:
<223> OTHER INFORMATION: Oligonucleotide

<400> SEQUENCE: 4
tatcaaattc ttatttgccc cattttttttg gtttatgcaa gtttgttgta            50

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5 cgcattttttt cgcgtaatat gcgtcggtac                                   30

<210> SEQ ID NO 6
<211> LENGTH: 50
<212> TYPE: DNA
<213> ORGANISM: Artificial Sequence
<220> FEATURE:
<223> OTHER INFORMATION: Oligonucleotide

<400> SEQUENCE: 6
gtattcaatt atagttatta aaaattaaaa atcatataat tttttaaata            50

<210> SEQ ID NO 7
<211> LENGTH: 50
<212> TYPE: DNA
<213> ORGANISM: Artificial Sequence
<220> FEATURE:
<223> OTHER INFORMATION: Oligonucleotide

<400> SEQUENCE: 7 actttttagtg aactaatcct aaagttatca ttttaatctt ggaggaataa            50

<210> SEQ ID NO 8
<211> LENGTH: 50
<212> TYPE: DNA
<213> ORGANISM: Artificial Sequence
<220> FEATURE:
<223> OTHER INFORMATION: Oligonucleotide

<400> SEQUENCE: 8
atttaaaccc taatctaatt ggtttatatg tgtattaact aaattacgag             50

<210> SEQ ID NO 9
<211> LENGTH: 46
<212> TYPE: DNA
<213> ORGANISM: Artificial Sequence
<220> FEATURE:
<223> OTHER INFORMATION: Oligonucleotide

<400> SEQUENCE: 9
atattagttt ttgacactttt ttttctcgtt atagtgagtc gtatta              46

<210> SEQ ID NO 10
<211> LENGTH: 25
<212> TYPE: DNA
<213> ORGANISM: Artificial Sequence
<220> FEATURE:
```

<223> OTHER INFORMATION: Oligonucleotide

<400> SEQUENCE: 10
agcttaatac gactcactat aacga                                         25

<210> SEQ ID NO 11
<211> LENGTH: 50
<212> TYPE: DNA
<213> ORGANISM: Artificial Sequence
<220> FEATURE:
<223> OTHER INFORMATION: Oligonucleotide

<400> SEQUENCE: 11 gaaaaaagt gtcaaaaact aatatctcgt aatttagtta atacacatat              50

<210> SEQ ID NO 12
<211> LENGTH: 50
<212> TYPE: DNA
<213> ORGANISM: Artificial Sequence
<220> FEATURE:
<223> OTHER INFORMATION: Oligonucleotide

<400> SEQUENCE: 12
aaaccaatta gattagggtt taaatttatt cctccaagat taaaatgata             50

<210> SEQ ID NO 13
<211> LENGTH: 50
<212> TYPE: DNA
<213> ORGANISM: Artificial Sequence
<220> FEATURE:
<223> OTHER INFORMATION: Oligonucleotide

<400> SEQUENCE: 13
actttaggat tagttcacta aaagttattt aaaaaattat atgatttta              50

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide

<400> SEQUENCE: 14
atttttaata actataattg aatactgca                                     29

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15
gtttaacacg tggtgag                                                  17

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16 acataggc atgcacc                                                    17

```
<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
gcaaaatgga tcccatt                                                    17

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tggttggtat accagtgt                                                   18

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
taccaagagc tcgagtca                                                   18

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ggtggccggc atggtcccag c                                               21

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tttaccatat gcgctaatgt                                                 20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
acgcgaaaaa atgcgtaca                                                  19

<210> SEQ ID NO 23
<211> LENGTH: 18
<212> TYPE: DNA
<213> ORGANISM: Artificial Sequence
<220> FEATURE:
<223> OTHER INFORMATION: Primer
```

-continued

```
<400> SEQUENCE: 23
acgagaaaaa agtggcaa                                                18

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
ctcaccacgt gttaaac                                                 17

<210> SEQ ID NO 25
<211> LENGTH: 17
<212> TYPE: DNA
<213> ORGANISM: Artificial Sequence
<220> FEATURE:
<223> OTHER INFORMATION: Primer

<400> SEQUENCE: 25
ggtgcatgcc tatatgt                                                 17

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
aatgggatcc attttgtcc                                               19

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
aacactggta taccaacca                                               19

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
acattagcgc atatggtaaa                                              20

<210> SEQ ID NO 29
<211> LENGTH: 2165
<212> TYPE: PRT
<213> ORGANISM: Virus

<400> SEQUENCE: 29

Met Asp Pro Ile Ile Asn Gly Asn Ser Ala Asn Val Tyr Leu Thr Asp
  1               5                  10                  15

Ser Tyr Leu Lys Gly Val Ile Ser Phe Ser Glu Cys Asn Ala Leu Gly
             20                  25                  30

Ser Tyr Ile Phe Asn Gly Pro Tyr Leu Lys Asn Asp Tyr Thr Asn Leu
```

-continued

```
                35                  40                  45
Ile Ser Arg Gln Asn Pro Leu Ile Glu His Met Asn Leu Lys Lys Leu
 50                  55                  60

Asn Ile Thr Gln Ser Leu Ile Ser Lys Tyr His Lys Gly Glu Ile Lys
 65                  70                  75                  80

Leu Glu Glu Pro Thr Tyr Phe Gln Ser Leu Leu Met Thr Tyr Lys Ser
                 85                  90                  95

Met Thr Ser Ser Glu Gln Ile Ala Thr Thr Asn Leu Leu Lys Lys Ile
                100                 105                 110

Ile Arg Arg Ala Ile Glu Ile Ser Asp Val Lys Val Tyr Ala Ile Leu
            115                 120                 125

Asn Lys Leu Gly Leu Lys Glu Lys Asp Lys Ile Lys Ser Asn Asn Gly
130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
    195                 200                 205

Asn Leu Tyr Thr Lys Leu Asn Asn Ile Leu Thr Gln Tyr Arg Ser Asn
210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
290                 295                 300

Phe Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
        435                 440                 445

Glu Thr Lys Phe Tyr Leu Leu Ser Ser Leu Ser Met Leu Arg Gly Ala
    450                 455                 460
```

```
Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
                500                 505                 510

Leu Ile Val Leu Ser Gly Leu Arg Phe Tyr Arg Glu Phe Arg Leu Pro
                515                 520                 525

Lys Lys Val Asp Leu Glu Met Ile Ile Asn Asp Lys Ala Ile Ser Pro
                530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
                580                 585                 590

Asn Glu Cys Asp Leu Tyr Asn Cys Val Val Asn Gln Ser Tyr Leu Asn
                595                 600                 605

Asn Pro Asn His Val Val Ser Leu Thr Gly Lys Glu Arg Glu Leu Ser
610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
                660                 665                 670

Leu Lys Ala Gly Ile Ser Asn Lys Ser Asn Arg Tyr Asn Asp Asn Tyr
                675                 680                 685

Asn Asn Tyr Ile Ser Lys Cys Ser Ile Ile Thr Asp Leu Ser Lys Phe
690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
                740                 745                 750

Ile Gly Asp His Ile Val Asp Leu Asn Asn Val Asp Glu Gln Ser Gly
                755                 760                 765

Leu Tyr Arg Tyr His Met Gly Gly Ile Glu Gly Trp Cys Gln Lys Leu
770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Ile Arg Leu Met Glu Gly Gln Thr His Ala Gln Ala
                820                 825                 830

Asp Tyr Leu Leu Ala Leu Asn Ser Leu Lys Leu Leu Tyr Lys Glu Tyr
                835                 840                 845

Ala Gly Ile Gly His Lys Leu Lys Gly Thr Glu Thr Tyr Ile Ser Arg
                850                 855                 860

Asp Met Gln Phe Met Ser Lys Thr Ile Gln His Asn Gly Val Tyr Tyr
865                 870                 875                 880
```

```
Pro Ala Ser Ile Lys Lys Val Leu Arg Val Gly Pro Trp Ile Asn Thr
            885                 890                 895
Ile Leu Asp Asp Phe Lys Val Ser Leu Glu Ser Ile Gly Ser Leu Thr
            900                 905                 910
Gln Glu Leu Glu Tyr Arg Gly Glu Ser Leu Leu Cys Ser Leu Ile Phe
            915                 920                 925
Arg Asn Val Trp Leu Tyr Asn Gln Ile Ala Leu Gln Leu Lys Asn His
            930                 935                 940
Ala Leu Cys Asn Asn Lys Leu Tyr Leu Asp Ile Leu Lys Val Leu Lys
945                 950                 955                 960
His Leu Lys Thr Phe Phe Asn Leu Asp Asn Ile Asp Thr Ala Leu Thr
            965                 970                 975
Leu Tyr Met Asn Leu Pro Met Leu Phe Gly Gly Gly Asp Pro Asn Leu
            980                 985                 990
Leu Tyr Arg Ser Phe Tyr Arg Arg Thr Pro Asp Phe Leu Thr Glu Ala
            995                 1000                1005
Ile Val His Ser Val Phe Ile Leu Ser Tyr Tyr Thr Asn His Asp Leu
            1010                1015                1020
Lys Asp Lys Leu Gln Asp Leu Ser Asp Asp Arg Leu Asn Lys Phe Leu
1025                1030                1035                1040
Thr Cys Ile Ile Thr Phe Asp Lys Asn Pro Asn Ala Glu Phe Val Thr
            1045                1050                1055
Leu Met Arg Asp Pro Gln Ala Leu Gly Ser Glu Arg Gln Ala Lys Ile
            1060                1065                1070
Thr Ser Glu Ile Asn Arg Leu Ala Val Thr Glu Val Leu Ser Thr Ala
            1075                1080                1085
Pro Asn Lys Ile Phe Ser Lys Ser Ala Gln His Tyr Thr Thr Thr Glu
            1090                1095                1100
Ile Asp Leu Asn Asp Ile Met Gln Asn Ile Glu Pro Thr Tyr Pro His
1105                1110                1115                1120
Gly Leu Arg Val Val Tyr Glu Ser Leu Pro Phe Tyr Lys Ala Glu Lys
            1125                1130                1135
Ile Val Asn Leu Ile Ser Gly Thr Lys Ser Ile Thr Asn Ile Leu Glu
            1140                1145                1150
Lys Thr Ser Ala Ile Asp Leu Thr Asp Ile Asp Arg Ala Thr Glu Met
            1155                1160                1165
Met Arg Lys Asn Ile Thr Leu Leu Ile Arg Ile Leu Pro Leu Asp Cys
            1170                1175                1180
Asn Arg Asp Lys Arg Glu Ile Leu Ser Met Glu Asn Leu Ser Ile Thr
1185                1190                1195                1200
Glu Leu Ser Lys Tyr Val Arg Glu Arg Ser Trp Ser Leu Ser Asn Ile
            1205                1210                1215
Val Gly Val Thr Ser Pro Ser Ile Met Tyr Thr Met Asp Ile Lys Tyr
            1220                1225                1230
Thr Thr Ser Thr Ile Ser Ser Gly Ile Ile Glu Lys Tyr Asn Val
            1235                1240                1245
Asn Ser Leu Thr Arg Gly Glu Arg Gly Pro Thr Lys Pro Trp Val Gly
            1250                1255                1260
Ser Ser Thr Gln Glu Lys Lys Thr Met Pro Val Tyr Asn Arg Gln Val
1265                1270                1275                1280
Leu Thr Lys Lys Gln Arg Asp Gln Ile Asp Leu Leu Ala Lys Leu Asp
            1285                1290                1295
Trp Val Tyr Ala Ser Ile Asp Asn Lys Asp Glu Phe Met Glu Glu Leu
```

-continued

```
                    1300                1305                1310
Ser Ile Gly Thr Leu Gly Leu Thr Tyr Glu Lys Ala Lys Lys Leu Phe
        1315                1320                1325
Pro Gln Tyr Leu Ser Val Asn Tyr Leu His Arg Leu Thr Val Ser Ser
        1330                1335                1340
Arg Pro Cys Glu Phe Pro Ala Ser Ile Pro Ala Tyr Arg Thr Thr Asn
1345                1350                1355                1360
Tyr His Phe Asp Thr Ser Pro Ile Asn Arg Ile Leu Thr Glu Lys Tyr
            1365                1370                1375
Gly Asp Glu Asp Ile Asp Ile Val Phe Gln Asn Cys Ile Ser Phe Gly
            1380                1385                1390
Leu Ser Leu Met Ser Val Val Glu Gln Phe Thr Asn Val Cys Pro Asn
            1395                1400                1405
Arg Ile Ile Leu Ile Pro Lys Leu Asn Glu Ile His Leu Met Lys Pro
        1410                1415                1420
Pro Ile Phe Thr Gly Asp Val Asp Ile His Lys Leu Lys Gln Val Ile
1425                1430                1435                1440
Gln Lys Gln His Met Phe Leu Pro Asp Lys Ile Ser Leu Thr Gln Tyr
            1445                1450                1455
Val Glu Leu Phe Leu Ser Asn Lys Thr Leu Lys Ser Gly Ser His Val
            1460                1465                1470
Asn Ser Asn Leu Ile Leu Ala His Lys Ile Ser Asp Tyr Phe His Asn
        1475                1480                1485
Thr Tyr Ile Leu Ser Thr Asn Leu Ala Gly His Trp Ile Leu Ile Ile
        1490                1495                1500
Gln Leu Met Lys Asp Ser Lys Gly Ile Phe Glu Lys Asp Trp Gly Glu
1505                1510                1515                1520
Gly Tyr Ile Thr Asp His Met Phe Ile Asn Leu Lys Val Phe Phe Asn
            1525                1530                1535
Ala Tyr Lys Thr Tyr Leu Leu Cys Phe His Lys Gly Tyr Gly Lys Ala
            1540                1545                1550
Lys Leu Glu Cys Asp Met Asn Thr Ser Asp Leu Leu Cys Val Leu Glu
        1555                1560                1565
Leu Ile Asp Ser Ser Tyr Trp Lys Ser Met Ser Lys Val Phe Leu Glu
        1570                1575                1580
Gln Lys Val Ile Lys Tyr Ile Leu Ser Gln Asp Ala Ser Leu His Arg
1585                1590                1595                1600
Val Lys Gly Cys His Ser Phe Lys Leu Trp Phe Leu Lys Arg Leu Asn
            1605                1610                1615
Val Ala Glu Phe Thr Val Cys Pro Trp Val Val Asn Ile Asp Tyr His
            1620                1625                1630
Pro Thr His Met Lys Ala Ile Leu Thr Tyr Ile Asp Leu Val Arg Met
            1635                1640                1645
Gly Leu Ile Asn Ile Asp Arg Ile His Ile Lys Asn Lys His Lys Phe
        1650                1655                1660
Asn Asp Glu Phe Tyr Thr Ser Asn Leu Phe Tyr Ile Asn Tyr Asn Phe
1665                1670                1675                1680
Ser Asp Asn Thr His Leu Leu Thr Lys His Ile Arg Ile Ala Asn Ser
            1685                1690                1695
Glu Leu Glu Asn Asn Tyr Asn Lys Leu Tyr His Pro Thr Pro Glu Thr
        1700                1705                1710
Leu Glu Asn Ile Leu Ala Asn Pro Ile Lys Ser Asn Asp Lys Lys Thr
        1715                1720                1725
```

-continued

```
Leu Asn Asp Tyr Cys Ile Gly Lys Asn Val Asp Ser Ile Met Leu Pro
    1730                1735                1740
Leu Leu Ser Asn Lys Lys Leu Ile Lys Ser Ser Ala Met Ile Arg Thr
1745                1750                1755                1760
Asn Tyr Ser Lys Gln Asp Leu Tyr Asn Leu Phe Pro Met Val Val Ile
                1765                1770                1775
Asp Arg Ile Ile Asp His Ser Gly Asn Thr Ala Lys Ser Asn Gln Leu
            1780                1785                1790
Tyr Thr Thr Thr Ser His Gln Ile Ser Leu Val His Asn Ser Thr Ser
                1795                1800                1805
Leu Tyr Cys Met Leu Pro Trp His His Ile Asn Arg Phe Asn Phe Val
    1810                1815                1820
Phe Ser Ser Thr Gly Cys Lys Ile Ser Ile Glu Tyr Ile Leu Lys Asp
1825                1830                1835                1840
Leu Lys Ile Lys Asp Pro Asn Cys Ile Ala Phe Ile Gly Glu Gly Ala
                1845                1850                1855
Gly Asn Leu Leu Leu Arg Thr Val Val Glu Leu His Pro Asp Ile Arg
            1860                1865                1870
Tyr Ile Tyr Arg Ser Leu Lys Asp Cys Asn Asp His Ser Leu Pro Ile
                1875                1880                1885
Glu Phe Leu Arg Leu Tyr Asn Gly His Ile Asn Ile Asp Tyr Gly Glu
    1890                1895                1900
Asn Leu Thr Ile Pro Ala Thr Asp Ala Thr Asn Asn Ile His Trp Ser
1905                1910                1915                1920
Tyr Leu His Ile Lys Phe Ala Glu Pro Ile Ser Leu Phe Val Cys Asp
                1925                1930                1935
Ala Glu Leu Ser Val Thr Val Asn Trp Ser Lys Ile Ile Glu Trp
            1940                1945                1950
Ser Lys His Val Arg Lys Cys Lys Tyr Cys Ser Ser Val Asn Lys Cys
                1955                1960                1965
Met Leu Ile Val Lys Tyr His Ala Gln Asp Asp Ile Asp Phe Lys Leu
    1970                1975                1980
Asp Asn Ile Thr Ile Leu Lys Thr Tyr Val Cys Leu Gly Ser Lys Leu
1985                1990                1995                2000
Lys Gly Ser Glu Val Tyr Leu Val Leu Thr Ile Gly Pro Ala Asn Ile
                2005                2010                2015
Phe Pro Val Phe Asn Val Val Gln Asn Ala Lys Leu Ile Leu Ser Arg
            2020                2025                2030
Thr Lys Asn Phe Ile Met Pro Lys Lys Ala Asp Lys Glu Ser Ile Asp
    2035                2040                2045
Ala Asn Ile Lys Ser Leu Ile Pro Phe Leu Cys Tyr Pro Ile Thr Lys
    2050                2055                2060
Lys Gly Ile Asn Thr Ala Leu Ser Lys Leu Lys Ser Val Val Ser Gly
2065                2070                2075                2080
Asp Ile Leu Ser Tyr Ser Ile Ala Gly Arg Asn Glu Val Phe Ser Asn
                2085                2090                2095
Lys Leu Ile Asn His Lys His Met Asn Ile Leu Lys Trp Phe Asn His
            2100                2105                2110
Val Leu Asn Phe Arg Ser Thr Glu Leu Asn Tyr Asn His Leu Tyr Met
    2115                2120                2125
Val Glu Ser Thr Tyr Pro Tyr Leu Ser Glu Leu Leu Asn Ser Leu Thr
    2130                2135                2140
```

```
Thr Asn Glu Leu Lys Lys Leu Ile Lys Ile Thr Gly Ser Leu Leu Tyr
2145                2150                2155                2160

Asn Phe His Asn Glu
            2165

<210> SEQ ID NO 30
<211> LENGTH: 2165
<212> TYPE: PRT
<213> ORGANISM: Virus

<400> SEQUENCE: 30

Met Asp Pro Ile Ile Asn Gly Asn Ser Ala Asn Val Tyr Leu Thr Asp
 1               5                  10                  15

Ser Tyr Leu Lys Gly Val Ile Ser Phe Ser Glu Cys Asn Ala Leu Gly
                20                  25                  30

Ser Tyr Ile Phe Asn Gly Pro Tyr Leu Lys Asn Asp Tyr Thr Asn Leu
            35                  40                  45

Ile Ser Arg Gln Asn Pro Leu Ile Glu His Met Asn Leu Lys Lys Leu
 50                  55                  60

Asn Ile Thr Gln Ser Leu Ile Ser Lys Tyr His Lys Gly Glu Ile Lys
 65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
                100                 105                 110

Ile Arg Arg Ala Ile Glu Ile Ser Asp Val Lys Val Tyr Ala Ile Leu
            115                 120                 125

Asn Lys Leu Gly Leu Lys Glu Lys Asp Lys Ile Lys Ser Asn Asn Gly
130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
            195                 200                 205

Asn Leu Tyr Thr Lys Leu Asn Asn Ile Leu Thr Gln Tyr Arg Ser Asn
210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
            275                 280                 285

Ser Asn Cys Leu Asn Thr Leu Asn Lys Ser Leu Gly Leu Arg Cys Gly
290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350
```

-continued

```
Arg Lys Arg Phe Tyr Asn Ser Met Leu Asn Asn Ile Thr Asp Ala Ala
            355                 360                 365
Asn Lys Ala Gln Lys Asn Leu Leu Ser Arg Val Cys His Thr Leu Leu
    370                 375                 380
Asp Lys Thr Val Ser Asp Asn Ile Ile Asn Gly Arg Trp Ile Ile Leu
385                 390                 395                 400
Leu Ser Lys Phe Leu Lys Leu Ile Lys Leu Ala Gly Asp Asn Asn Leu
                405                 410                 415
Asn Asn Leu Ser Glu Leu Tyr Phe Leu Phe Arg Ile Phe Gly His Pro
            420                 425                 430
Met Val Asp Glu Arg Gln Ala Met Asp Ala Val Lys Ile Asn Cys Asn
            435                 440                 445
Glu Thr Lys Phe Tyr Leu Leu Ser Ser Leu Ser Met Leu Arg Gly Ala
            450                 455                 460
Phe Ile Tyr Arg Ile Ile Lys Gly Phe Val Asn Asn Tyr Asn Arg Trp
465                 470                 475                 480
Pro Thr Leu Arg Asn Ala Ile Val Leu Pro Leu Arg Trp Leu Thr Tyr
                485                 490                 495
Tyr Lys Leu Asn Thr Tyr Pro Ser Leu Leu Glu Leu Thr Glu Arg Asp
            500                 505                 510
Leu Ile Val Leu Ser Gly Leu Arg Phe Tyr Arg Glu Phe Arg Leu Pro
            515                 520                 525
Lys Lys Val Asp Leu Glu Met Ile Ile Asn Asp Lys Ala Ile Ser Pro
            530                 535                 540
Pro Lys Asn Leu Ile Trp Thr Ser Phe Pro Arg Asn Tyr Met Pro Ser
545                 550                 555                 560
His Ile Gln Asn Tyr Ile Glu His Glu Lys Leu Lys Phe Ser Glu Ser
                565                 570                 575
Asp Lys Ser Arg Arg Val Leu Glu Tyr Tyr Leu Arg Asp Asn Lys Phe
            580                 585                 590
Asn Glu Cys Asp Leu Tyr Asn Cys Val Val Asn Gln Ser Tyr Leu Asn
            595                 600                 605
Asn Pro Asn His Val Val Ser Leu Thr Gly Lys Glu Arg Glu Leu Ser
    610                 615                 620
Val Gly Arg Met Phe Ala Met Gln Pro Gly Met Phe Arg Gln Val Gln
625                 630                 635                 640
Ile Leu Ala Glu Lys Met Ile Ala Glu Asn Ile Leu Gln Phe Phe Pro
                645                 650                 655
Glu Ser Leu Thr Arg Tyr Gly Asp Leu Glu Leu Gln Lys Ile Leu Glu
            660                 665                 670
Leu Lys Ala Gly Ile Ser Asn Lys Ser Asn Arg Tyr Asn Asp Asn Tyr
            675                 680                 685
Asn Asn Tyr Ile Ser Lys Cys Ser Ile Ile Thr Asp Leu Ser Lys Phe
            690                 695                 700
Asn Gln Ala Phe Arg Tyr Glu Thr Ser Cys Ile Cys Ser Asp Val Leu
705                 710                 715                 720
Asp Glu Leu His Gly Val Gln Ser Leu Phe Ser Trp Leu His Leu Thr
                725                 730                 735
Ile Pro His Val Thr Ile Ile Cys Thr Tyr Arg His Ala Pro Pro Tyr
            740                 745                 750
Ile Gly Asp His Ile Val Asp Leu Asn Asn Val Asp Glu Gln Ser Gly
            755                 760                 765
```

-continued

Leu Tyr Arg Tyr His Met Gly Gly Ile Glu Gly Trp Cys Gln Lys Leu
        770             775             780

Trp Thr Ile Glu Ala Ile Ser Leu Leu Asp Leu Ile Ser Leu Lys Gly
785             790             795             800

Lys Phe Ser Ile Thr Ala Leu Ile Asn Gly Asp Asn Gln Ser Ile Asp
            805             810             815

Ile Ser Lys Pro Ile Arg Leu Met Glu Gly Gln Thr His Ala Gln Ala
        820             825             830

Asp Tyr Leu Leu Ala Leu Asn Ser Leu Lys Leu Leu Tyr Lys Glu Tyr
        835             840             845

Ala Gly Ile Gly His Lys Leu Lys Gly Thr Glu Thr Tyr Ile Ser Arg
    850             855             860

Asp Met Gln Phe Met Ser Lys Thr Ile Gln His Asn Gly Val Tyr Tyr
865             870             875             880

Pro Ala Ser Ile Lys Lys Val Leu Arg Val Gly Pro Trp Ile Asn Thr
            885             890             895

Ile Leu Asp Asp Phe Lys Val Ser Leu Glu Ser Ile Gly Ser Leu Thr
        900             905             910

Gln Glu Leu Glu Tyr Arg Gly Glu Ser Leu Leu Cys Ser Leu Ile Phe
    915             920             925

Arg Asn Val Trp Leu Tyr Asn Gln Ile Ala Leu Gln Leu Lys Asn His
930             935             940

Ala Leu Cys Asn Asn Lys Leu Tyr Leu Asp Ile Leu Lys Val Leu Lys
945             950             955             960

His Leu Lys Thr Phe Phe Asn Leu Asp Asn Ile Asp Thr Ala Leu Thr
            965             970             975

Leu Tyr Met Asn Leu Pro Met Leu Phe Gly Gly Gly Asp Pro Asn Leu
        980             985             990

Leu Tyr Arg Ser Phe Tyr Arg Arg Thr Pro Asp Phe Leu Thr Glu Ala
        995             1000            1005

Ile Val His Ser Val Phe Ile Leu Ser Tyr Tyr Thr Asn His Asp Leu
    1010            1015            1020

Lys Asp Lys Leu Gln Asp Leu Ser Asp Asp Arg Leu Asn Lys Phe Leu
1025            1030            1035            1040

Thr Cys Ile Ile Thr Phe Asp Lys Asn Pro Asn Ala Glu Phe Val Thr
            1045            1050            1055

Leu Met Arg Asp Pro Gln Ala Leu Gly Ser Glu Arg Gln Ala Lys Ile
            1060            1065            1070

Thr Ser Glu Ile Asn Arg Leu Ala Val Thr Glu Val Leu Ser Thr Ala
        1075            1080            1085

Pro Asn Lys Ile Phe Ser Lys Ser Ala Gln His Tyr Thr Thr Thr Glu
        1090            1095            1100

Ile Asp Leu Asn Asp Ile Met Gln Asn Ile Glu Pro Thr Tyr Pro His
1105            1110            1115            1120

Gly Leu Arg Val Val Tyr Glu Ser Leu Pro Phe Tyr Lys Ala Glu Lys
            1125            1130            1135

Ile Val Asn Leu Ile Ser Gly Thr Lys Ser Ile Thr Asn Ile Leu Glu
            1140            1145            1150

Lys Thr Ser Ala Ile Asp Leu Thr Asp Ile Asp Arg Ala Thr Glu Met
        1155            1160            1165

Met Arg Lys Asn Ile Thr Leu Leu Ile Arg Ile Leu Pro Leu Asp Cys
1170            1175            1180

Asn Arg Asp Lys Arg Glu Ile Leu Ser Met Glu Asn Leu Ser Ile Thr

-continued

```
            1185                1190                1195                1200
Glu Leu Ser Lys Tyr Val Arg Glu Arg Ser Trp Ser Leu Ser Asn Ile
                1205                1210                1215
Val Gly Val Thr Ser Pro Ser Ile Met Tyr Thr Met Asp Ile Lys Tyr
            1220                1225                1230
Thr Thr Ser Thr Ile Ser Ser Gly Ile Ile Ile Glu Lys Tyr Asn Val
            1235                1240                1245
Asn Ser Leu Thr Arg Gly Glu Arg Gly Pro Thr Lys Pro Trp Val Gly
            1250                1255                1260
Ser Ser Thr Gln Glu Lys Lys Thr Met Pro Val Tyr Asn Arg Gln Val
1265                1270                1275                1280
Leu Thr Lys Lys Gln Arg Asp Gln Ile Asp Leu Leu Ala Lys Leu Asp
                1285                1290                1295
Trp Val Tyr Ala Ser Ile Asp Asn Lys Asp Glu Phe Met Glu Glu Leu
            1300                1305                1310
Ser Ile Gly Thr Leu Gly Leu Thr Tyr Glu Lys Ala Lys Lys Leu Phe
            1315                1320                1325
Pro Gln Tyr Leu Ser Val Asn Tyr Leu His Arg Leu Thr Val Ser Ser
            1330                1335                1340
Arg Pro Cys Glu Phe Pro Ala Ser Ile Pro Ala Tyr Arg Thr Thr Asn
1345                1350                1355                1360
Tyr His Phe Asp Thr Ser Pro Ile Asn Arg Ile Leu Thr Glu Lys Tyr
                1365                1370                1375
Gly Asp Glu Asp Ile Asp Ile Val Phe Gln Asn Cys Ile Ser Phe Gly
            1380                1385                1390
Leu Ser Leu Met Ser Val Val Glu Gln Phe Thr Asn Val Cys Pro Asn
            1395                1400                1405
Arg Ile Ile Leu Ile Pro Lys Leu Asn Glu Ile His Leu Met Lys Pro
            1410                1415                1420
Pro Ile Phe Thr Gly Asp Val Asp Ile His Lys Leu Lys Gln Val Ile
1425                1430                1435                1440
Gln Lys Gln His Met Phe Leu Pro Asp Lys Ile Ser Leu Thr Gln Tyr
                1445                1450                1455
Val Glu Leu Phe Leu Ser Asn Lys Thr Leu Lys Ser Gly Ser His Val
            1460                1465                1470
Asn Ser Asn Leu Ile Leu Ala His Lys Ile Ser Asp Tyr Phe His Asn
            1475                1480                1485
Thr Tyr Ile Leu Ser Thr Asn Leu Ala Gly His Trp Ile Leu Ile Ile
            1490                1495                1500
Gln Leu Met Lys Asp Ser Lys Gly Ile Phe Glu Lys Asp Trp Gly Glu
1505                1510                1515                1520
Gly Tyr Ile Thr Asp His Met Phe Ile Asn Leu Lys Val Phe Phe Asn
                1525                1530                1535
Ala Tyr Lys Thr Tyr Leu Leu Cys Phe His Lys Gly Tyr Gly Lys Ala
            1540                1545                1550
Lys Leu Glu Cys Asp Met Asn Thr Ser Asp Leu Leu Cys Val Leu Glu
            1555                1560                1565
Leu Ile Asp Ser Ser Tyr Trp Lys Ser Met Ser Lys Val Phe Leu Glu
            1570                1575                1580
Gln Lys Val Ile Lys Tyr Ile Leu Ser Gln Asp Ala Ser Leu His Arg
1585                1590                1595                1600
Val Lys Gly Cys His Ser Phe Lys Leu Trp Phe Leu Lys Arg Leu Asn
                1605                1610                1615
```

-continued

```
Val Ala Glu Phe Thr Val Cys Pro Trp Val Asn Ile Asp Tyr His
            1620                1625                1630

Pro Thr His Met Lys Ala Ile Leu Thr Tyr Ile Asp Leu Val Arg Met
            1635                1640                1645

Gly Leu Ile Asn Ile Asp Arg Ile His Ile Lys Asn Lys His Lys Phe
            1650                1655                1660

Asn Asp Glu Phe Tyr Thr Ser Asn Leu Phe Tyr Ile Asn Tyr Asn Phe
1665                1670                1675                1680

Ser Asp Asn Thr His Leu Leu Thr Lys His Ile Arg Ile Ala Asn Ser
            1685                1690                1695

Glu Leu Glu Asn Asn Tyr Asn Lys Leu Tyr His Pro Thr Pro Glu Thr
            1700                1705                1710

Leu Glu Asn Ile Leu Ala Asn Pro Ile Lys Ser Asn Asp Lys Lys Thr
            1715                1720                1725

Leu Asn Asp Tyr Cys Ile Gly Lys Asn Val Asp Ser Ile Met Leu Pro
            1730                1735                1740

Leu Leu Ser Asn Lys Lys Leu Ile Lys Ser Ser Ala Met Ile Arg Thr
1745                1750                1755                1760

Asn Tyr Ser Lys Gln Asp Leu Tyr Asn Leu Phe Pro Met Val Val Ile
            1765                1770                1775

Asp Arg Ile Ile Asp His Ser Gly Asn Thr Ala Lys Ser Asn Gln Leu
            1780                1785                1790

Tyr Thr Thr Thr Ser His Gln Ile Ser Leu Val His Asn Ser Thr Ser
            1795                1800                1805

Leu Tyr Cys Met Leu Pro Trp His His Ile Asn Arg Phe Asn Phe Val
            1810                1815                1820

Phe Ser Ser Thr Gly Cys Lys Ile Ser Ile Glu Tyr Ile Leu Lys Asp
1825                1830                1835                1840

Leu Lys Ile Lys Asp Pro Asn Cys Ile Ala Phe Ile Gly Glu Gly Ala
            1845                1850                1855

Gly Asn Leu Leu Leu Arg Thr Val Val Glu Leu His Pro Asp Ile Arg
            1860                1865                1870

Tyr Ile Tyr Arg Ser Leu Lys Asp Cys Asn Asp His Ser Leu Pro Ile
            1875                1880                1885

Glu Phe Leu Arg Leu Tyr Asn Gly His Ile Asn Ile Asp Tyr Gly Glu
            1890                1895                1900

Asn Leu Thr Ile Pro Ala Thr Asp Ala Thr Asn Asn Ile His Trp Ser
1905                1910                1915                1920

Tyr Leu His Ile Lys Phe Ala Glu Pro Ile Ser Leu Phe Val Cys Asp
            1925                1930                1935

Ala Glu Leu Ser Val Thr Val Asn Trp Ser Lys Ile Ile Glu Trp
            1940                1945                1950

Ser Lys His Val Arg Lys Cys Lys Tyr Cys Ser Ser Val Asn Lys Cys
            1955                1960                1965

Met Leu Ile Val Lys Tyr His Ala Gln Asp Ile Asp Phe Lys Leu
            1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Leu Thr Ile Gly Pro Ala Asn Ile
            2005                2010                2015

Phe Pro Val Phe Asn Val Val Gln Asn Ala Lys Leu Ile Leu Ser Arg
            2020                2025                2030
```

-continued

```
Thr Lys Asn Phe Ile Met Pro Lys Lys Ala Asp Lys Glu Ser Ile Asp
        2035                2040                2045
Ala Asn Ile Lys Ser Leu Ile Pro Phe Leu Cys Tyr Pro Ile Thr Lys
    2050                2055                2060
Lys Gly Ile Asn Thr Ala Leu Ser Lys Leu Lys Ser Val Val Ser Gly
2065                2070                2075                2080
Asp Ile Leu Ser Tyr Ser Ile Ala Gly Arg Asn Glu Val Phe Ser Asn
            2085                2090                2095
Lys Leu Ile Asn His Lys His Met Asn Ile Leu Lys Trp Phe Asn His
            2100                2105                2110
Val Leu Asn Phe Arg Ser Thr Glu Leu Asn Tyr Asn His Leu Tyr Met
            2115                2120                2125
Val Glu Ser Thr Tyr Pro Tyr Leu Ser Glu Leu Leu Asn Ser Leu Thr
            2130                2135                2140
Thr Asn Glu Leu Lys Lys Leu Ile Lys Ile Thr Gly Ser Leu Leu Tyr
2145                2150                2155                2160
Asn Phe His Asn Glu
            2165

<210> SEQ ID NO 31
<211> LENGTH: 21
<212> TYPE: DNA
<213> ORGANISM: Artificial Sequence
<220> FEATURE:
<223> OTHER INFORMATION: Oligonucleotide

<400> SEQUENCE: 31
ggtggccggc atggtcccag c                                              21

<210> SEQ ID NO 32
<211> LENGTH: 24
<212> TYPE: DNA
<213> ORGANISM: Artificial Sequence
<220> FEATURE:
<223> OTHER INFORMATION: Oligonucleotide

<400> SEQUENCE: 32
ctcgctggcg ccggctgggc aaca                                           24

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide

<400> SEQUENCE: 33
ttccgagggg accgtcccct cggt                                           24

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide

<400> SEQUENCE: 34
aatggcgaat gggacgtcga cagc                                           24

<210> SEQ ID NO 35
<211> LENGTH: 21
<212> TYPE: DNA
```

```
<213> ORGANISM: Artificial Sequence
<220> FEATURE:
<223> OTHER INFORMATION: Oligonucleotide

<400> SEQUENCE: 35
taacaaagcc cgaaggaagc t                                              21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide

<400> SEQUENCE: 36
gagttgctgc tgccaccgtt g                                              21

<210> SEQ ID NO 37
<211> LENGTH: 23
<212> TYPE: DNA
<213> ORGANISM: Artificial Sequence
<220> FEATURE:
<223> OTHER INFORMATION: Oligonucleotide

<400> SEQUENCE: 37
agcaataact agataacctt ggg                                            23

<210> SEQ ID NO 38
<211> LENGTH: 24
<212> TYPE: DNA
<213> ORGANISM: Artificial Sequence
<220> FEATURE:
<223> OTHER INFORMATION: Oligonucleotide

<400> SEQUENCE: 38
cctctaaacg ggtcttgagg gtct                                           24

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide

<400> SEQUENCE: 39
ttttgctgaa aggaggaact a                                              21

<210> SEQ ID NO 40
<211> LENGTH: 21
<212> TYPE: DNA
<213> ORGANISM: Artificial Sequence
<220> FEATURE:
<223> OTHER INFORMATION: Oligonucleotide

<400> SEQUENCE: 40
tatgcggccg cgtcgacggt a                                              21

<210> SEQ ID NO 41
<211> LENGTH: 18
<212> TYPE: DNA
<213> ORGANISM: Artificial Sequence
<220> FEATURE:
<223> OTHER INFORMATION: Oligonucleotide

<400> SEQUENCE: 41
ccgggcccgc cttcgaag                                                  18
```

```
<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
caccacctac cttactcaag t                                              21

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
tttgtttgtg ggtttgatgg ttgg                                           24

<210> SEQ ID NO 44
<211> LENGTH: 35
<212> TYPE: DNA
<213> ORGANISM: Artificial Sequence
<220> FEATURE:
<223> OTHER INFORMATION: Primer

<400> SEQUENCE: 44
gatatcaaga tctacaataa cattggggca aatgc                               35

<210> SEQ ID NO 45
<211> LENGTH: 31
<212> TYPE: DNA
<213> ORGANISM: Artificial Sequence
<220> FEATURE:
<223> OTHER INFORMATION: Primer

<400> SEQUENCE: 45
gctaagagat cttttttgaat aactaagcat g                                  31

<210> SEQ ID NO 46
<211> LENGTH: 46
<212> TYPE: DNA
<213> ORGANISM: Artificial Sequence
<220> FEATURE:
<223> OTHER INFORMATION: Oligonucleotide

<400> SEQUENCE: 46
tcttgactgt tgtggattgc agggttgact tgactccgat cgatcc                   46

<210> SEQ ID NO 47
<211> LENGTH: 49
<212> TYPE: DNA
<213> ORGANISM: Artificial Sequence
<220> FEATURE:
<223> OTHER INFORMATION: Oligonucleotide

<400> SEQUENCE: 47
cttgtgttgt tgttgtatgg tgtgtttctg attttgtatt gatcgatcc                49

<210> SEQ ID NO 48
<211> LENGTH: 11
<212> TYPE: PRT
<213> ORGANISM: Virus
<220> FEATURE:
```

-continued

```
<400> SEQUENCE: 48

Thr Asn Gly His Ala Lys Asn Asn Asp Thr Thr
 1               5                  10

<210> SEQ ID NO 49
<211> LENGTH: 12
<212> TYPE: PRT
<213> ORGANISM: Virus
<220> FEATURE:

<400> SEQUENCE: 49

Met Thr Met Pro Lys Ile Met Ile Leu Pro Asp Lys
 1               5                  10

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
tcacgaagga atcctggcaa atttgaaatt cga                           33

<210> SEQ ID NO 51
<211> LENGTH: 33
<212> TYPE: DNA
<213> ORGANISM: Artificial Sequence
<220> FEATURE:
<223> OTHER INFORMATION: Primer

<400> SEQUENCE: 51
gaaattcgag gtcatggttt aaatggtaag agg                           33

<210> SEQ ID NO 52
<211> LENGTH: 36
<212> TYPE: DNA
<213> ORGANISM: Artificial Sequence
<220> FEATURE:
<223> OTHER INFORMATION: Primer

<400> SEQUENCE: 52
tgcttaaatg gtaagagggg acattttagt cataat                        36

<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53
actaaacaat cagcaggtgt tgccatgagc aaa                           33

<210> SEQ ID NO 54
<211> LENGTH: 52
<212> TYPE: DNA
<213> ORGANISM: Artificial Sequence
<220> FEATURE:
<223> OTHER INFORMATION: Primer

<400> SEQUENCE: 54
gagctaaatt cacccaagat aagcttgtaa taaactgtca tatcatatat tg      52
```

-continued

```
<210> SEQ ID NO 55
<211> LENGTH: 42
<212> TYPE: DNA
<213> ORGANISM: Artificial Sequence
<220> FEATURE:
<223> OTHER INFORMATION: Primer

<400> SEQUENCE: 55
caaactatcc atctgtaata aagcttgcca gcagacgtat tg                           42

<210> SEQ ID NO 56
<211> LENGTH: 50
<212> TYPE: DNA
<213> ORGANISM: Artificial Sequence
<220> FEATURE:
<223> OTHER INFORMATION: Primer

<400> SEQUENCE: 56
ccatcaacaa cccaaaataa taaagcttta gtgatacaaa tgaccatgcc                   50
```

US 6,830,748 B1

RECOMBINANT RSV VIRUS EXPRESSION SYSTEMS AND VACCINES

CROSS REFERENCE TO RELATED APPLICATIONS

This application is a continuation-in-part of application Ser. No. 09/161,122, filed Sep. 25, 1998 abandoned, which claims priority benefit under 35 U.S.C. §119(e) of provisional Application Nos. 60/060,153, filed Sep. 26, 1997, 60/084,133, filed May 1, 1998, and 60/089,207, filed Jun. 12, 1998, each of which is incorporated herein by reference in its entirety.

1. INTRODUCTION

The present invention relates to recombinant negative strand virus RNA templates which may be used to express heterologous gene products in appropriate host cell systems and/or to construct recombinant viruses that express, package, and/or present the heterologous gene product. The expression products and chimeric viruses may advantageously be used in vaccine formulations. In particular, the present invention relates to methods of generating recombinant respiratory syncytial viruses and the use of these recombinant viruses as expression vectors and vaccines. The invention is described by way of examples in which recombinant respiratory syncytial viral genomes are used to generate infectious viral particles.

2. BACKGROUND OF THE INVENTION

A number of DNA viruses have been genetically engineered to direct the expression of heterologous proteins in host cell systems (e., vaccinia virus, baculovirus, etc.). Recently, similar advances have been made with positive-strand RNA viruses (e,g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccinia will, therefore, not induce immune stimulation.

By contrast, negative-strand RNA viruses such as influenza virus and respiratory syncytial virus, demonstrate a wide variability of their major epitopes. Indeed, thousands of variants of influenza have been identified; each strain evolving by antigenic drift. The negative-strand viruses such as influenza and respiratory syncytial virus would be attractive candidates for constructing chimeric viruses for use in vaccines because its genetic variability allows for the construction of a vast repertoire of vaccine formulations which will stimulate immunity without risk of developing a tolerance.

2.1. RESPIRATORY SYNCYTIAL VIRUS

Virus families containing enveloped single-stranded RNA of the negative-sense genome are classified into groups having non-segmented genomes (Paramyxoviridae, Rhabdoviridae) or those having segmented genomes (Orthomyxoviridae, Bunyaviridae and Arenaviridae). Paramyxoviridae have been classified into three genera: pararnyxovirus (sendai virus, parainfluenza viruses types 1–4, mumps, newcastle disease virus); morbillivirus (measles virus, canine distemper virus and rinderpest virus); and pneumovirus (respiratory syncytial virus and bovine respiratory syncytial virus).

Human respiratory syncytial virus (RSV) is the leading cause of severe lower respiratory tract disease in infants and young children and is responsible for considerable morbidity and mortality. Two antigenically diverse RSV subgroups A and B are present in human populations. RSV is also recognized as an important agent of disease in immuno-compromised adults and in the elderly. Due to the incomplete resistance to RSV reinfection induced by natural infection, RSV may infect multiple times during childhood and life. The goal of RSV immunoprophylaxis is to induce sufficient resistance to prevent the serious disease which may be associated with RSV infection. The current strategies for developing RSV vaccines principally revolve around the administration of purified viral antigen or the development of live attenuated RSV for intranasal administration. However, to date there have been no approved vaccines or highly effective antiviral therapy for RSV.

Infection with RSV can range from an unnoticeable infection to severe pneumonia and death. RSV possesses a single-stranded nonsegmented negative-sense RNA genome of 15,221 nucleotides (Collins, 1991, In The paramyxoviruses pp. 103–162, D. W. Kingsbury (ed.) Plenum Press, New York). The genome of RSV encodes 10 mRNAs (Collins et al., 1984, J. Virol. 49: 572–578). The genome contains a 44 nucleotide leader sequence at the 3' termini followed by the NS1-NS2-N-P-M-SH-G-F-M2-L and a 155 nucleotide trailer sequence at the 5' termini (Collins. 1991, supra). Each gene transcription unit contains a short stretch of conserved gene start (GS) sequence and a gene end (GE) sequences.

The viral genomic RNA is not infectious as naked RNA. The RNA genome of RSV is tightly encapsidated with the major nucleocapsid (N) protein and is associated with the phosphoprotein (P) and the large (L) polymerase subunit. These proteins form the nucleoprotein core, which is recognized as the minimum unit of infectivity (Brown et al., 1967, J. Virol. 1: 368–373). The RSV N, P, and L proteins form the viral RNA dependent RNA transcriptase for transcription and replication of the RSV genome (Yu et al., 1995, J. Virol. 69:2412–2419; Grosfeld et al., 1995, J. Virol. 69:5677–86). Recent studies indicate that the M2 gene products (M2-1 and M2-2) are involved and are required for transcription (Collins et al., 1996, Proc. Natl. Acad. Sci. 93:81–5).

The M protein is expressed as a peripheral membrane protein, whereas the F and G proteins are expressed as integral membrane proteins and are involved in virus attachment and viral entry into cells. The G and F proteins are the major antigens that elicit neutralizing antibodies in vivo (as reviewed in McIntosh and Chanock, 1990 "Respiratory Syncytial Virus" 2nd ed. Virology (D. M. Knipe et al., Ed.) Raven Press, Ltd., N.Y.). Antigenic dimorphism between the subgroups of RSV A and B is mainly linked to the G glycoprotein, whereas the F glycoprotein is more closely related between the subgroups.

Despite decades of research, no safe and effective RSV vaccine has been developed for the prevention of severe morbidity and mortality associated with RSV infection. A formalin-inactivated virus vaccine has failed to provide protection against RSV infection and its exacerbated symptoms during subsequent infection by the wild-type virus in infants (Kapikian et al., 1969, Am. J. Epidemiol. 89:405–21; Chin et al., 1969, Am. J. Epidemiol. 89:449–63) Efforts since have focused on developing live attenuated temperature-sensitive mutants by chemical mutagenesis or cold passage of the wild-type RSV (Gharpure et al., 1969, J. Virol. 3: 414–21; Crowe et al., 1994, Vaccine 12: 691–9). However, earlier trials yielded discouraging results with these live attenuated temperature sensitive mutants. Virus candidates were either underattenuated or overattenuated (Kim et al., 1973, Pediatrics 52:56–63; Wright et al., 1976, J. Pediatrics 88:931–6) and some of the vaccine candidates were genetically unstable which resulted in the loss of the attenuated phenotype (Hodes et al., 1974, Proc. Soc. Exp. Biol. Med. 145:1158–64).

Attempts have also been made to engineer recombinant vaccinia vectors which express RSV F or G envelope glycoproteins. However, the use of these vectors as vaccines to protect against RSV infection in animal studies has shown inconsistent results (Olmsted et al. 1986, Proc. Natl. Acad. Sci. 83:7462–7466; Collins et al., 1990, Vaccine 8:164–168).

Thus, efforts have turned to engineering recombinant RSV to generate vaccines. For a long time, negative-sense RNA viruses were refractory to study. Only recently has it been possible to recover negative strand RNA viruses using a recombinant reverse genetics approach (U.S. Pat. No. 5,166,057 to Palese et al.). Although this method was originally applied to engineer influenza viral genomes (Luytjes et al. 1989, Cell 59:1107–1113; Enami et al. 1990, Proc. Natl. Acad. Sci. USA 92: 11563–11567), it has been successfully applied to a wide variety of segmented and nonsegmented negative strand RNA viruses, including rabies (Schnell et al. 1994, EMBO J. 13: 4195–4203); VSV (Lawson et al., 1995, Proc. Natl. Acad. Sci USA 92: 4477–81); measles virus (Radecke et al., 1995, EMBO J. 14:5773–84); rinderpest virus (Baron & Barrett, 1997, J. Virol. 71: 1265–71); human parainfluenza virus (Hoffman & Baneree, 1997, J. Virol. 71:3272–7; Dubin et al., 1997, Virology 235:323–32); SV5 (He et al., 1997, Virology 237:249–60); respiratory syncytial virus (Collins et al. 1991, Proc. Nati. Acad. Sci. USA 88: 9663–9667) and Sendai virus (Park et al. 1991, Proc. Natl. Acad. Sci. USA 88:5537–5541; Kato et al. 1996, Genes to Cells 1:569–579). Although this approach has been used to successfully rescue RSV, a number of groups have reported that RSV is still refractory to study given several properties of RSV which distinguish it from the better characterized paramyxoviruses of the genera Paramyxovirus, Rubulavirus, and Morbillivirus. These differences include a greater number of RNAs, an unusual gene order at the 3' end of the genome, extensive strain-to-strain sequence diversity, several proteins not found in other nonsegmented negative strand RNA viruses and a requirement for the M2 protein (ORF1) to proceed with full processing of full length transcripts and rescue of a full length genome (Collins et al. PCT WO97/12032; Collins, P. L. et al. pp 1313–1357 of volume 1, *Fields Virology*, et al., Eds. (3rd ed., Raven Press, 1996).

3. SUMMARY OF THE INVENTION

The present invention relates to genetically engineered recombinant RS viruses and viral vectors which contain heterologous genes which for the use as vaccines. In accordance with the present invention, the recombinant RS viral vectors and viruses are engineered to contain heterologous genes, including genes of other viruses, pathogens, cellular genes, tumor antigens, or to encode combinations of genes from different strains of RSV.

Recombinant negative-strand viral RNA templates are described which may be used to transfect transformed cell that express the RNA dependent RNA polymerase and allow for complementation. Alternatively, a plasmid expressing the components of the RNA polymerase from an appropriate promoter can be used to transfect cells to allow for complementation of the negative-strand viral RNA templates. Complementation may also be achieved with the use of a helper virus or wild-type virus to provide the RNA dependent RNA polymerase. The RNA templates are prepared by transcription of appropriate DNA sequences with a DNA-directed RNA polymerase. The resulting RNA templates are of negative-or positive-polarity and contain appropriate terminal sequences which enable the viral RNA-synthesizing apparatus to recognize the template. Bicistronic mRNAs can be constructed to permit internal initiation of translation of viral sequences and allow for the expression of foreign protein coding sequences from the regular terminal initiation site, or vice versa.

As demonstrated by the examples described herein, recombinant RSV genome in the positive-sense or negative-sense orientation is co-transfected with expression vectors encoding the viral nucleocapsid (N) protein, the associated nucleocapsid phosphoprotein (P), the large (L) polymerase subunit protein, with or without the M2/ORF1 protein of RSV to generate infectious viral particles. Plasmids encoding RS virus polypeptides are used as the source of proteins which were able to replicate and transcribe synthetically derived RNPs. The minimum subset of RSV proteins needed for specific replication and expression of the viral RNP was found to be the three polymerase complex proteins (N, P and L). This suggests that the entire M2-1 gene function, supplied by a separate plasmid expressing M2-1, may not be absolutely required for the replication, expression and rescue of infectious RSV.

The expression products and/or chimeric virions obtained may advantageously be utilized in vaccine formulations. In particular, recombinant RSV genetically engineered to demonstrate an attenuated phenotype may be utilized as a live RSV vaccine. In another embodiment of the invention, recombinant RSV may be engineered to express the antigenic polypeptides of another strain of RSV (e.&., RSV G and F proteins) or another virus (e.g., an immunogenic peptide from gp120 of HIV) to generate a chimeric RSV to serve as a vaccine, that is able to elicit both vertebrate humoral and cell-mediated immune responses. The use of recombinant influenza or recombinant RSV for this purpose is especially attractive since these viruses demonstrate tremendous strain variability allowing for the construction of a vast repertoire of vaccine formulations. The ability to select from thousands of virus variants for constructing chimeric viruses obviates the problem of host resistance encountered when using other viruses such as vaccinia.

The present invention further relates to the attenuation of human respiratory syncytial virus by deletion of viral accessory gene(s) either singly or in combination.

The present invention further relates to the attenuation of human respiratory syncytial virus by mutagenesis of the viral M2-1 gene.

3.1. DEFINITIONS

As used herein, the following terms will have the meanings indicated:

cRNA=anti-genomic RNA

HA=hemagglutinin (envelope glycoprotein)

HIV=human immunodeficiency virus

L=large polymerase subunit

M=matrix protein (lines inside of envelope)

MDCK=Madin Darby canine kidney cells

MDBK=Madin Darby bovine kidney cells moi=multiplicity of infection

N=nucleocapsid protein

NA=neuraminidase (envelope glycoprotein)

NP=nucleoprotein (associated with RNA and required for polymerase activity)

NS=nonstructural protein (function unknown)

nt=nucleotide

P=nucleocapsid phosphoprotein

PA, PB1, PB2=RNA-directed RNA polymerase components

RNP=ribonucleoprotein (RNA, PB2, PB1, PA and NP)

rRNP=recombinant RNP

RSV=respiratory syncytial virus vRNA=genomic virus RNA viral polymerase complex=PA, PB1, PB2 and NP WSN=influenza A/WSN/33 virus WSN-HK virus: reassortment virus containing seven genes from WSN virus and the NA gene from influenza A/HK/8/68 virus

4. DESCRIPTION OF THE FIGURES

FIG. 1. Schematic representation of the RSV/CAT construct (pRSVA2CAT) used in rescue experiments. The approximate 100 nt long leader and 200 nt long trailer regions of RSV were constructed by the controlled annealing of synthetic oligonucleotides containing partial overlapping complementarity. The overlapping leader oligonucleotides are indicated by the 1L–5L (SEQ ID NOs: 1–5) shown in the construct. The overlapping trailer nucleotides are indicated by the 1T–9T (SEQ ID NOs: 6–14) shown in the construct. The nucleotide sequences of the leader and trailer DNAs were ligated into purified CAT gene DNA at the indicate XbaI and PstI sites respectively. This entire construct was then ligated into KpnI/HindIII digested pUC19. The inclusion of a T7 promoter sequence and a HgaI site flanking the trailer and leader sequences, respectively, allowed in vitro synthesis of RSV/CAT RNA transcripts containing the precise genomic sequence 3' and 5' ends.

Figure 2:
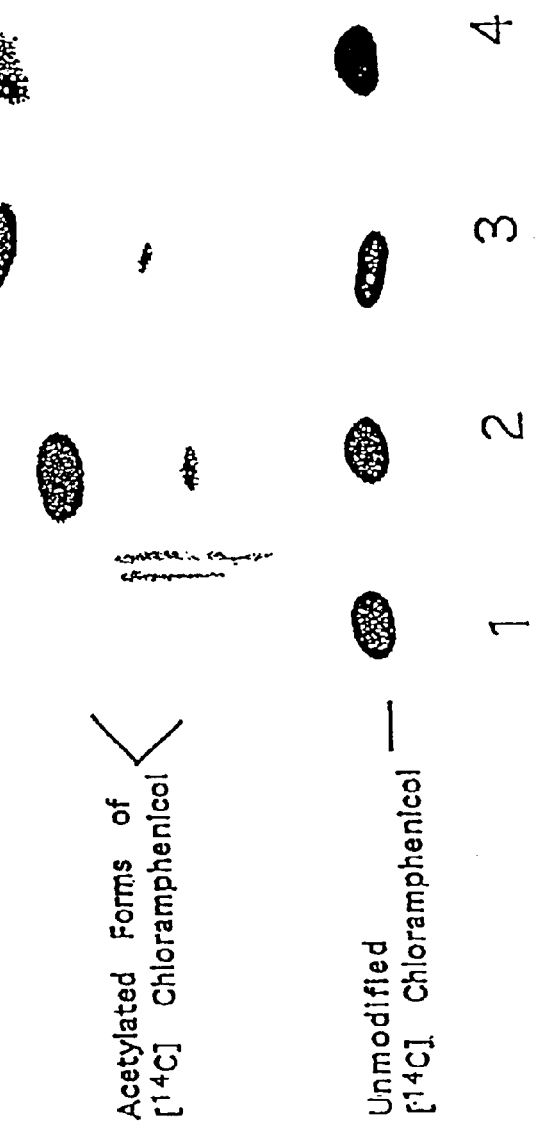

FIG. 2. Thin layer chromatogram (TLC) showing the CAT activity present in 293 cell extracts following infection and transfection with RNA transcribed from the RSV/CAT construct shown in FIG. 11 (SEQ ID NO:31). Confluent monolayers of 293 cells in six-well plates (~$10^6$ cells) were infected with either RSV A2 or B9320 at an m.o.i. of 0.1–1.0 pfu cell. At 1 hour post infection cells were transfected with 5–10 μg of CAT/RSV using the Transfect-Act™ protocol of Life Technologies. At 24 hours post infection the infected/transfected monolayers were harvested and processed for subsequence CAT assay according to Current Protocols in Molecular Biology, Vol. 1, Chapter 9.6.2; Gorman, et al., (1982) Mol. Cell. Biol. 2:1044–1051. Lanes 1, 2, 3 and 4 show the CAT activity present in (1) uninfected 293 cells, transfected with CAT/RSV-A2 infected 293 cells, co-infected with supernatant from (2) above. The CAT activity observed in each lane was produced from 1/5 of the total cellular extract from $10^6$ cells.

Figure 3:
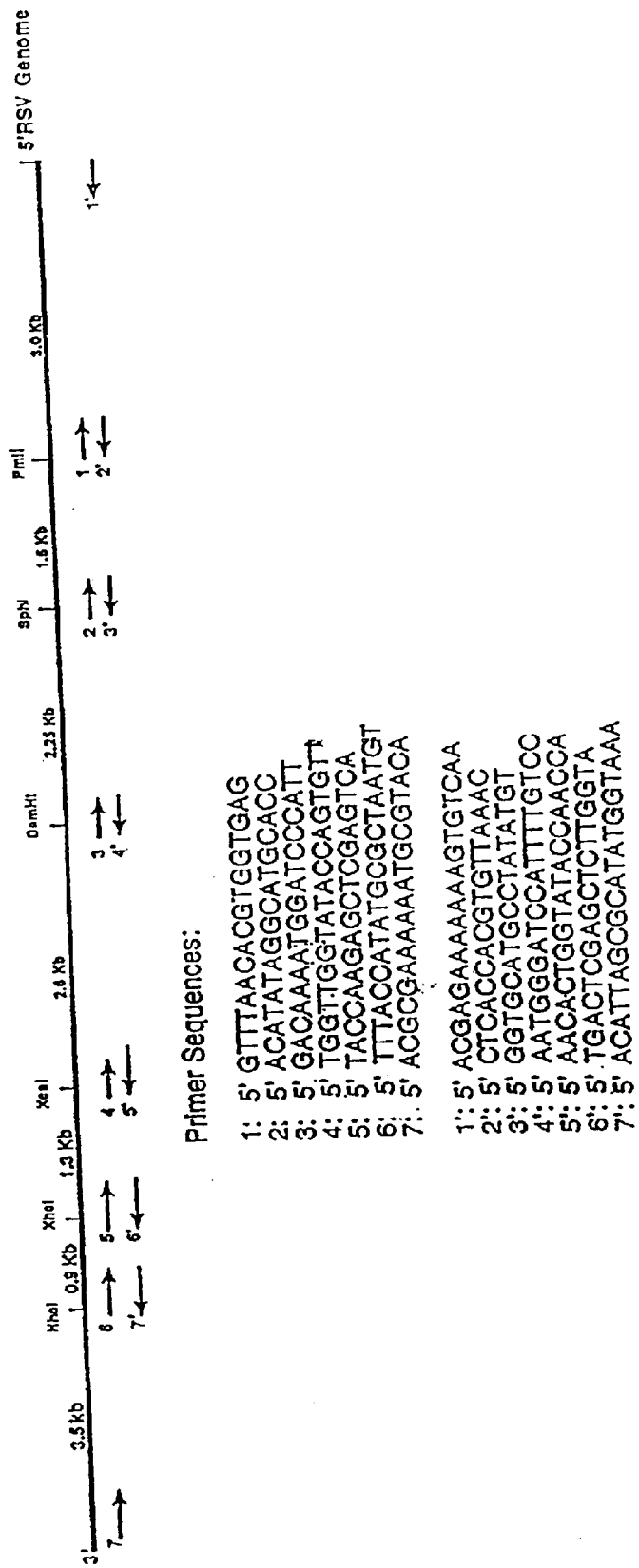

FIG. 3. Schematic representation of the RSV strain A2 genome showing the relative positions of the primer pairs used for the synthesis of cDNAs comprising the entire genome (SEQ ID NOs: 15–28). The endonuclease sites used to splice these clones together are indicated; these sites were present in the native RSV sequence and were included in the primers used for CDNA synthesis. Approximately 100 ng of viral genomic RNA was used in RT/PCR reactions for the separate synthesis of each of the seven cDNAs. The primers for the first and second strand CDNA synthesis from the genomic RNA template are also shown. For each cDNA, the primers for the first strand synthesis are nos. 1–7 and the primers for the second strand synthesis are nos. 1'–7'.

FIGS. 4A–C. Schematic representation of the RSV subgroup B strain B9320. BamHI sites were created in the oligonucleotide primers used for RT/PCR in order to clone the G and F genes from the B9320 strain into RSV subgroup A2 antigenomic CDNA (FIG. 4A). A cDNA fragment which contained G and F genes from 4326 nucleotides to 9387 nucleotides of A2 strain was first subcloned into pUC19 (pUCRVH). Bgl II sites were created at positions of 4630 (SH/G intergenic junction) (FIG. 4B) and 7554 (F/M2 intergenic junction (FIG. 4C). B93260 A-G and -F cDNA inserted into pUCR/H which is deleted of the A-G and F genes. The resulting antigenomic cDNA clone was termed as pRSVB-GF and was used to transfect Hep-2 cells to generate infectious RSVB-GF virus.

Figure 5:
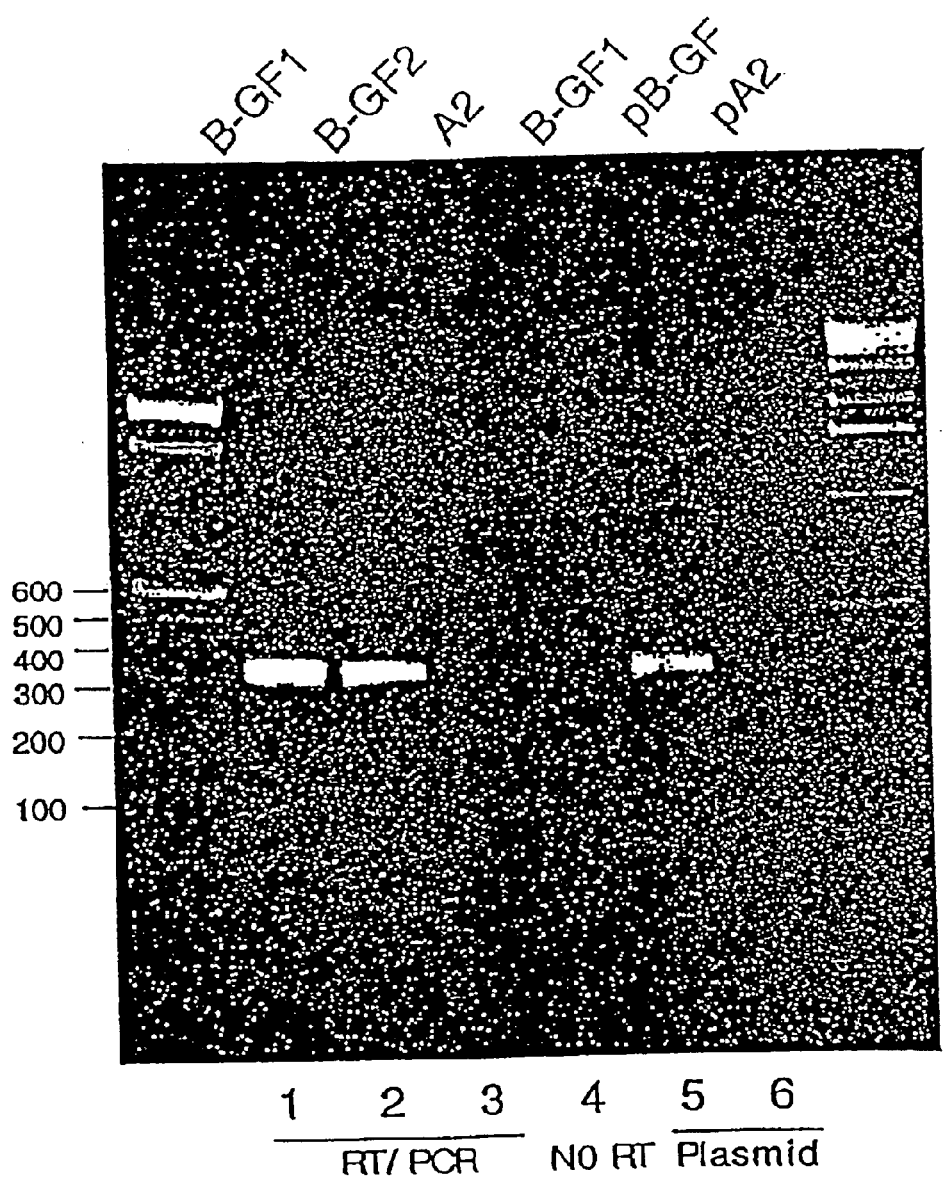

FIG. 5. Recombinant RSVB-GF virus was characterized by RT/PCR using RSV subgroup B specific primers. RSV subgroup B specific primers in the G region were incubated with aliquots of the recombinant RSV viral genomes and subjected to PCR. The PCR products were analyzed by electrophoresis on a 1% agarose gel and visualized by staining with ethidium bromide. As shown, no DNA product was produced in the RT/PCR reaction using RSV A2 as a template. However, a predicted product of 254 base pairs was seen in RT/PCR of RSVB-GF RNA and PCR control of plasmid pRSV-GF DNA as template, indicating the rescued virus contained G and F genes derived from B9320 virus.

FIGS. 6A-B. Identification of chimeric rRSVA2(B-G) by RT/PCR and Northern blot analysis of RNA expression. FIG. 6A. RT/PCT analysis of chimeric rRSV A2(B-G), in comparison with wild-type A2(A2). Virion RNA extracted from rRSVA2(B-G) (lanes 1, 2) and rRSVA2 (lanes 3,4) was reverse transcribed using a primer annealed to (−) sense vRNA in the RSV F gene in the presence (+) or absence (−) of reverse transcriptase (RT), followed by PCR with a primer fair flanking the B-G insertion site. No DNA was detected in RT/PCR when reverse transcriptase (RT) was absent (lanes 2,4). A cDNA fragment, which is about 1 kb bigger than the cDNA derived from A2, was produced from rRSVA(B-G). This longer PCR DNA product was digested by Stu I restriction enzyme unique to the inserted B-G gene (lane 5). 100 bp DNA size marker is indicated (M). FIG. 6B. Northern blot analysis of G mRNA expression. Hep2 cells were infected with RSV B9320, rRSVA2 and chimeric rRSVA2(B-G). At 48 hr postinfection, total cellular RNA was extracted and electrophoresed on a 1.2% agarose gel containing formaldehyde. RNA was transferred to Hybond Nylon membrane and the filter was hybridized with a $^{32}$P-labeled oligonucleotide probe specific for A2-G or specific for B9320-G mRNA. Both A2 G specific and B9320 G specific transcripts were detected in the rRSVA2 (B-G) infected cells. The run-off RNA transcript (G-M2) from rRSV A2 (B-G) infected cells is also indicated.

Figure 7:
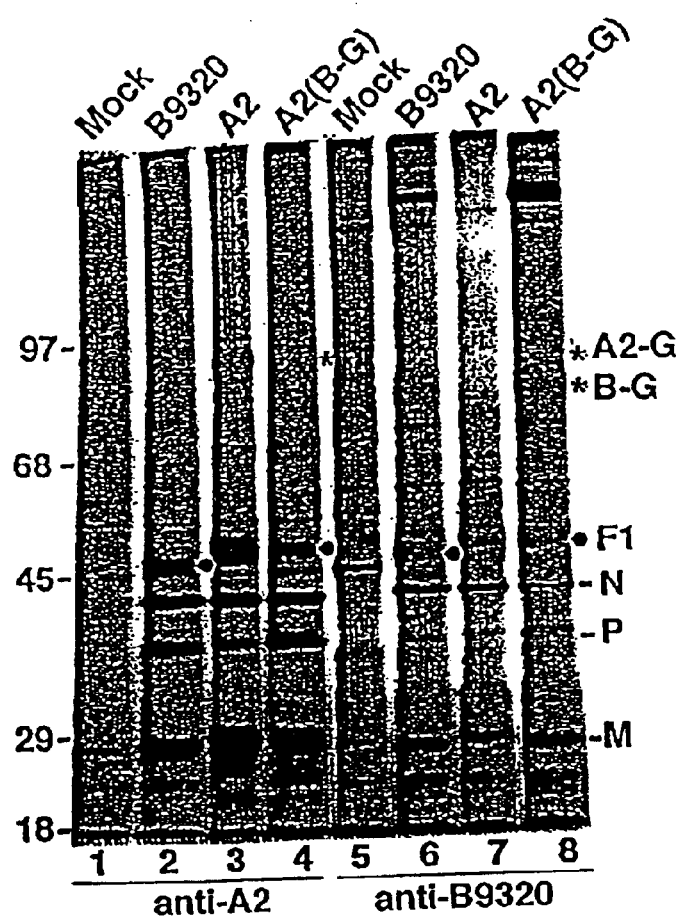

FIG. 7. Analysis of protein expression by rRSVA2 (B-G). Hep-2 cells were mock-infected (lanes 1, 5), infected with RSV B9320 (lanes 2, 6), rRSVA2 (lanes 3, 7) and rRSV A2 (B-G) (lanes 4, 8). At 14–18 hr postinfection, infected cells were labeled with $^{35}$S-promix and polypeptides were immunoprecipitated by goat polyclonal antiserum against RSV A2 strain (lanes 1–5) or by mouse polyclonal antiserum against RSV B9320 strain (lanes 5–8). Immunoprecipitated polypeptides were separated on a 10% polyacrylamide gel. Both RSV A2 specific G protein and RSV B9320 specific G protein were produced in rRSV A2 (B-G) infected cells. The G protein migration is indicated by *. Mobility of the F1 glycoprotein, and N, P, and M is indicated. Molecular sizes are shown on the left in kilodaltons.

Figure 8:
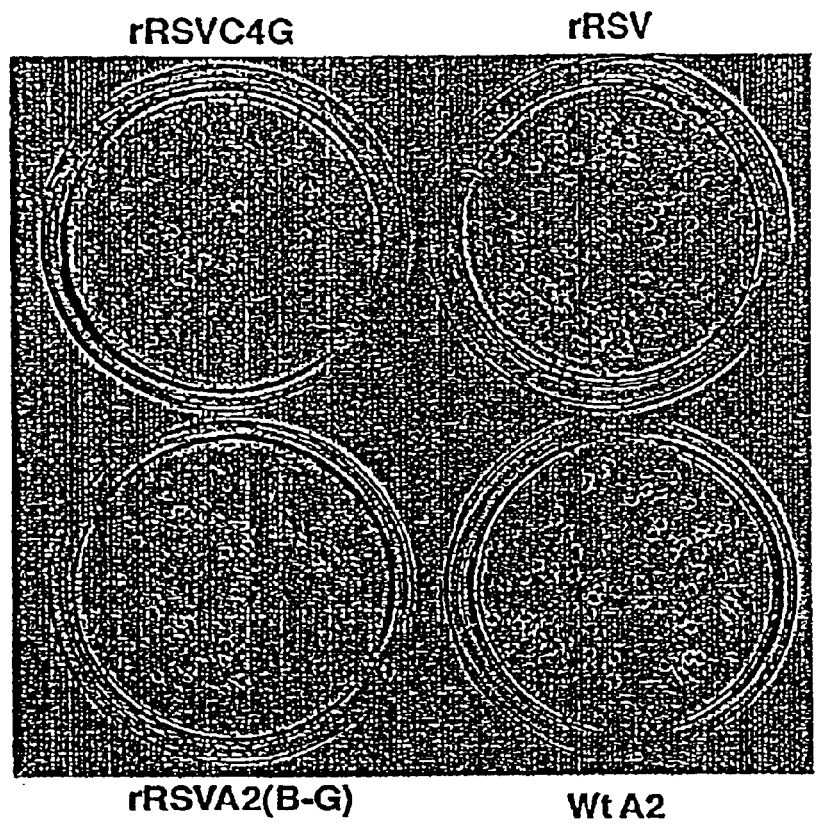

FIG. 8. Plaque morphology of rRSV, rRSVC4G, rRSVA2 (B-G) and wild-type A2 virus (wt A2). Hep-2 cells were infected with each virus and incubated at 35° C. for six days. The cell monolayers were fixed, visualized by immunostaining, and photographed.

Figure 9:
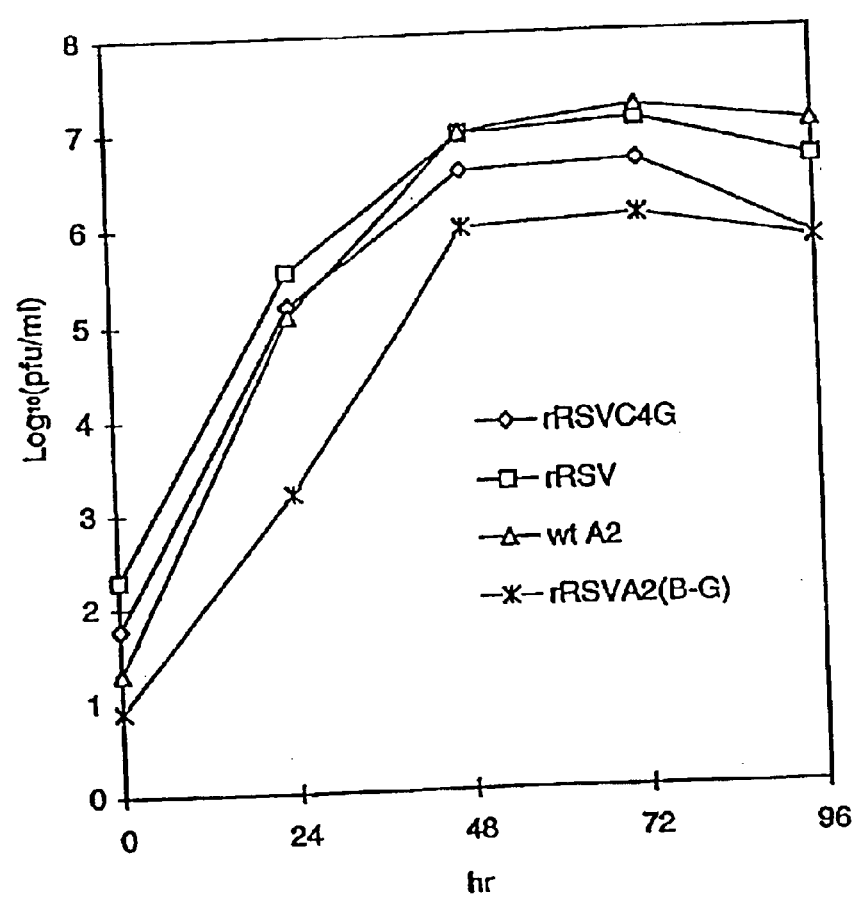

FIG. 9. Growth curve of rRSV, rRSVC4G, wild-type A2 RSV (wt A2) and chimeric rRSVA2(B-G). Hep-2 cells were infected with either virus at a moi of 0.5 and the medium was harvested at 24 hr intervals. The titer of each virus was determined in duplicate by plaque assay on Hep-2 cells and visualized by immunostaining.

FIG. 10. RSV L protein charged residue clusters targeted for site-directed mutagenesis (SEQ ID NO:29). Contiguous charged amino acid residues in clusters were converted to alanines by site-directed mutagenesis (SEQ ID NO:30) of the RSV L gene using the QuikChange site-directed mutagenesis kit (Stratagene).

FIG. 11. RSV L protein cysteine residues targeted for site-directed mutagenesis. Cysteine residues were converted to alanine-residues by site-directed mutagenesis of the RSV L gene using the QuikChange site-directed mutagenesis kit (Stratagene).

FIGS5. 12A–B. Identification RSV M2-2 and SH deletion mutants. Deletions in M2-2 were generated by Hind III digestion of pET(S/B) followed by recloning of a remaining Sac I to BamHI fragment into a full-length clone. Deletions in SH were generated by Sac I digestion of pET(A/S) followed by recloning of a remaining Avr II Sac I fragment into a full-length clone. FIG. 12A. Identification of the recovered rRSVΔSH and rRSVAM2-2 was performed by RT/PCR using primer pairs specific for the SH gene or M2-2 gene, respectively. FIG. 12B rRSVΔSHΔM2-2 was also detected by RT/PCR using primer pairs specific for the M2-2 and SH genes. RT/PCR products were run on an ethidium bromide agarose gel and bands were visualized by ultraviolet (UV) light.

FIGS. 13A–B. Structure of rA2ΔM2-2 genome and recovery of rA2ΔM2-2. (A). Sequences shown is the region of the M2 gene that M2-1 and M2-2 open reading frames overlap. Total of 234 nt that encode the C-terminal 78 amino acids of M2-2 was deleted through the introduced Hind III sites (underlined). The N-terminal 12 amino acid residues of the M2-2 open reading frame (SEQ ID NO:49) are maintained as it overlaps with the M2-1 gene (SEQ ID NO:48). (B). RT/PCR products of rA2ΔM2-2 and rA2 viral RNA using primers V1948 and V1581 in the presence (+) or absence (−) of reverse transcriptase (RT). The size of the DNA product derived from rA2 or rA2ΔM2-2 is indicated.

Figure 14:
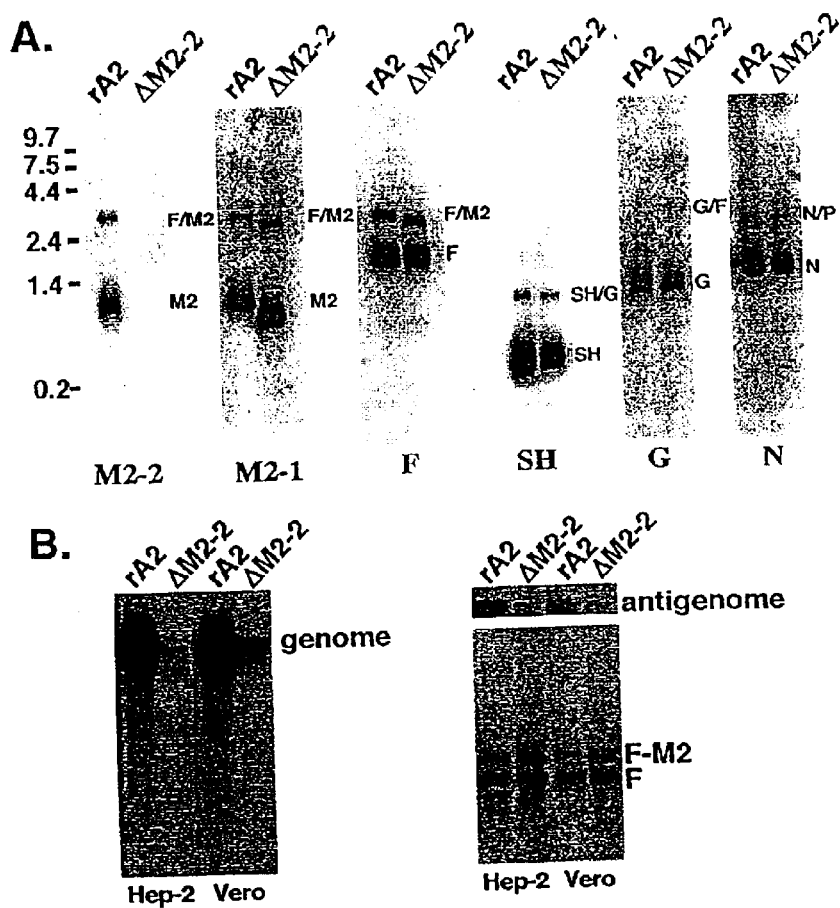

FIGS. 14A–B. Viral RNA expression by rA2ΔM2-2 and rA2. (A). Total RNA was extracted from rA2 or rA2ΔM2-2 infected Vero cells at 48 hr postinfection, separated by electrophoresis on 1.2% agarose/2.2 M formaldehyde gels and transferred to nylon membranes. Each blot was hybridized with a Dig-labeled riboprobe specific for the M2-2, M2-1, F, SH, G or N gene. The size of the RNA marker is indicated on the left. (B). Hep-2 and Vero cells were infected with rA2 or rA2ΔM2-2 for 24 hr and total cellular RNA was extracted. RNA Northern blot was hybridized with a $^{32}$P-labeled riboprobe specific to the negative sense F gene to detect viral genomic RNA or a $^{32}$P-labeled riboprobe specific to the positive sense F gene to detect viral antigenomic RNA and F mRNA. The top panel of the Northern blot on the right was taken from the top portion of the gel shown in the lower panel and was exposed for 1 week to show antigenome. The lower panel of the Northern blot was exposed for 3 hr to show the F mRNA. The genome, antigenome, F mRNA and dicistronic F-M2 RNA are indicated.

Figure 15:
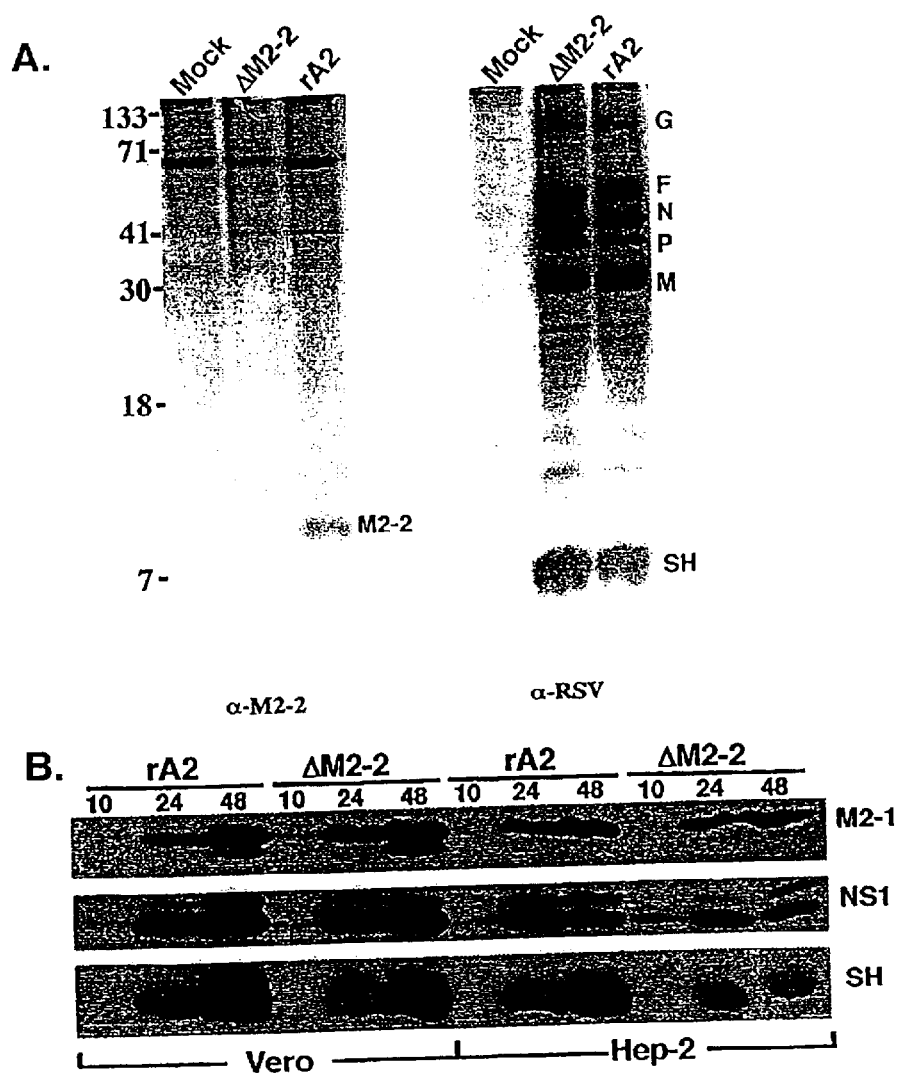

FIGS. 15A–B. Viral protein expression in rA2 ΔM2-2 and rA2 infected cells. (A). Mock-infected, rA2ΔM2-2 and rA2 infected Vero cells were metabolically labeled with $^{35}$S-promix (100 $\mu$Ci/ml) between 14 to 18 hr postinfection. Cell lysates were prepared for immunoprecipitation with goat polyclonal anti-RSV or rabbit polyclonal anti-M2-2 antisera Immunoprecipitated polypeptides were separated on a 17.5% polyacrylamide gel containing 4 M urea and processed for autoradiography. The positions of each viral protein are indicated on the right and the molecular weight size markers are indicated on the left. (B). Protein synthesis kinetics in Hep-2 and Vero cells by Western blotting. Hep-2 and Vero cells were infected with rA2 or rA2ΔM2-2 and at 10 hr, 24 hr, or 48 hr postinfection, total infected cellular polypeptides were separated on a 17.5% polyacrylamide gel containing 4 M urea. Proteins were transferred to a nylon membrane and the blot probed with polyclonal antisera against M2-1, NS1 or SH as indicated.

Figure 16:
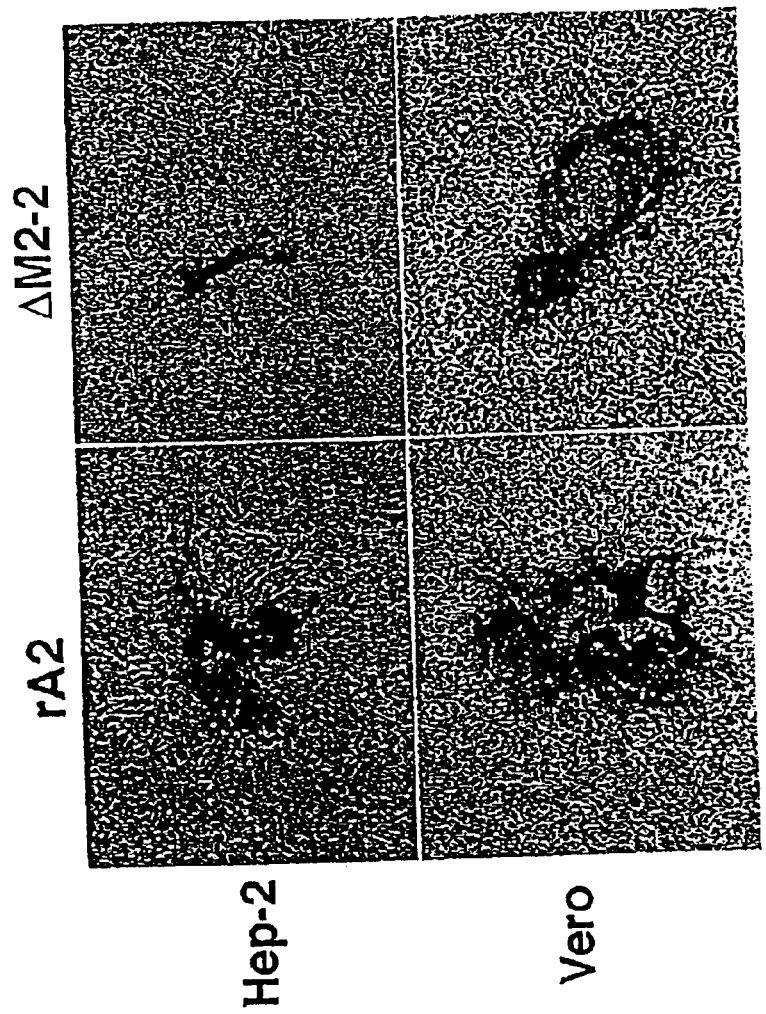

FIG. 16. Plaque morphology of rA2ΔM2-2 and rA2. Hep-2 or Vero cells were infected with rA2ΔM2-2 or rA2 under semisolid overlay composed of 1% methylcellulose and 1×L15 medium containing 2% FBS for 5 days. Virus plaques were visualized by immunostaining with a goat polyclonal anti-RSV antiserum and photographed under microscope.

Figure 17:
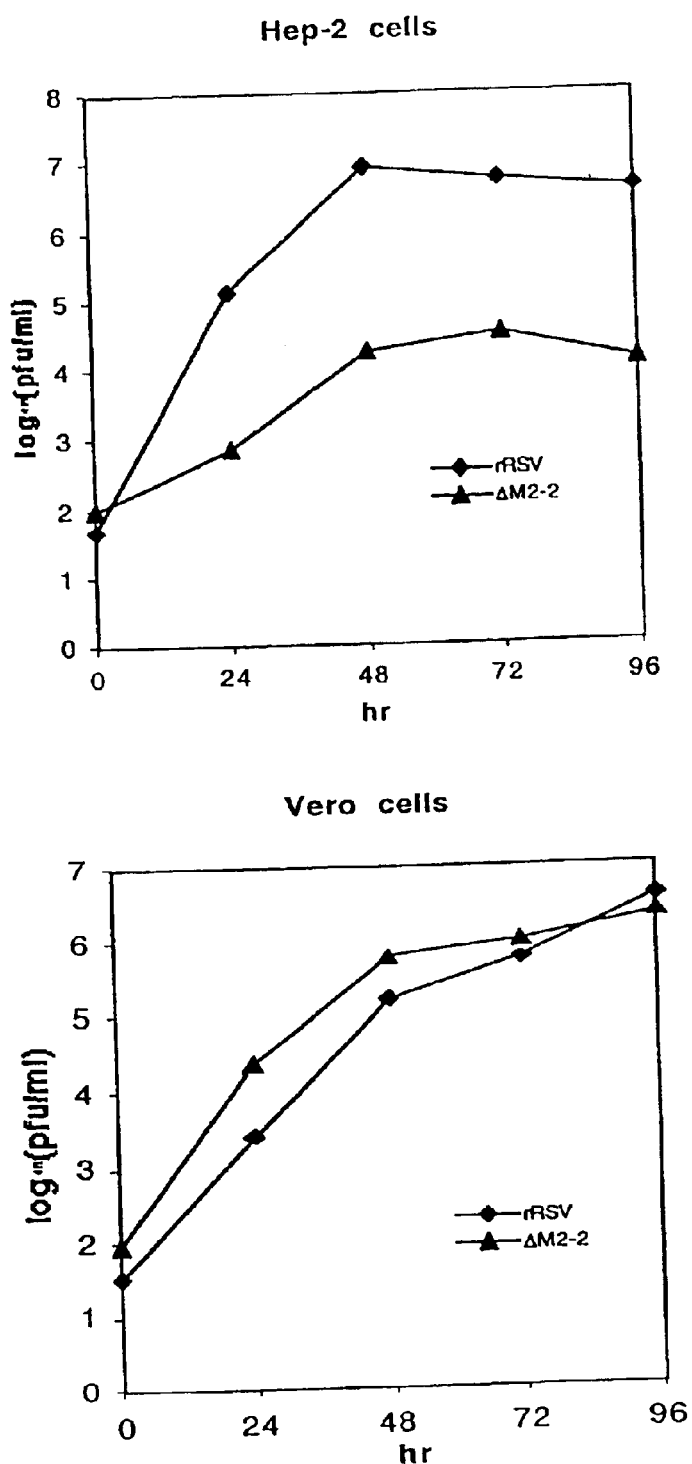

FIG. 17. Growth curves of rA2ΔM2-2 in Hep-2 and Vero cells. Vero cells (A) or Hep-2 cells (B) were infected with rA2ΔM2-2 or rA2 at m.o.i. of 0.5, and aliquots of medium were harvested at 24 hr intervals as indicated. The virus titers were determined by plaque assay in Vero cells. Virus titer at each time point is average of two experiments.

Figure 18:
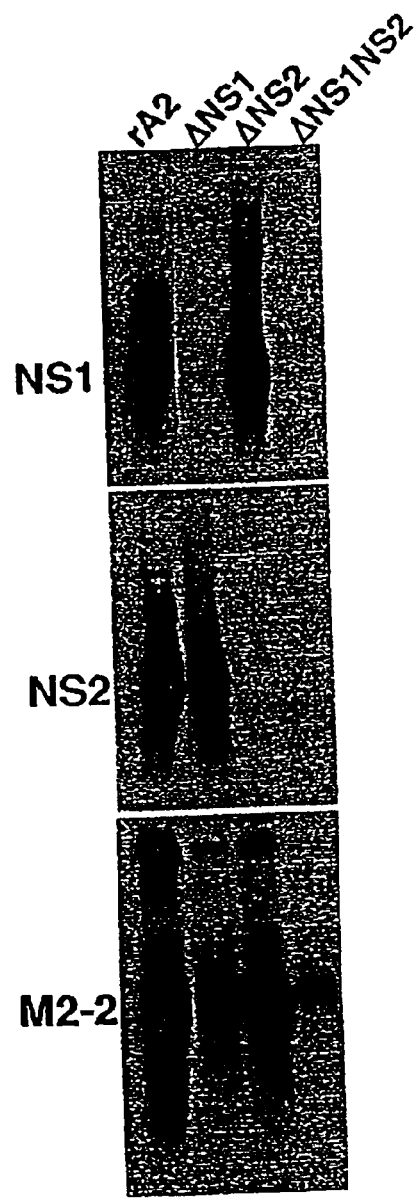

FIG. 18. Northern blot analysis of rA2ΔNS1, rA2ΔNS2 and rA2ΔNS1ΔNS2. Total cellular RNA was extracted from rA2, rA2ΔNS1, rA2ΔNS2 and rA2ΔNS1ΔNS2 infected Vero cells at 24 hr postinfection, separated by electrophoresis on 1.2% agarose/2.2 M formaldehyde gels and transferred to nylon membranes. Each blot was hybridized with a Dig-labeled riboprobe specific for the NS1, NS2, or M2-2 gene as indicated.

Figure 19:
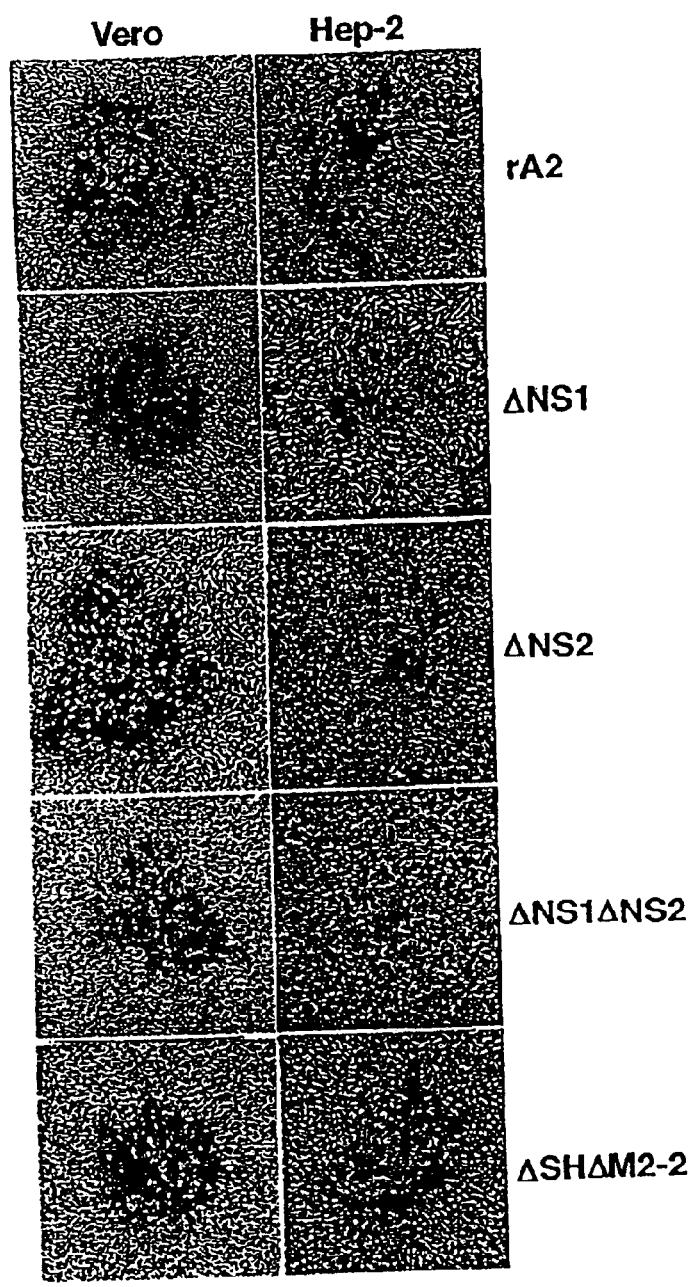

FIG. 19. Plaque morphology of deletion mutants. Hep-2 or Vero cells were infected with each deletion mutant as indicated under semisolid overlay composed of 1% methylcellulose and 1×L15 medium containing 2% FBS for 6 days. Virus plaques were visualized by immunostaining with a goat polyclonal anti-RSV antiserum and photographed under microscope.

Figure 20:
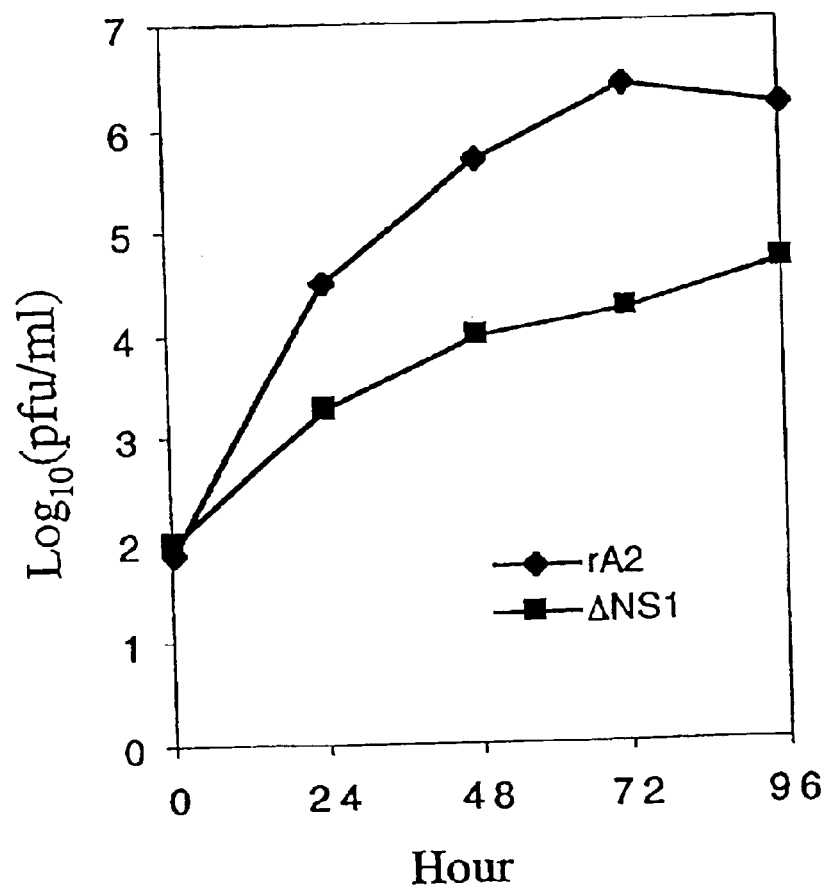

FIG. 20. Growth curves of rA2ΔNS1 in Vero cells. Vero cells were infected with rA2 ΔNS1 or rA2 at m.o.i. of 0.5, and aliquots of medium were harvested at 24 hr intervals as indicated. The virus titers were determined by plaque assay in Vero cells.

Figure 21:
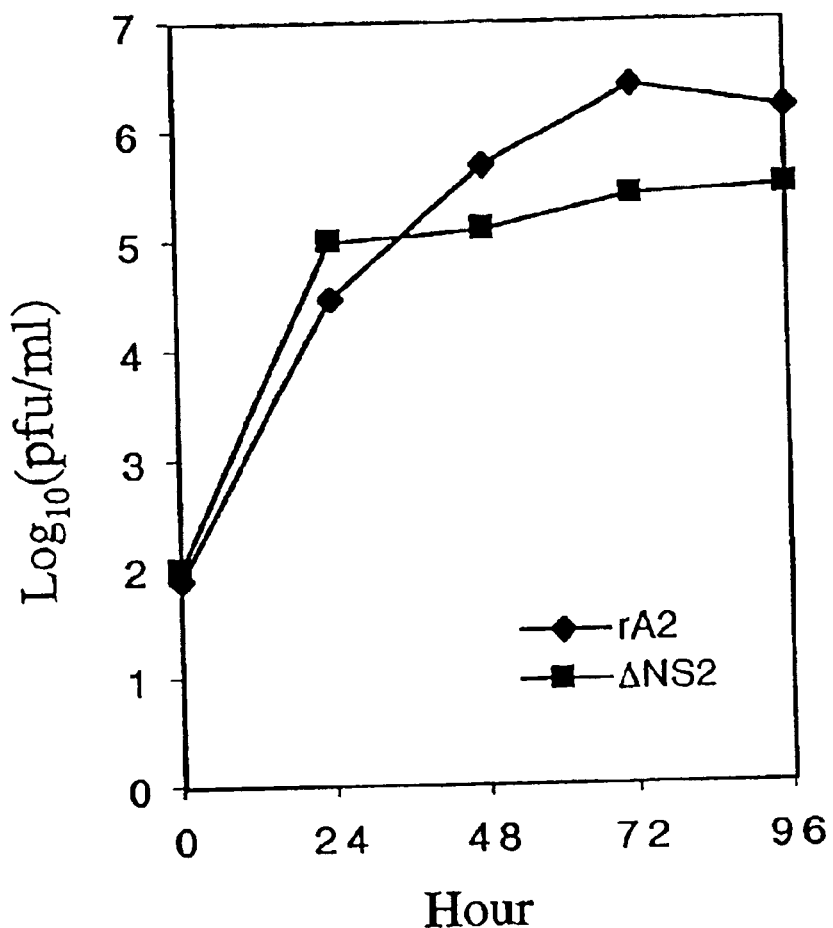

FIG. 21. Growth curves of rA2ΔNS2 in Vero cells. Vero cells were infected with rA2 ΔNS2 or rA2 at m.o.i. of 0.5, and aliquots of medium were harvested at 24 hr intervals as indicated. The virus titers were determined by plaque assay in Vero cells.

Figure 22:
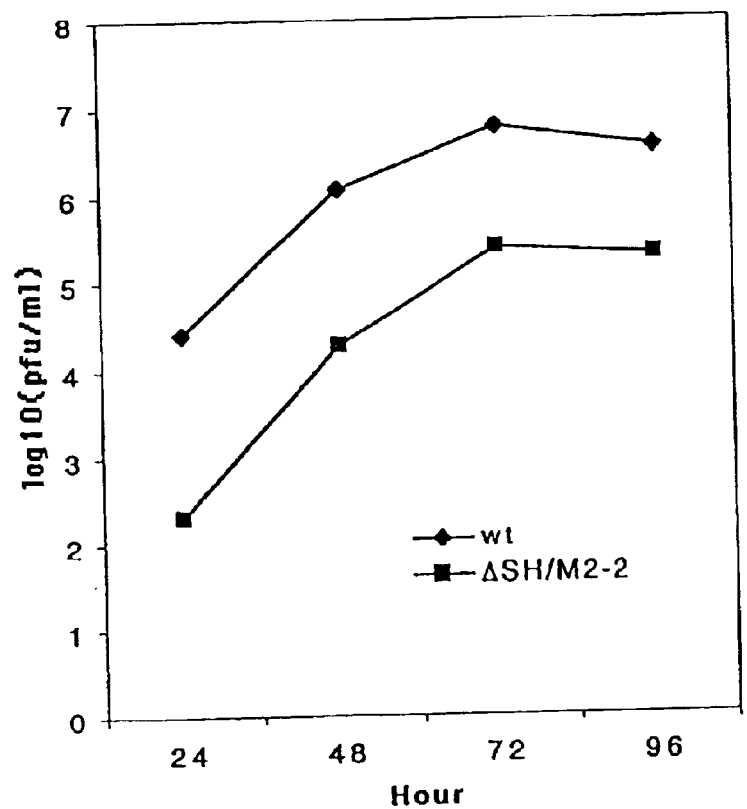

FIG. 22. Growth curves of rA2ΔSHΔM2-2 in Vero cells. Vero cells were infected with rA2ΔSHΔM2-2 or rA2 at m.o.i. of 0.5, and aliquots of medium were harvested at 24 hr intervals as indicated. The virus titers were determined by plaque assay in Vero cells.

Figure 23:
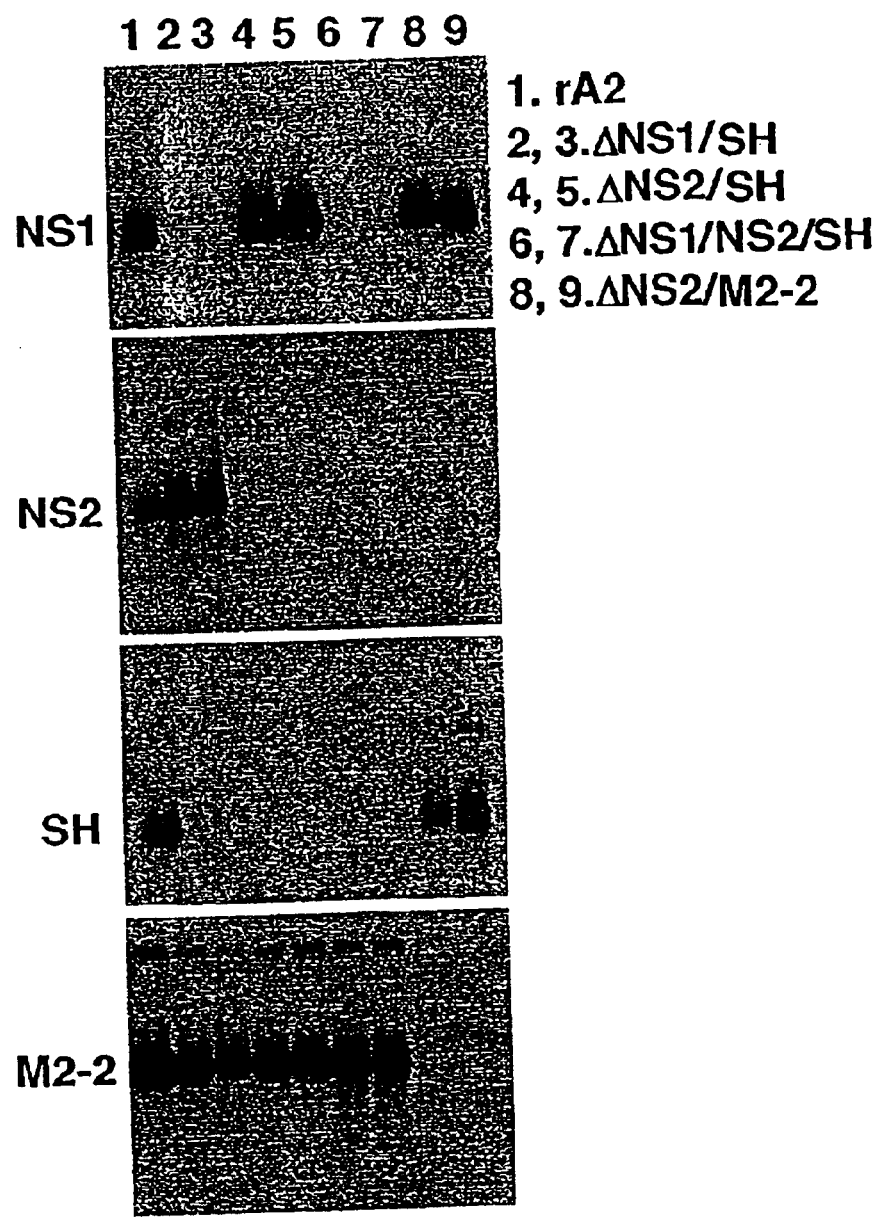

FIG. 23. Northern blot analysis of several deletion mutants. Total cellular RNA was extracted from Vero cells infected with each deletion mutant as indicated at 24 hr postinfection, separated by electrophoresis on 1.2% agarose/ 2.2 M formaldehyde gels and transferred to nylon membranes. Each blot was hybridized with a Dig-labeled riboprobe specific for the NS 1, NS2, SH or M2-2 gene as indicated.

Figure 24:
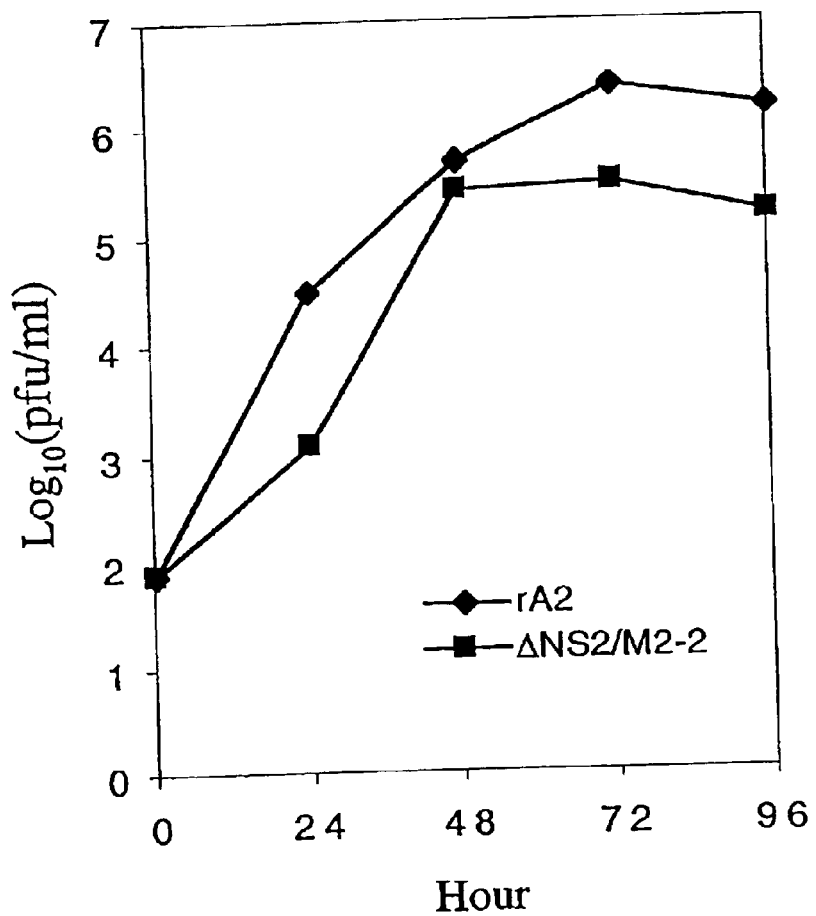

FIG. 24. Growth curves of rA2ΔNS2ΔM2-2 in Vero cells. Vero cells were infected with rA2ΔNS2ΔM2-2 or rA2 at m.o.i. of 0.5, and aliquots of medium were harvested at 24 hr intervals as indicated. The virus titers were determined by plaque assay in Vero cells.

Figure 25:
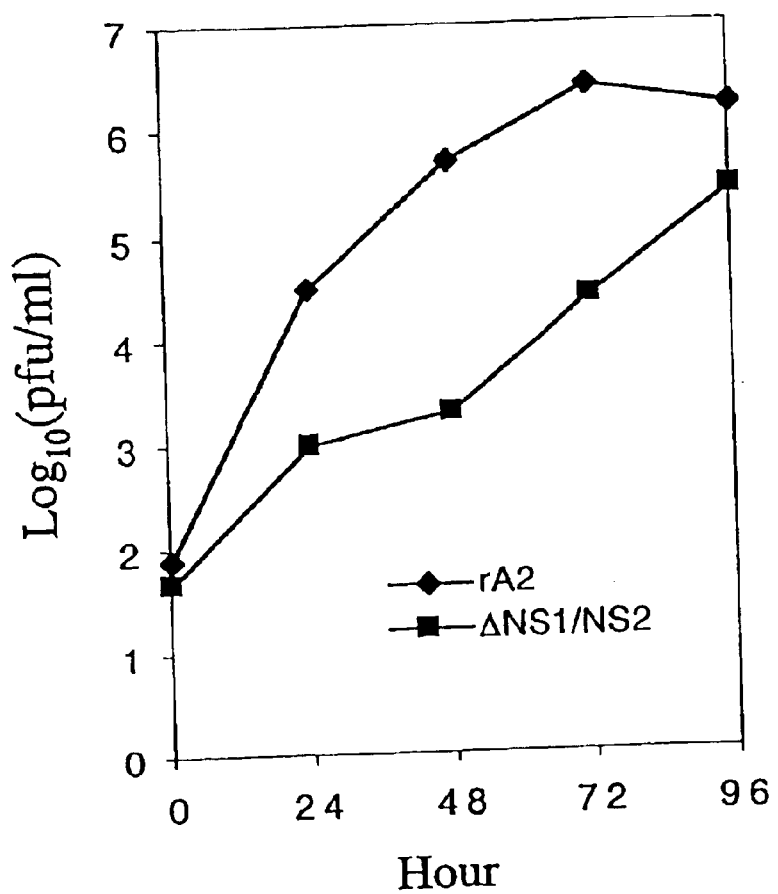

FIG. 25. Growth curves of rA2ΔNS1ΔNS2 in Vero cells. Vero cells were infected with rA2ΔNS1ΔNS2 or rA2 at m.o.i. of 0.5, and aliquots of medium were harvested at 24 hr intervals as indicated. The virus titers were determined by plaque assay in Vero cells.

5. DESCRIPTION OF THE INVENTION

The present invention relates to genetically engineered recombinant RS viruses and viral vectors which express heterologous genes or mutated RS viral genes or a combination of viral genes derived from different strains of RS virus. The invention relates to the construction and use of recombinant negative strand RS viral RNA templates which may be used with viral RNA-directed RNA polymerase to express heterologous gene products in appropriate host cells and/or to rescue the heterologous gene in virus particles. The RNA templates of the present invention may be prepared by transcription of appropriate DNA sequences using a DNA-directed RNA polymerase such as bacteriophage T7, T3 or Sp6 polymerase. The recombinant RNA templates may be used to transfect continuous/transfected cell lines that express the RNA-directed RNA polymerase proteins allowing for complementation.

The invention is demonstrated by way of working examples in which infectious RSV is rescued from CDNA containing the RSV genome in the genomic or antigenomic sense introduced into cells expressing the N, P, and L proteins of the RSV polyrnerase complex. The working examples further demonstrate that expression of M2-1 expression plasmid is not required for recovery of infectious RSV from cDNA which is contrary to what has been reported earlier (Collins et al., 1995, Proc. Natl. Acad. Sci. USA 92:11563–7). Furthermore, the deletion of the M2-ORF2 from recombinant RSV cDNA results in the rescue of attenuated RSV particles. M2-2-deleted-RSV is an excellent vehicle to generate chimeric RSV encoding heterologous gene products, these chimeric viral vectors and rescued virus particles have utility as expression vectors for the expression of heterologous gene products and as live attenuated RSV vaccines expressing either RSV antigenic polypeptides or antigenic polypeptides of other viruses.

The invention is further demonstrated by way of working examples in which a cDNA clone which contained the complete genome of RSV, in addition to a T7 promoter, a hepatitis delta virus ribozyme and a T7 terminator, is used to generate an infectious viral particle when co-transfected with expression vectors encoding the N, P, L proteins of RSV. In addition, the working examples describe RNA transcripts of cloned DNA containing the coding region—in negative sense orientation—of the chloramphenicol-acetyl-transferase (CAT) gene or the green fluorescent protein (GFP) gene flanked by the 5' terminal and 3' terminal nucleotides of the RSV genome. The working examples further demonstrate that an RSV promoter mutated to have increased activity resulted in rescue of infectious RSV particles from a full length RSV cDNA with high efficiency. These results demonstrate the successful use of recombinant viral negative strand templates and RSV polymerase with increased activity to rescue RSV. This system is an excellent tool to engineer RSV viruses with defined biological properties, e.g. live-attenuated vaccines against RSV, and to use recombinant RSV as an expression vector for the expression of heterologous gene products.

This invention relates to the construction and use of recombinant negative strand viral RNA templates which may be used with viral RNA-directed RNA polymerase to express heterologous gene products in appropriate host cells, to rescue the heterologous gene in virus particles and/or express mutated or chimeric recombinant negative strand viral RNA templates (see U.S. Pat. No. 5,166,057 to Palese et al., incorporated herein by reference in its entirety). In a specific embodiment of the invention, the heterologous gene product is a peptide or protein derived from another strain of the virus or another virus. The RNA templates may be in the positive or negative-sense orientation and are prepared by transcription of appropriate DNA sequences using a DNA-directed RNA polymerase such as bacteriophage T7, T3 or the Sp6 polymerase.

The ability to reconstitute RNP's in vitro allows the design of novel chimeric influenza and RSV viruses which express foreign genes. One way to achieve this goal involves modifying existing viral genes. For example, the G or F gene may be modified to contain foreign sequences, such as the HA gene of influenza in its external domains. Where the heterologous sequence are epitopes or antigens of pathogens, these chimeric viruses may be used to induce a protective immune response against the disease agent from which these determinants are derived. For example, a chimeric RNA may be constructed in which a coding sequence derived from the gp 120 coding region of human immunodeficiency virus was inserted into the coding sequence of RSV, and chimeric virus produced from transfection of this chimeric RNA segment into a host cell infected with wild-type RSV.

In addition to modifying genes coding for surface proteins, genes coding for nonsurface proteins may be altered. The latter genes have been shown to be associated with most of the important cellular immune responses in the RS virus system. Thus, the inclusion of a foreign determinant in the G or F gene of RSV may—following infection—induce an effective cellular immune response against this determinant. Such an approach may be particularly helpful in situations in which protective immunity heavily depends on the induction of cellular immune responses (e.g., malaria, etc.).

The present invention also relates to attenuated recombinant RSV produced by introducing specific mutations in the genome of RSV which results in an amino acid change in an RSV protein, such as a polymerase protein, which results in an attenuated phenotype.

The present invention also further relates to the generation of attenuated recombinant RSV produced by introducing specific deletions of viral accessory gene(s) either singly or in combination. Specifically, the present invention relates to the generation of attenuated recombinant RSV bearing a deletion of either the M2-2, SH, NS1, or NS2 viral accessory gene. Additionally, the present invention specifically relates to the generation of attenuated recombinant RSV bearing a combination deletion of either the M2-2/SH viral accessory genes, the M2-2/NS2 viral accessory genes, the NS1/NS2 viral accessory genes, the NS1/NS2 viral accessory genes, the SHNS1 viral accessory genes, the SH/NS2 viral accessory genes, or the SH/NS1/NS2 viral accessory genes.

The invention is demonstrated by way of the working examples presented herein in which infectious attenuated RSV is rescued from RSV cDNA bearing deletions in the M2-2, SH/NS2, or NS2 viral accessory gene(s) either singly or in combination. Such M2-2, SH, NS1, NS2, M2-2/SH, M2-2/NS2, NS1/NS2, SH/NS1, SH/NS2, or SH/NS1/NS2-deleted RSV represent excellent vehicles for the generation of live attenuated RSV vaccines. Additionally, such M2-2, SH, NS1, NS2, M2-2/SH, M2-2/NS2, NS/NS2, SH/NS1, SH/NS2, or SH/NS1/NS2-deleted RSV represent excellent vehicles for the generation of chimeric RSV encoding heterologous gene products in place of either the M2-2, SH, NS1, NS2, M2-2/SH, M2-NS2NS2, NS1/NS2, SH/NS1, SH/NS2, or SH/NS1/NS2 genes. These chimeric RSV-based viral vectors and rescued infectious attenuated viral particles thus have utility as expression vectors for the expression of heterologous gee products and as live attenuated RSV vaccines expressing either RSV antigenic polypeptides or antigenic polypeptides of heterologous viruses.

The present invention further relates to the generation of attenuated recombinant RSV produced by introducing specific mutations into the M2-1 gene. Specifically, the present invention relates to the generation of attenuated recombinant RSV bearing a mutation of the M2-1 gene introduced by one or more techniques, including, without limitation, cysteine scanning mutagenesis and C-terminal truncations of the M2-1 protein.

5.1. Construction of the Recombinant RNA Templates

Heterologous gene coding sequences flanked by the complement of the viral polymerase binding site/promoter, e.g. the complement of the 3'-RSV termini or the 3'- and 5'-RSV termini may be constructed using techniques known in the art. Heterologous gene coding sequences may also be flanked by the complement of the RSV polymerase binding site/promoter, e.g., the leader and trailer sequence of RSV using techniques known in the art. Recombinant DNA molecules containing these hybrid sequences can be cloned and transcribed by a DNA-directed RNA polymerase, such as bacteriophage T7, T3 or the Sp6 polymerase and the like, to produce the recombinant RNA templates which possess the appropriate viral sequences that allow for viral polymerase recognition and activity.

In a preferred embodiment of the present invention, the heterologous sequences are derived from the genome of another strain of RSV, e.g., the genome of RSV A strain is engineered to include the nucleotide sequences encoding the antigenic polypeptides G and F of RSV B strain, or fragments thereof. In such an embodiment of the invention, heterologous coding sequences from another strain of RSV can be used to substitute for nucleotide sequences encoding antigenic polypeptides of the starting strain, or be expressed in addition to the antigenic polypeptides of the parent strain, so that a recombinant RSV genome is engineered to express the antigenic polypeptides of one, two or more strains of RSV.

In yet another embodiment of the invention, the heterologous sequences are derived from the genome of any strain of influenza virus. In accordance with the present invention, the heterologous coding sequences of influenza may be inserted within a RSV coding sequence such that a chimeric gene product is expressed which contains the heterologous peptide sequence within the RSV viral protein. In either embodiment, the heterologous sequences derived from the genome of influenza may include, but are not limited to HA, NA, PB1, PB2, PA, NS1 or NS2.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within an RSV gene coding sequence such that a chimeric gene product is expressed which contains the heterologous peptide sequence within the influenza viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to, sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

One approach for constructing these hybrid molecules is to insert the heterologous coding sequence into a DNA complement of a RSV genomic RNA so that the heterologous sequence is flanked by the viral sequences required for viral polymerase activity; ie., the viral polymerase binding sitelpromoter, hereinafter referred to as the viral polymerase binding site. In an alternative approach, oligonuclcotides encoding the viral polymerase binding site, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (eg., see, for example, the techniques described by Kunkel, 1985, Proc. Natl. Acad. Sci. U.S.A. 82;488). Variations in polymerase chain reaction (PCR) technology, described infra, also allow for the specific insertion of sequences (ie., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophage T3, T7 or Sp6) and the hybrid sequence containing the heterologous gene and the influenza viral polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase. Sequence requirements for viral polymerase activity and constructs which may be used in accordance with the invention are described in the subsections below.

5.1.1. Insertion of the Heterologous Genes

The gene coding for the L protein contains a single open reading frame. The genes coding for M2 contain two open reading frames for ORF1 and 2, respectively. NS1 and NS2 are coded for by two genes, NS1 and NS2. The G and F proteins, coded for by separate genes, are the major surface glycoproteins of the virus. Consequently, these proteins are the major targets for the humoral immune response after infection. Insertion of a foreign gene sequence into any of these coding regions could be accomplished by either an addition of the foreign sequences to be expressed or by a complete replacement of the viral coding region with the foreign gene or by a partial replacement. The heterologous sequences inserted into the RSV genome may be any length up to approximately 5 kilobases. Complete replacement would probably best be accomplished through the use of PCR-directed mutagenesis.

Alternatively, a bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with RS virus packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology with picornaviral elements. Preferred IRES elements include, but are not limited to the mammalian BiP IRES and the hepatitis C virus IRES.

5.2. Expression of Heterologous Gene Products Using Recombinant RNA Template The recombinant templates prepared as described above can be used in a variety of ways to express the heterologous gene products in appropriate host cells or to create chimeric viruses that express the heterologous gene products. In one embodiment, the recombinant template can be combined with viral polymerase complex purified infra, to produce rRNPs which are infectious. To this end, the recombinant template can be transcribed in the presence of the viral polymerase complex. Alternatively, the recombinant template may be mixed with or transcribed in the presence of viral polymerase complex prepared using recombinant DNA methods (e.g. see Kingsbury et al., 1987, Virology 156:396–403). In yet another embodiment, the recombinant template can be used to transfect appropriate host cells to direct the expression of the heterologous gene product at high levels. Host cell systems which provide for high levels of expression include continuous cell lines that supply viral functions such as cell lines superinfected with RSV, cell lines engineered to complement RSV viral functions, etc. p

5.3. Preparation of Chimeric Negative Strand RNA Virus

In order to prepare chimeric virus, reconstituted RNPs containing modified RSV RNAs or RNA coding for foreign proteins may be used to transfect cells which are also infected with a "parent" RSV virus. Alternatively, the reconstituted RNP preparations may be mixed with the RNPs of wild type parent virus and used for transfection directly. Following transfection, the novel viruses may be isolated and their genomes identified through hybridization analysis. In additional approaches described herein for the production of infectious chimeric virus, rRNPs may be replicated in host cell systems that express the RSV or influenza viral polymerase proteins (es, in virus/host cell expression systems; transformed cell lines engineered to express the polymerase proteins, etc.), so that infectious chimeric virus are rescued; in this instance, helper virus need not be utilized since this function is provided by the viral polymerase proteins expressed. In a particularly desirable approach, cells infected with rRNPs engineered for all eight influenza virus segments may result in the production of infectious chimeric virus which contain the desired genotype; thus eliminating the need for a selection system.

Theoretically, one can replace any one of the genes of RSV, or part of any one of the RSV genes, with the foreign sequence. However, a necessary part of this equation is the ability to propagate the defective virus (defective because a normal viral gene product is missing or altered). A number of possible approaches exist to circumvent this problem.

A third approach to propagating the recombinant virus may involve co-cultivation with wild-type virus. This could be done by simply taking recombinant virus and co-infecting cells with this and another wild-type virus (preferably a vaccine strain). The wild-type virus should complement for the defective virus gene product and allow growth of both the wild-type and recombinant virus. This would be an analogous situation to the propagation of defective-interfering particles of influenza virus (Nayak et al., 1983, In: Genetics of Influenza Viruses, P. Palese and D. W. Kingsbury, eds., Springer-Verlag, Vienna, pp. 255–279). In the case of defective-interfering viruses, conditions can be modified such that the majority of the propagated virus is the defective particle rather than the wild-type virus. Therefore this approach may be useful in generating high titer stocks of recombinant virus. However, these stocks would necessarily contain some wild-type virus.

Alternatively, synthetic RNPs may be replicated in cells co-infected with recombinant viruses that express the RS virus polymerase proteins. In fact, this method may be used to rescue recombinant infectious virus in accordance with the invention. To this end, the RSV virus polymerase proteins may be expressed in any expression vector/host cell system, including, but not limited to, viral expression vectors(e.g., vaccinia virus, adenovirus, baculovirus, etc.) or cell lines that express the polymerase proteins (e.g., see Krystal et al., 1986, Proc. Natl. Acad. Sci. USA 83: 2709–2713).

5.4. Generation of Chimeric Viruses With an Attenuated Phenotype

The methods of present invention may be used to introduce mutations or heterologous sequences to generate chimeric attenuated viruses which have many applications, including analysis of RSV molecular biology, pathogenesis, and growth and infection properties. In accordance with the present invention, mutations or heterologous sequences may be introduced for example into the F or G protein coding sequences, NS1, NS2, M1ORF1, M2ORF2, N, P, or L coding sequences. In yet another embodiment of the present invention, a particular viral gene, or the expression thereof, may be eliminated to generate an attenuated phenotype, e.g., the M ORF may be deleted from the RSV genome to generate a recombinant RSV with an attenuated phenotype. In yet another embodiment, the individual internal genes of human RSV can be replaced by another strains counterpart, or their bovine or murine counterpart. This may include part or all of one or more of the NS1, NS2, N, P, M, SH, M2(ORF1), M2(ORF2) and L genes or the G and F genes.

The RSV genome contains ten mRNAs encoding three transmembrane proteins, G protein, fusion F protein required for penetration, and the small SH protein; the nucleocapsid proteins N, P and L; transcription elongation factor M2 ORF 1; the matrix M protein and two nonstructural proteins, NS1 and NS2. Any one of the proteins may be targeted to generate an attenuated phenotype. Other mutations which may be utilized to result in an attenuated phenotype are insertional, deletional and site directed mutations of the leader and trailer sequences.

In accordance with the present invention, an attenuated RSV exhibits a substantially lower degree of virulence as compared to a wild-type virus, including a slower growth rate, such that the symptoms of viral infection do not occur in an immunized individual.

In accordance with the present invention attenuated recombinant RSV may be generated by incorporating a broad range of mutations including single nucleotide changes, site-specific mutations, insertions, substitutions, deletions, or rearrangements. These mutations may affect a small segment of the RSV genome, e.g., 15 to 30 nucleotides, or large segments of the RSV genome, e g., 50 to 1000 nucleotides, depending on the nature of the mutation. In yet another embodiment, mutations are introduced upstream or downstream of an existing cis-acting regulatory element in order to ablate its activity, thus resulting in an attenuated phenotype.

In accordance with the invention, a non-coding regulatory region of a virus can be altered to down-regulate any viral gene, e.g. reduce transcription of its mRNA and/or reduce replication of vRNA (viral RNA), so that an attenuated virus is produced.

Alterations of non-coding regulatory regions of the viral genome which result in down-regulation of replication of a viral gene, and/or down-regulation of transcription of a viral gene will result in the production of defective particles in each round of replication; i.e. particles which package less than the full complement of viral segments required for a fully infectious, pathogenic virus. Therefore, the altered virus will demonstrate attenuated characteristics in that the virus will shed more defective particles than wild type particles in each round of replication. However, since the amount of protein synthesized in each round is similar for both wild type virus and the defective particles, such attenuated viruses are capable of inducing a good immune response.

The foregoing approach is equally applicable to both segmented and non-segmented viruses, where the down regulation of transcription of a viral gene will reduce the production of its mRNA and the encoded gene product. Where the viral gene encodes a structural protein, e.g., a capsid, matrix, surface or envelope protein, the number of particles produced during replication will be reduced so that the altered virus demonstrates attenuated characteristics; e.g., a titer which results in subclinical levels of infection. For example, a decrease in viral capsid expression will reduce the number of nucleocapsids packaged during replication, whereas a decrease in expression of the envelope protein may reduce the number and/or infectivity of progeny virions. Alternatively, a decrease in expression of the viral enzymes required for replication, e.g., the polymerase, replicase, helicase, and the like, should decrease the number of progeny genomes generated during replication. Since the number of infectious particles produced during replication are reduced, the altered viruses demonstrated attenuated characteristics. However, the number of antigenic virus particles produced will be sufficient to induce a vigorous immune response.

An alternative way to engineer attenuated viruses involves the introduction of an alteration, including but not limited to an insertion, deletion or substitution of one or more amino acid residues and/or epitopes into one or more of the viral proteins. This may be readily accomplished by engineering the appropriate alteration into the corresponding viral gene sequence. Any change that alters the activity of the viral protein so that viral replication is modified or reduced may be accomplished in accordance with the invention.

For example, alterations that interfere with but do not completely abolish viral attachment to host cell receptors and ensuing infection can be engineered into viral surface antigens or viral proteases involved in processing to produce an attenuated strain. According to this embodiment, viral surface antigens can be modified to contain insertions, substitution or deletions of one or more amino acids or epitopes that interfere with or reduce the binding affinity of the viral antigen for the host cell receptors. This approach offers an added advantage in that a chimeric virus which expresses a foreign epitope may be produced which also demonstrates attenuated characteristics. Such viruses are ideal candidates for use as live recombinant vaccines. For example, heterologous gene sequences that can be engineered into the chimeric viruses of the invention include, but are not limited to, epitopes of human immunodeficiency virus (HIV) such as gp 120; hepatitis B virus surface antigen (HBsAg); the glycoproteins of herpes virus (e.g., gD, gE); VP1 of poliovirus; and antigenic determinants of nonviral pathogens such as bacteria and parasites, to name but a few.

In this regard, RSV is an ideal system in which to engineer foreign epitopes, because the ability to select from thousands of virus variants for constructing chimeric viruses obviates the problem of host resistance or immune tolerance encountered when using other virus vectors such as vaccinia. In another embodiment, alterations of viral proteases required for processing viral proteins can be engineered to produce attenuation. Alterations which affect enzyme activity and render the enzyme less efficient in processing should affect viral infectivity, packaging, and/or release to produce an attenuated virus.

In another embodiment, viral enzymes involved in viral replication and transcription of viral genes, e.g., viral polymerases, replicases, helicases, etc. may be altered so that the enzyme is less efficient or active. Reduction in such enzyme activity may result in the production of fewer progeny genomes and/or viral transcripts so that fewer infectious particles are produced during replication.

The alterations engineered into any of the viral enzymes include but are not limited to insertions, deletions and substitutions in the amino acid sequence of the active site of the molecule. For example, the binding site of the enzyme could be altered so that its binding affinity for substrate is reduced, and as a result, the enzyme is less specific and/or efficient. For example, a target of choice is the viral polymerase complex since temperature sensitive mutations exist in all polymerase proteins. Thus, changes introduced into the amino acid positions associated with such temperature sensitivity can be engineered into the viral polymerase gene so that an attenuated strain is produced.

5.4.1. THE RSV L Gene as a Target for Attenuation

In accordance with the present invention, the RSV L gene is an important target to generate recombinant RSV with an attenuated phenotype. The L gene represents 48% of the entire RSV genome. The present invention encompasses generating L gene mutants with defined mutations or random mutations in the RSV L gene. Any number of techniques known to those skilled in the art may be used to generate both defined or random mutations into the RSV L gene. Once the mutations have been introduced, the functionality of the L gene cDNA mutants are screened in vitro using a minigenome replication system and the recovered L gene mutants are then further analyzed in vitro and in vivo.

The following strategies are exemplary of the approaches which may be used to generate mutants with an attenuated phenotype. Further, the following strategies as described below have been applied to the L gene only by way of example and may also be applied to any of the other RSV genes.

One approach to generate mutants with an attenuated phenotype utilizes a scanning mutagenesis approach to mutate clusters of charged amino acids to alanines. This approach is particularly effective in targeting functional domains, since the clusters of charged amino acids generally are not found buried within the protein structure. Replacing the charged amino acids with conservative substitutions, such as neutral amino acids, e.g., alanine, should not grossly alter the structure of the protein but rather, should alter the activity of the functional domain of the protein. Thus, disruption of charged clusters should interfere with the ability of that protein to interact with other proteins, thus making the mutated protein's activity thermosensitive which can yield temperature sensitive mutants.

A cluster of charged amino acids may be arbitrarily defined as a stretch of five amino acids in which at least two or more residues are charged residues. In accordance with the scanning mutagenesis approach all of the charged residues in the cluster are mutated to alanines using site-directed mutagenesis. Due to the large site of the RSV L gene, there are many clustered charged residues. Within the L gene, there are at least two clusters of four contiguous charged residues and at least seventeen clusters of three contiguous charged residues. At least two to four of the charged residues in each cluster may be substituted with a neutral amino acid, e.g., alanine.

In yet another approach to generate mutants with an attenuated phenotype utilizes a scanning mutagenesis approach to mutate cysteines to amino acids, such as glycines or alanines. Such an approach takes advantage of the frequent role of cysteines in intramolecular and intermolecular bond formations, thus by mutating cysteines to another residue, such as a conservative substitution e.g., valine or alanine, or a drastic substitution e.g., aspartic acid, the stability and function of a protein may be altered due to disruption of the protein's tertiary structure. There are approximately thirty-nine cysteine residues present in the RSV L gene.

In yet another approach random mutagenesis of the RSV L gene will cover residues other than charged or cysteines. Since the RSV L gene is very large, such an approach may be accomplished by mutagenizing large cDNA fragments of the L gene by PCR mutagenesis. The functionality of such mutants may be screened by a minigenome replication system and the recovered mutants are then further analyzed in vitro and in vivo.

5.5. Vaccine Formulations Using the Chimeric Viruses

Virtually any heterologous gene sequence may be constructed into the chimeric viruses of the invention for use in vaccines. In a preferred embodiment, the present invention relates to bivalent RSV vaccines which confers protection against RSV-A and RSV-B. To formulate such a vaccine, a chimeric RS virus is used which expresses the antigenic polypeptides of both RSV-A and RSV-B subtypes. In yet another preferred embodiment, the present invention relates to a bivalent vaccine which confers protection against both RSV and influenza. To formulate such a vaccine, a chimeric RS virus is used which expresses the antigenic polypeptides of both RSV and influenza.

Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric influenza virus that may then be used to elicit a vertebrate immune response.

Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In this regard, the use of genetically engineered RSV (vectors) for vaccine purposes may require the presence of attenuation characteristics in these strains. Current live influenza virus vaccine candidates for use in humans are either cold adapted, temperature sensitive, or passaged so that they derive several (six) genes from avian influenza viruses, which results in attenuation. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature-sensitive mutants and reversion frequencies should be extremely low.

Alternatively, chimeric viruses with "suicide" characteristics may be constructed. Such viruses would go through only one or a few rounds of replication in the host. When used as a vaccine, the recombinant virus would go through a single replication cycle and induce a sufficient level of immune response but it would not go further in the human host and cause disease. Recombinant viruses lacking one or more of the essential RS virus genes would not be able to undergo successive rounds of replication. Such defective viruses can be produced by co-transfecting reconstituted RNPs lacking a specific gene(s) into cell lines which permanently express this gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and Corynebacterium parvum.

Many methods may be used to introduce the vaccine formulations described above, these include but are not limited to oral, intradermal, intramuscular, intraperitoneal, intravenous, subcutaneous and intranasal routes. It may be preferable to introduce the chimeric virus vaccine formulation via the natural route of infection of the pathogen for which the vaccine is designed. Where a live chimeric virus vaccine preparation is used, it may be preferable to introduce the formulation via the natural route of infection for influenza virus. The ability of RSV and influenza virus to induce a vigorous secretory and cellular immune response can be used advantageously. For example, infection of the respiratory tract by chimeric RSV or influenza viruses may induce a strong secretory immune response, for example in the urogenital system, with concomitant protection against a particular disease causing agent.

The following sections describe by way of example, and not by limitation, the manipulation of the negative strand RNA viral genomes using RSV as an example to demonstrate the applicability of the methods of the present invention to generate chimeric viruses for the purposes of heterologous gene expression, generating infectious viral particles and attenuated viral particles for the purposes of vaccination.

6. Rescue of Infectious Respiratory Syncytial Viruses (RSV) Using RNA Derived From Specific Recombinant DNAS This example describes a process for the rescue of infectious respiratory syncytial virus (RSV), derived from recombinant cDNAs encoding the entire RSV RNA genome into stable and infectious RSVs, as noted in Section 5 above. The method described may be applied to both segmented and non-segmented RNA viruses, including orthomyxovirus, paramyxovirus, e.g., Sendai virus, parainfluenza virus types 1–4, mumps, newcastle disease virus; morbillivirus, e.g., measles, canine distemper virus, rinderpest virus; pneumovirus, e.g., respiratory syncytial virus; rhabdovirus, e.g., rabies, vesiculovirus, vesicular stomatitis virus; but is described by way of example in terms of RSV. This process can be used in the production of chimeric RSV viruses which can express foreign genes, RSV genes non-native to RSV, including other viral proteins such as the HIV env protein. Another exemplary way to achieve the production of chimeric RSV involves modifying existing, native RSV genes, as is further described. Accordingly, this example also describes the utility of this process in the directed attenuation of RSV pathogenicity, resulting in production of a vaccine with defined, engineered biological properties for use in humans.

The first step of the rescue process involving the entire RSV RNA genome requires synthesis of a full length copy of the 15 kilobase (Kb) genome of RSV strain A2. This is accomplished by splicing together subgenomic double strand cDNAs (using standard procedures for genetic manipulation) ranging in size from 1 kb–3.5 kb, to form the complete genomic cDNA. Determination of the nucleotide sequence of the genomic cDNA allows identification of errors introduced during the assembly process; errors can be corrected by site directed mutagenesis, or by substitution of the error region with a piece of chemically synthesized double strand DNA. Following assembly, the genomic cDNA is positioned adjacent to a transcriptional promoter (e.g., the T7 promoter) at one end and DNA sequence which allows transcriptional termination at the other end, e.g., a specific endonuclease or a ribozyme, to allow synthesis of a plus or minus sense RNA copy of the complete virus genome in vitro or in cultured cells. The leader or trailer sequences may contain additional sequences as desired, such as flanking ribozyme and tandem T7 transcriptional terminators. The ribozyme can be a hepatitis delta virus ribozyme or a hammerhead ribozyme and functions to yield an exact 3' end free of non-viral nucleotides.

In accordance with this aspect of the invention, mutations, substitutions or deletions can be made to the native RSV genomic sequence which results in an increase in RSV promoter activity. Applicants have demonstrated that even an increase in RSV promoter activity greatly enhances the efficiency of rescue of RSV, allowing for the rescue of infectious RSV particles from a full-length RSV cDNA carrying the mutation. In particular, a point mutation at position 4 of the genome (C to G) results in a several fold increase in promoter activity and the rescue of infectious viral particles from a full-length RSV cDNA clone carrying the mutation.

The rescue process utilizes the interaction of full-length RSV strain A2 genome RNA, which is transcribed from the constructed cDNA, with helper RSV subgroup B virus proteins inside cultured cells. This can be accomplished in a number of ways. For example, full-length virus genomic RNA from RSV strain A2 can be transcribed in vitro and transfected into RSV strain B9320 infected cells, such as 293 cells using standard transfection protocols. In addition, in vitro transcribed genomic RNA from RSV strain A2 can be transfected into a cell line expressing the essential RSV strain A2 proteins. (in the absence of helper virus) from stably integrated virus genes.

Alternatively, in vitro transcribed virus genome RNA (RSV strain A2) can also be transfected into cells infected with a heterologous virus (e.g., in particular vaccinia virus) expressing the essential helper RSV strain A2 proteins, specifically the N, P, L and/or M2-ORF1 proteins. In addition the in vitro transcribed genomic RNA may be transfected into cells infected with a heterologous virus, for example vaccinia virus, expressing T7 polymerase, which enables expression of helper proteins from transfected plasmid DNAs containing the helper N, P, and L genes.

As an alternative to transfection of in vitro transcribed genomic RNA, plasmid DNA containing the entire RSV cDNA construct may be transfected into cells infected with a heterologous virus, for example vaccinia virus, expressing the essential helper RSV strain A2 proteins and T7 polymerase, thereby enabling transcription of the entire RSV genomic RNA from the plasmid DNA containing the RSV cDNA construct. The vaccinia virus need not however, supply the helper proteins themselves but only the T7 polymerase; then helper proteins may be expressed from transfected plasmids containing the RSV N, P, and L genes, appropriately positioned adjacent to their own T7 promoters.

When replicating virus is providing the helper function during rescue experiments, the B9320 strain of RSV is used, allowing differentiation of progeny rescue directed against RSV B9320. Rescued RSV strain A2 is positively identified by the presence of specific nucleotide 'marker' sequences inserted in the cDNA copy of the RSV genome prior to rescue.

The establishment of a rescue system for native, i.e., 'wild-type' RSV strain A2 allows modifications to be introduced into the cDNA copy of the RSV genome to construct chimeric RSV containing sequences heterologous in some manner to that of native RSV, such that the resulting rescued virus may be attenuated in pathogenicity to provide a safe and efficacious human vaccine as discussed in Section 5.4 above. The genetic alterations required to cause virus attenuation may be gross (e.g., translocation of whole genes and/or regulatory sequences within the virus genome), or minor (e.g., single or multiple nucleotide substitution(s), addition (s) and/or deletion(s) in key regulatory or functional domains within the virus genome), as further described in detail.

In addition to alteration(s) (including alteration resulting from translocation) of the RSV genetic material to provide heterologous sequence, this process permits the insertion of 'foreign' genes (i.e., genes non-native to RSV) or genetic components thereof exhibiting biological function or antigenicity in such a way as to give expression of these genetic elements; in this way the modified, chimeric RSV can act as an expression system for other heterologous proteins or genetic elements, such as ribozymes, anti-sense RNA, specific oligoribonucleotides, with prophylactic or therapeutic potential, or other viral proteins for vaccine purposes.

6.1. Rescue of the Leader and Trailer Sequences of RSV Strain A2 Using RSV Strain B9320 as Helper Virus 6.1.1. Viruses and Cells Although RSV strain A2 and RSV strain B9320 were used in this Example, they are exemplary. It is within the skill in the art to use other strains of RSV subgroup A and RSV subgroup B viruses in accordance with the teachings of this Example. Methods which employ such other strains are encompassed by the invention.

RSV strain A2 and RSV strain B9320 were grown in Hep-2 cells and Vero cells respectively, and 293 cells were used as host during transfection/rescue experiments. All three cell lines were obtained from the ATCC (Rockville, Md.).

6.1.2. Construction and Functional Analysis of Reporter Plasmids

Plasmid pRSVA2CAT (FIG. 1) was constructed as described below.

The cDNAs of the 44 nucleotide leader and 155 nucleotide trailer components of RSV strain A2 (see Mink et al., Virology 185:615–624 (1991); Collins et al., Proc. Natl. Acad. Sci. 88:9663–9667 (1991)), the trailer component also including the promoter consensus sequence of bacteriophage T7 polymerase, were separately assembled by controlled annealing of oligonucleotides with partial overlapping complementarity (see FIG. 1). The oligonucleotides used in the annealing were synthesized on an Applied Biosystems DNA synthesizer (Foster City, Calif.). The separate oligonucleotides and their relative positions in the leader and trailer sequences are indicated in FIG. 1. The oligonucleotides used to construct the leader were:

1. 5'CGA CGC ATA TTA CGC GAA AAA ATG CGT ACA ACA AAC TTG CAT AAA C (SEQ ID NO:1)
2. 5'CAA AAA AAT GGG GCA AAT AAG AAT TTG ATA AGT ACC ACT TAA ATT TAA CT (SEQ ID NO:2)
3. 5'CTA GAG TTA AAT TTA AGT GGT ACT (SEQ ID NO:3)
4. 5'TAT CAA ATT CTT ATT TGC CCC ATT TTT TTG GTT TAT GCA AGT TTG TTG TA (SEQ ID NO:4)
5. 5'CGC ATT TTT TCG CGT AAT ATG CGT CGG TAC (SEQ ID NO:5)

The oligonucleotides used to construct the trailer were:

1. 5'GTA TTC AAT TAT AGT TAT TAA AAA TTA AAA ATC ATA TAA TTT TTT AAA TA (SEQ ID NO:6)
2. 5'ACT TTT AGT GAA CTA ATC CTA AAG TTA TCA TTT TAA TCT TGG AGG AAT AA (SEQ ID NO:7)
3. 5'ATT TAA ACC CTA ATC TAA TTG GTT TAT ATG TGT ATT AAC TAA ATT ACG AG (SEQ ID NO:8)
4. 5'ATA TTA GTT TTT GAC ACT TTT TTT CTC GTT ATA GTG AGT CGT ATT A (SEQ ID NO:9)
5. 5'AGC TTA ATA CGA CTC ACT ATA ACG A (SEQ ID NO:10)
6. 5'GAA AAA AAG TGT CAA AAA CTA ATA TCT CGT AAT TTA GTT AAT ACA CAT AT (SEQ ID NO:11)
7. 5'AAA CCA ATT AGA TTA GGG TTT AAA TTT ATT CCT CCA AGA TTA AAA TGA TA (SEQ ID NO:12)
8. 5'ACT TTA GGA TTA GTT CAC TAA AAG TTA TTT AAA AAA TTA TAT GAT TTT TA (SEQ ID NO: 13)
9. 5'ATT TTT AAT AAC TAT AAT TGA ATA CTG CA (SEQ ID NO:14)

The complete leader and trailer cDNAs were then ligated to the chloramphenicol-acetyl-transferase (CAT) reporter gene XbaI and PstI sites respectively to form a linear-1 kb RSV/CAT cDNA construct. This cDNA construct was then ligated into the Kpn I and Hind II sites of pUC19. The integrity of the final pRSVA2CAT construct was checked by gel analysis for the size of the XbaI/PstI and KpnI/HindII digestion products. The complete leader and trailer cDNAs were also ligated to the green fluorescent protein (GFP) gene using appropriate restriction enzyme sites to form a linear CDNA construct. The resulting RSV-GFP-CAT is a bicistronic reporter construct which expresses both CAT and GFP.

In vitro transcription of Hga I linearized pRSVA2CAT with bacteriophage T7 polymerase was performed according to the T7 supplier protocol (Promega Corporation, Madison, Wis.). Confluent 293 cells in six-well dishes ($-1\times10^6$ cells per well) were infected with RSV strain B9320 at 1 plaque forming units (p.f.u.) per cell and 1 hour later were transfected with 5–10 μg of the in vitro transcribed RNA from the pRSVA2CAT construct. The transfection procedure followed the transfection procedure of Collins et al., Virology 195:252–256 (1993) and employed Transect/AC™ and Opti-MEM reagents according to the manufacturers specifications (Gibco-BRL, Bethesda, Md.). At 24 hours post-infection the 293 cells were assayed for CAT activity using a standard protocol (Current Protocols in Molecular Biology, Vol. 1, Chapter 9.6.2; Gornan, et al., 1982) Mol. Cell Biol. 2: 1044–1051). The detection of high levels of CAT activity indicated that in vitro transcribed negative sense RNA containing the 'leader' and 'trailer' regions of the RSV A2 strain genome and the CAT gene can be encapsidated, replicated and expressed using proteins supplied by RSV strain B9320 (See FIG. 2). The level of CAT activity observed in these experiments was at least as high as that observed in similar rescue experiments where homologous RSV strain A2 was used as helper virus. The ability of an antigenically distinct subgroup B RSV strain B9320 to support the encapsidation, replication and transcription of a subgroup A RSV strain A2 RNA has to our knowledge hitherto not been formally reported.

6.2. Construction of a cDNA Representing the Complete Genome of RSV

To obtain a template for cDNA synthesis, RSV genomic RNA, comprising 15,222 nucleotides, was purified from infected Hep-2 cells according to the method described by Ward et al., J. Gen. Virol. 64:167–1876 (1983). Based on the published nucleotide sequence of RSV, oligonucleotides were synthesized using an Applied Biosystems DNA synthesizer (Applied Biosystems, Foster City, Calif.) to act as primers for first and second strand cDNA synthesis from the genomic RNA template. The nucleotide sequences and the relative positions of the cDNA primers and key endonuclease sites within the RSV genome are indicated in FIG. 3. The production of cDNAs from virus genomic RNA was carried out according to the reverse transcription/polymerase chain reaction (RT/PCR) protocol of Perkin Elmer Corporation, Norwalk, Conn. (see also Wang et al., (1989) Proc. Natl. Acad. Sci. 86:9717–9721); the amplified cDNAs were purified by electroelution of the appropriate DNA band from agarose gels. Purified DNA was ligated directly into the pCRII plasmid vector (Invitrogen Corp. San Diego), and transformed into either One Shot *E. coli* cells (Invitrogen) or 'SURE' *E. coli* cells (Stratagene, San Diego). The resulting, cloned, virus specific, cDNAs were assembled by standard cloning techniques (Sambrook et al., Molecular Cloning—A Laboratory Manual, Cold Spring Harbor laboratory Press (Cold Spring Harbor, N.Y., 1989) to produce a cDNA spanning the complete RSV genome. The entire cDNA genome was sequenced, and incorrect sequences were replaced by either site-directed mutagenesis or chemically synthesized DNA. Nucleotide substitutions were introduced at bases 7291 and 7294 (with base number 1 being at the start of the genomic RNA 3' end) in the 'F' gene, to produce a novel Stu I endonuclease site, and at positions 7423, 7424, and 7425 (also in the F gene) to produce a novel Pme I site. These changes were designed to act as definitive markers for rescue events. The bacteriophage T7 polymerase and the Hga I endonuclease site were placed at opposite ends of the virus genome cDNA such that either negative or positive sense virus genome RNA can be synthesized in vitro. The cDNAs representing the T7 polymerase promoter sequence and the recognition sequence for Hga I were synthesized on an Applied Biosystems DNA synthesizer and were separately ligated to the ends of the virus genome cDNA, or were added as an integral part of PCR primers during amplification of the terminal portion of the genome cDNA, where appropriate; the latter procedure was used when suitable endonuclease sites near the genome CDNA termini were absent, preventing direct ligation of chemically synthesized T7 promoter/Hga I site cDNA to the genome CDNA. This complete construct (genome cDNA and flanking T7 promoter/Hga I recognition sequence) was then cloned into the Kpn I/Not I sites of the Bluescript II SK phagemid (Stratagene, San Diego) from which the endogenous T7 promoter has been removed by site-directed mutagenesis. RNA transcribed from this complete genome construct may be rescued using RSV subgroup B helper virus to give infectious RSV in accordance with Example 6.1. This basic rescue system for the complete native, i.e., 'wild-type' RSV A2 strain genomic RNA can be employed to introduce a variety of modifications into the cDNA copy of the genome resulting in the introduction of heterologous sequences into the genome. Such changes can be designed to reduce viral pathogenicity without restricting virus replication to a point where rescue becomes impossible or where virus gene expression is insufficient to stimulate adequate immunity.

The following oligonucleotides were used to construct the ribozyme/T7 terminator sequence:

5'GGT*GGCCGGCATGGTCCCAGC (SEQ ID NO:31)
3'CCA CCGGCCGTACCAGGGTCG
CTCGCTGGCGCCGGCTGGGCAACA (SEQ ID NO:32)
GAGCGACCGCGGCCGACCCGTTGT
TTCCGAGGGGACCGTCCCCTCGGT (SEQ ID NO:33)
AAGGCTCCCCTGGCAGGGGAGCCA
AATGGCGAATGGGACGTCGACAGC (SEQ ID NO:34)
TTACCGCTTACCCTGCAGCTGTCG
TAACAAAGCCCGAAGGAAGCT (SEQ ID NO:35)
ATTGTTTCGGGCTTCCTTCGA
GAGTTGCTGCTGCCACCGTTG (SEQ ID NO:36)
CTCAACGACGACGGAGGCAAC
AGCAATAACTAGATAACCTTGGG (SEQ ID NO:37)
TCGTTATTGATCTATTGGAACCC
CCTCTAAACGGGTCTTGAGGGTCT (SEQ ID NO:38)
GGAGATTTGCCCAGAACTCCCAGA
TTTTGCTGAAAGGAGGAACTA (SEQ ID NO:39)
AAAACGACTTTCCTCCTTGAT
TATGCGGCCGCGTCGACGGTA (SEQ ID NO:40)
ATACGCCGGCGEAGCTGCCAT
CCGGGCCCGCCTTCGAAG3'(SEQ ID NO:41)
GGCCCGGGCGGAAGCTTC5'

A cDNA clone containing the complete genome of RSV a T7 promoter, a hepatitis delta virus ribozyme and a T7 terminator was generated. This construct can be used to generate antigenomic RNA or RSV in vivo in the presence of T7 polymerase. Sequence analysis indicated that the plasmid contained few mutations in RSV genome.

6.2.1. Modifications of the RSV Genome

Modifications of the RSV RNA genome can comprise gross alterations of the genetic structure of RSV, such as gene shuffling. For example, the RSV M2 gene can be translocated to a position closer to the 5' end of the genome, in order to take advantage of the known 3' to 5' gradient in virus gene expression, resulting in reduced levels of M2 protein expression in infected cells and thereby reducing the rate of virus assembly and maturation. Other genes and/or regulatory regions may also be translocated appropriately, in some cases from other strains of RSV of human or animal origin. For example, the F gene (and possibly the 'G' gene) of the human subgroup B RSV could be inserted into an otherwise RSV strain A genome (in place of, or in addition to the F and G genes of RSV strain A).

In another approach, the RNA sequence of the RSV viruses N protein can be translocated from its 3' proximal site to a position closer to the 5' end of the genome, again taking advantage of the 3' to 5' gradient in gene transcription to reduce the level of N protein produced. By reducing the level of N protein produced, there would result a concomitant increase in the relative rates of transcription of genes involved in stimulating host immunity to RSV and a concomitant reduction in the relative rate of genome replication. Thus, by translocating the RSV RNA sequence coding for RSV N protein, a chimeric RS virus having attenuated pathogenicity relative to native RSV will be produced.

Another exemplary translocation modification resulting in the production of attenuated chimeric RSV comprises the translocation of the RSV RNA sequence coding for the L protein of RSV. This sequence of the RS virus is believed responsible for viral polymerase protein production. By translocating the RSV sequence coding for L protein from its native 5' terminal location in the native RSV genome to a location at or near the 3' terminus of the genome, a chimeric RSV virus exhibiting attenuated pathogenicity will be produced. Yet another exemplary translocation comprises the switching the locations of the RSV RNA sequences coding for the RSV G and F proteins (i.e., relative to each other in the genome) to achieve a chimeric RSV having attenuated pathogenicity resulting from the slight modification in the amount of the G and F proteins produced. Such gene shuffling modifications as are exemplified and discussed above are believed to result in a chimeric, modified RSV having attenuated pathogenicity in comparison to the native RSV starting material. The nucleotide sequences for the foregoing encoded proteins are known, as is the nucleotide sequence for the entire RSV genome. See McIntosh, Respiratory Syncytial Virus in Virology, 2d Ed. edited by B. N. Fields, D. M. Knipe et al., Raven Press, Ltd. New York, 1990 Chapter 38, pp 1045–1073, and references cited therein.

These modifications can additionally or alternatively comprise localized, site specific, single or multiple, nucleotide substitutions, deletions or additions within genes and/or regulatory domains of the RSV genome. Such site specific, single or multiple, substitutions, deletions or additions can reduce virus pathogenicity without overly attenuating it, for example, by reducing the number of lysine or arginine residues at the cleavage site in the F protein to reduce efficiency of its cleavage by host cell protease (which cleavage is believed to be an essential step in functional activation of the F protein), and thereby possibly reduce virulence. Site specific modifications in the 3' or 5' regulatory regions of the RSV genome may also be used to increase transcription at the expense of genome replication. In addition, localized manipulation of domains within the N protein, which is believed to control the switch between transcription and replication can be made to reduce genome replication but still allow high levels of transcription. Further, the cytoplasmic domain(s) of the G and F glycoproteins can be altered in order to reduce their rate of migration through the endoplasmic reticulum and Golgi of infected cells, thereby slowing virus maturation. In such cases, it may be sufficient to modify the migration of G protein only, which would then allow additional up-regulation of 'F' production, the main antigen involved in stimulating neutralizing antibody production during RSV infections. Such localized substitutions, deletions or additions within genes and/or regulatory domains of the RSV genome are believed to result in chimeric, modified RSV also having reduced pathogenicity relative to the native RSV genome.

6.3. Rescue of a cDNA Representing the Complete Genome of RSV 6.3.1. The Construction and Functional Analysis of Expression Plasmids The RSV, N, P, and L genes encode the viral polymerase of RSV. The function of the RSV M genes is unknown. The ability of RSV, N, P, M, and L expression plasmids to serve the function of helper RSV strain A2 proteins was assessed as described below. The RSV, N, P, L, and M2-1 genes were cloned into the modified PCITE 2a(+) vector (Novagen, Madison, Wis.) under the control of the T7 promoter and flanked by a T7 terminator at it's 3' end. PCITE-2a(+) was modified by insertion of a T7 terminator sequence from PCITE-3a(+) into the Alwn I and Bgl II sites of pCITE-2a (+). The functionality of the N, P, and L expression plasmids was determined by their ability to replicate the transfected pRSVA$_2$CAT. At approximately 80% confluency, Hep-2 cells in six-well plates were infected with MVA at a moi of 5. After 1 hour, the infected cells were transfected with pRSVA$_2$CAT (0.5 mg), and plasmids encoding the N (0.4 mg), P (0.4 mg), and L (0.2 mg) genes using lipofecTACE (Life Technologies, Gaithersburg, M.D.). The transfection proceeded for 5 hours or overnight and then the transfection medium was replaced with fresh MEM containing 2% (fetal bovine serum) FBS. Two days post-infection, the cells were lysed and the lysates were analyzed for CAT activity using Boehringer Mannheim's CAT ELISA kit. CAT activity was detected in cells that had been transfected with N, P, and L plasmids together with pRSVA$_2$CAT. However, no CAT activity was detected when any one of the expression plasmids was omitted. Furthermore, co-transfection of RSV-GFP-CAT with the N, P, and L expression plasmids resulted in expression of both GFP and CAT proteins. The ratios of different expression plasmids and moi of the recombinant vaccinia virus were optimized in the reporter gene expression system.

6.3.2. Recovery of Infectious RSV From the Complete RSV cDNA

Hep-2 cells were infected with MVA (recombinant vaccinia virus expressing T7 polymerase) at an moi of one. Fifty minutes later, ttansfection mixture was added onto the cells. The transfection mixture consisted of 2 μg of N expression vector, 2 μg of P expression vector, 1 μg of L expression vector, 1.25 μg of M2/ORF1 expression vector, 2 μg of RSV genome clone with enhanced promoter, 50 μl of Lipofec-TACE (Life Technologies, Gaithersburg, M.D.) and 1 ml OPTI-MEM. One day later, the transfection mixture was replaced by MEM containing 2% FCS. The cells were incubated at 37° C. for 2 days. The transfection supernatant was harvested and used to infect fresh Hep-2 cells in the presence of 40 μg/ml arac (drug against vaccinia virus). The infected Hep2 cells were incubated for 7 days. After harvesting the P1 supernatant, cells were used for immunostaining using antibodies directed against F protein of RSV A2 strain. Six positively stained loci with visible cell-cell-fusion (typical for RSV infection) were identified. The RNA was extracted from P1 supernatant, and used as template for RT-PCR analysis. PCR products corresponding to F and M2 regions were generated. both products contained the introduced markers. In control, PCR products derived from natural RSV virus lacked the markers.

A point mutation was created at position 4 of the leader sequence of the RSV genome clone (C residue to G) and this genome clone was designated pRSVC4GLwt. This clone has been shown in a reporter gene context to increase the promoter activity by several fold compared to wild-type. After introduction of this mutation into the full-length genome, infectious virus was rescued from the cDNA clone. The rescued recombinant RSV virus formed smaller plaques than the wild-type RSV virus (FIG. 8).

This system allows the rescue mutated RSV. Therefore, it may be an excellent tool to engineer live-attenuated vaccines against RSV and to use RSV vector and viruses to achieve heterologous gene expression. It may be possible to express G protein of type B RSV into the type A background, so the vaccine is capable of protect both type A and type B RSV infection. It may also be possible to achieve attenuation and temperature sensitive mutations into the RSV genome, by changing the gene order or by site-directed mutagenesis of the L protein.

6.4. Use of Monoclonal Antibodies to Differentiate Rescued Virus From Helper Virus In order to neutralize the RSV strain B9320 helper virus and facilitate identification of rescued A2 strain RSV, monoclonal antibodies against RSV strain B9320 were made as follows.

Six BALB/c female mice were infected intranasally (i.n.) with $10^5$ plaque forming units (p.f.u.) of RSV B9320, followed 5 weeks later by intraperitoneal (i.p.) inoculation with $10^6$–$10^7$ pfu of RSV B9320 in a mixture containing 50% complete Freund's adjuvant. Two weeks after i.p. inoculation, a blood sample from each mouse was tested for the presence of RSV specific antibody using a standard neutralization assay (Beeler and Coelingh, J. Virol. 63:2941–2950 (1988)). Mice producing the highest level of neutralizing antibody were then further boosted with $10^6$ p.f.u. of RSV strain B9320 in phosphate buffered saline (PBS), injected intravenously at the base of the tail. Three days later, the mice were sacrificed and their spleens collected as a source of monoclonal antibody producing B-cells. Splenocytes (including B-cells) were teased from the mouse spleen through incisions made in the spleen capsule into 5 ml of Dulbecco's Modified Eagle's Medium (DME). Clumps of cells were allowed to settle out, and the remaining suspended cells were separately collected by centrifugation at 2000×g for 5 minutes at room temperature. These cell pellets were resuspended in 15 ml 0.83 (W/V) $NH_4Cl$, and allowed to stand for 5 minutes to lyse red blood cells. Splenocytes were then collected by centrifugation as before through a 10 ml; cushion of fetal calf serum. The splenocytes were then rinsed in DME, repelleted and finally resuspended in 20 ml of fresh DME. These splenocytes were then mixed with Sp2/0 cells (a mouse myeloma cell line used as fusion partners for the immortalization of splenocytes) in a ratio of 10:1, spleen cells: Sp2/0 cells. Sp2/0 cells were obtained from the ATCC and maintained in DME supplemented with 10% fetal bovine serum. The cell mixture was then centrifuged for 8 minutes at 2000×g at room temperature. The cell pellet was resuspended in 1 ml of 50% polyethylene glycol 1000 mol. wt. (PEG 1000), followed by addition of equal volumes of DME at 1 minute intervals until a final volume of 25 ml was attained. The fused cells were then pelleted as before and resuspended at $3.5 \times 10^6$ spleen cells $ml^1$ in growth medium (50% conditioned medium from SP2/0 cells, 50% HA medium containing 100 ml RPMI 25 ml F.C.S., 100 $\mu$gml gentamicin, 4 ml 50×Hypoxanthine, Thymidine, Aminopterin (HAT) medium supplied as a prepared mixture of Sigma Chem. Co., St. Louis, Mo.). The cell suspension was distributed over well plates (200 $\mu$l well$^{-1}$) and incubated at 37° C., 95 humidity and 5% $CO_2$. Colonies of hybridoma cells (fused splenocytes and Sp2/0 cells) were then subcultured into 24 well plates and grown until nearly confluent; the supernatant growth medium was then sampled for the presence of RSV strain B9320 neutralizing monoclonal antibody, using a standard neutralization assay (Beeler and Coelingh, J. Virol. 63:2941–50 (1988)). Hybridoma cells from wells with neutralizing activity were resuspended in growth medium and diluted to give a cell density of 0.5 cells per 100 $\mu$l and plated out in 96 well plates, 200 $\mu$l per well. This procedure ensured the production of monoclones (i.e. hybridoma cell lines derived from a single cell) which were then reassayed for the production of neutralizing monoclonal antibody. Those hybridoma cell lines which produced monoclonal antibody capable of neutralizing RSV strain B9320 but not RSV strain A2 were subsequently infected into mice, i.p. ($10^6$ cells per mouse). Two weeks after the i.p. injection mouse ascites fluid containing neutralizing monoclonal antibody for RSV strain B9320 was tapped with a 19 gauge needle, and stored at −20° C.

This monoclonal antibody was used to neutralize the RSV strain B9320 helper virus following rescue of RSV strain A2 as described in Section 9.1. This was carried out by diluting neutralizing monoclonal antibody 1 in 50 with molten 0.4% (w/v) agar in Eagle's Minimal Essential Medium (EMEM) containing 1% F.C.S. This mixture was then added to Hep-2 cell monolayers, which had been infected with the progeny of rescue experiments at an m.o.i. of 0.1–0.01 p.f.u. per cell. The monoclonal antibody in the agar overlay inhibited the growth of RSV strain B9320, but allowed the growth of RSV strain A2, resulting in plaque formation by the A2 strain. These plaques were picked using a pasteur pipette to remove a plug a agar above the plaque and the infected cells within the plaque; the cells and agar plug were resuspended in 2 ml of EMEM, 1% FCS, and released virus was plaqued again in the presence of monoclonal antibody on a fresh Hep-2 cell monolayer to further purify from helper virus. The twice plaqued virus was then used to infect Hep-2 cells in 24 well plates, and the progeny from that were used to infect six-well plates at an m.o.i. of 0.1 p.f.u. per cell. Finally, total infected cell RNA from one well of a six-well plates was used in a RT/PCR reaction using first and second strand primers on either side of the 'marker sequences' (introduced into the RSV strain A2 genome to act as a means of recognizing rescue events) as described in Section 6.2 above. The DNA produced from the RT/IPCR reaction was subsequently digested with Stu I and Pme I to positively identify the 'marker sequences' introduced into RSV strain A2 cDNA, and hence to establish the validity of the rescue process.

7. Rescue of Infectious RSV Particles in the Absence of M2 Expression

The following experiments were conducted to compare the efficiencies of rescue of RS virions in the presence and absence of the M2/ORF1 gene. If the M2/ORF1 gene function is not required to achieve rescue of RSV infectious particles, it should be possible to rescue RS virions in the absence of the expression of the M2/ORF1 gene function. In the present analysis, Hep-2 cells which are susceptible to RSV replication, were co-transfected with plasmids encoding the 'N', 'P' and 'L' genes of the viral polymerase of RSV and the cDNA corresponding to the full-length antigenome of RSV, in the presence or absence of plasmid DNA encoding the M2/ORF1 gene, and the number of RSV infectious units were measured in order to determine whether or not the M2/ORF1 gene product was required to rescue infectious RSV particles.

The following plasmids were used in the experiments described below: a cDNA clone encoding the full-length antigenome of RSV strain A2, designated pRSVC4GLwt; and plasmids encoding the N, P, and L polymerase proteins, and plasmid encoding the M2/ORF1 elongation factor, each downstream of a T7 RNA promoter, designated by the name of the viral protein encoded.

pRSVC4GLwt was transfected, together with plasmids encoding proteins N, P and L, into Hep-2 cells which had been pre-infected with a recombinant vaccinia virus expressing the T7 RNA polymerase (designated MVA). In another set of Hep-2 cells, pRSVC4GLwt was co-transfected with plasmids encoding the N, P and L polymerase proteins, and in addition a plasmid encoding the M2 function. Transfection and recovery of recombinant RSV were performed as follows: Hep-2 cells were split in six-well dishes (35 mm per well) 5 hours or 24 hours prior to transfection. Each well contained approximately $1 \times 10^6$ cells which were grown in MEM (minimum essential medium) containing 10% FBS (fetal bovine serum). Monolayers of Hep-2 cells at 70%–80% confluence were infected with MVA at a multiplicity of infection (moi) of 5 and incubated at 35° C. for 60 minutes. The cells were then washed once with OPTI-MEM (Life Technologies) and the medium of each dish replaced with 1 ml of OPTI-MEM and 0.2 ml of the transfection mixture. The transfection mixture was prepared by mixing the four plasmids, pRSVC4GLwt, N, P and L plasmids in a final volume of 0.1 ml OPTI-MEM at amounts of 0.5–0.6 $\mu$g of pRSVC4GLwt, 0.4 $\mu$g of N plasmid, 0.4 $\mu$g of P plasmid, and 0.2 $\mu$g of L plasmid. A second mixture was prepared which additionally included 0.4 $\mu$M2/ORFI plasmid. The plasmid mixtures of 0.1 ml were combined with 0.1 ml of OPTI-MEM containing 10 $\mu$l of lipofecTACE (Life Technologies, Gaithersburg, Md.) to constitute the complete transfection mixture. After a 15 minute incubation at room temperature, the transfection mixture was added to the cells, and one day later this was replaced by MEM containing 2% FBS. Cultures were incubated at 35° C. for 3 days at which time the supernatants were harvested. Cells were incubated at 35° C. since the MVA virus is slightly temperature sensitive and is much more efficient at 35° C.

Three days post-transfection, the transfected cell supernatants were assayed for the presence of RSV infectious units by an immunoassay which would indicate the presence of RSV packaged particles (see Table 1). In this assay, 0.3–0.4 ml of the culture supernatants were passaged onto fresh (uninfected) Hep-2 cells and overlaid with 1% methylcellulose and 1×L15 medium containing 2% FBS. After incubation for 6 days, the supernatant was harvested and the cells were fixed and stained by an indirect horseradish peroxidase method, using a goat anti-RSV antibody which recognizes the RSV viral particle (Biogenesis, Sandown, N.H.) followed by a rabbit anti-goat antibody conjugated to horseradish peroxidase. The antibody complexes that bound to RSV-infected cells were detected by the addition of a AEC-(3-amino-9-ethylcarbazole) chromogen substrate (DAKO) according to the manufacturer's instructions. The RSV plaques were indicated by a black-brown coloration resulting from the reaction between the chromogen substrate and the RSV-antibody complexes bound to the plaques. The number of RSV plaques is expressed as the number of plaque forming units (p.f.u.) per 0.5 ml of transfection supernatant (see Table 1).

Comparisons of the amount of RS virions recovered from the supernatants of transfection dishes in the presence or absence of M2/ORFI are shown in Table 1. The results of four separate experiments demonstrated that the absence of M2/ORF1 from the transfection assay did not diminish the number of infectious units of RSV observed. Thus, the results of these experiments clearly indicate that RSV can be rescued in the absence of the M2/ORF1 from cells transfected only with plasmids encoding the three polymerase proteins, N, P and L, and the cDNA encoding the full-length RSV antigenome. The rescue of true RS virions in the absence of M2/ORF1 was further indicated by the ability to passage the rescued recombinant RSV for up to six passages. Therefore, the production of RSV virions is not dependent on the expression of the M2/ORF1 gene, nor does the inclusion of the M2/ORF1 gene in the transfection assay increase the efficiency of true RSV rescue.

TABLE 1

Production of infectious RSV through plasmid transfection is not dependent on expression of M2ORF1

| | Production of infectious RSV (pfu from 0.5 ml transfection supernatants) | |
|---|---|---|
| Expt. | +M2 0RF1 | −M2 ORF1 |
| 1. | 6, 10(8) | 16, 9(13) |
| 2. | 120, 46, 428(198) | 100, 122, 105(109) |
| 3. | 160, 180(170) | 150, 133(142) |
| 4. | 588, 253, 725(522) | 300, 1000, 110(470) |

Each experiment was done singly, in duplicates or triplicates. The average number of plaque forming units (pfu) from 0.5 ml transfected cell supernatants is shown in the brackets.

8. EXAMPLE

Expression of RSV Subgroup B-G and -F Proteins by RSV A2 STRAIN

The following experiments were conducted to generate a chimeric RSV which expresses the antigenic polypeptides of more than one strain of RSV. Two main antigenic subgroups (A and B) of respiratory syncytial virus (RSV) cause human diseases. Glycoproteins F and G are the two major antigenic determinants of RSV. The F glycoproteins of subgroup A and B viruses are estimated to be 50% related, while the relationship of G glycoproteins is considerably less, about 1–5%. Infection of RSV subgroup A induces either partial or no resistance to replication of a subgroup B strain and vice versa Both subgroup A and subgroup B RSV virus vaccines are needed to protect from RSV infection.

The first approach described herein is to make an infectious chimeric RSV cDNA clone expressing subgroup B antigens by replacing the current infectious RSV A2 cDNA clone G and F region with subgroup B-G and -F genes. The chimeric RSV would be subgroup B antigenic specific. The second approach described herein is to insert subgroup B-G gene in the current A2 cDNA clone so that one virus would express both subgroup A and B specific antigens.

8.1. Substitution of A2 G AND F BY B9320 G and F Genes

RSV subgroup B strain B9320 G and F genes were amplified from B9320 vRNA by RT/PCR and cloned into pCRII vector for sequence determination. BamH I site was created in the oligonucleotide primers used for RT/PCR in order to clone the G and F genes from B9320 strain into A2 antigenomic cDNA (FIG. 4A). A cDNA fragment which contained G and F genes from 4326 nt to 9387 nt of A2 strain was first subcloned into pUC19 (pUCR/H). Bgl II sites were created at positions of 4630 (SH/G intergenic junction) and 7554 (F/M2 intergenic junction), respectively by Quickchange site-directed mutagenesis kit (Stratagene, Lo Jolla, Calif.). B9320 G and F cDNA inserted in pCR.II vector was digested with BamH I restriction enzyme and then subcloned into Bgl II digested pUCR/H which had the A2 G and F genes removed. The cDNA clone with A2 G and F genes replaced by B9320 G and F was used to replace the Xho I to Msc I region of the full-length A2 antigenomic CDNA. The resulting antigenomic cDNA clone was termed pRSVB-GF and was used to transfect Hep-2 cells to generate infectious RSVB-GF virus.

Generation of chimeric RSVB-GF virus was as follows, pRSVB-GF was transfected, together with plasmids encoding proteins N, P, and L, into Hep-2 cells which had been infected with MVA, a recombinant vaccinia virus which expresses the T7 RNA polymerase. Hep-2 cells were split a day before transfection in six-well dishes. Monolayers of Hep-2 cells at 60%–70% confluence were infected with MVA at moi of 5 and incubated at 35° C. for 60 min. The cells were then washed once with OPTI-MEM (Life Technologies, Gaithersburg, Md.). Each dish was replaced with 1 ml of OPTI-MEM and added with 0.2 ml of transfection medium. The transfection medium was prepared by mixing five plasmids in a final volume of 0.1 ml of OPTI-MEM medium, namely 0.6 µg of RSV antigenome pRSVB-GF, 0.4 µg of N plasmid, 0.4 µg of P plasmid, and 0.2 µg of L plasmid. This was combined with 0.1 ml of OPTI-MEM containing 10 µl lipofecTACE (Life Technologies, Gaithersburg, Md. U.S.A.). After a 15 minute incubation at room temperature, the DNA/lipofecTACE was added to the cells and the medium was replaced one day later by MEM containing 2% FBS. Cultures were further incubated at 35° C. for 3 days and the supernatants harvested. Aliquots of culture supernatants were then used to infect fresh Hep-2 cells. After incubation for 6 days at 35° C., the supernatant was harvested and the cells were fixed and stained by an indirect horseradish peroxidase method using goat anti-RSV antibody (Biogenesis, Sandown, N.H.) followed by a rabbit anti-goat antibody linked to horseradish peroxidase. The virus infected cells were then detected by addition of substrate chromogen (DAKO, Carpinteria, Calif. U.S.A.) according to the manufacturer's instructions. RSV-like plaques were detected in the cells which were infected with the supernatants from cells transfected with pRSVB-GF. The virus was further plaque purified twice and amplified in Hep-2 cells.

Recombinant RSVB-GF virus was characterized by RT/PCR using RSV subgroup B specific primers. Two independently purified recombinant RSVB-GF virus isolates were extracted with an RNA extraction kit (Tel-Test, Friendswood, Tex.) and RNA was precipitated by isopropanol. Virion RNAs were annealed with a primer spanning the RSV region from nt 4468 to 4492 and incubated for 1 hr under standard RT conditions (10 µl reactions) using superscript reverse transcriptase (Life Technologies, Gaithersburg, Md.). Aliquots of each reaction were subjected to PCR (30 cycles at 94° C. for 30 s, 55° C. for 30 s and 72° C. for 2 min) using subgroup B specific primers in G region (CACCACCTACCTTACTCAAGT; SEQ ID NO:42) and (TTTGTTTGTGGGTTTGATGGTTGG; SEQ ID NO:43). The PCR products were analyzed by electrophoresis on 1% agarose gel and visualized by staining with ethidium bromide. As shown in FIG. 5, no DNA product was produced in RT/PCR reactions using RSV A2 strain as template. However, a predicted product of 254 bp was detected in RT/PCR reactions utilizing RSVB-GF RNA or the PCR control plasmid, pRSVB-GF DNA, as template, indicating the rescued virus contained G and F genes derived form B9320 virus.

8.2. Expression of B9320G BY RSV A2 Virus

RSV subgroup B strain B9320 G gene was amplified from B9320 vRNA by RT/PCR and cloned into pCRII vector for sequence determination. Two Bgl II sites were incorporated into the PCR primers which also contained gene start and gene end signals (GATATCAAGATCTACAATAACATTGGGGCAAATGC; SEQ ID NO:44) and (GCTAAGAGATCTTTTT GAATAAGCTAAGCATG; SEQ ID NO:45). B9320G cDNA insert was digested with Bgl II and cloned into the SH/G (4630 nt) or F/M2 (7552 nt) intergenic junction of a A2 cDNA subclone (FIG. 4B and FIG. 4C). The Xho I to Msc I fragment containing B9320G insertion either at SH/G or F/M2 intergenic region was used to replace the corresponding Xho I to Msc I region of the A2 antigenomic cDNA. The resulting RSV antigenomic cDNA clone was termed as pRSVB9320G-SH/G or pRSVB9320G-F/M2.

Generation of RSV A2 virus which had B9320 G gene inserted at F/M2 intergenic region was performed similar to what has described for generation of RSVB-GF virus. Briefly, pRSVB9320G-F/M2 together with plasmids encoding proteins N, P and L were transfected, into Hep-2 cells, infected with a MVA vaccinia virus recombinant, which expresses the T7 RNA polymerase (Life Technologies, Gaithersburg, M.D.). The transfected cell medium was replaced by MEM containing 2% fetal bovine serum (FBS) one day after transfection and further incubated for 3 days at 35° C. Aliquots of culture supernatants (PO) were then used to infect fresh Hep-2 cells. After incubation for 6 days at 35° C., the supernatant was harvested and the cells were fixed and stained by an indirect horseradish peroxidase method using goat anti-RSV antibody (Biogenesis) followed by a rabbit anti-goat antibody linked to horseradish peroxidase. The virus infected cells were then detected by addition of substrate chromogen (Dako). RSV-like plaques were detected in the cells which were infected with the supernatants from cells transfected with pRSVB9320G/F/M2.

Figure 6:
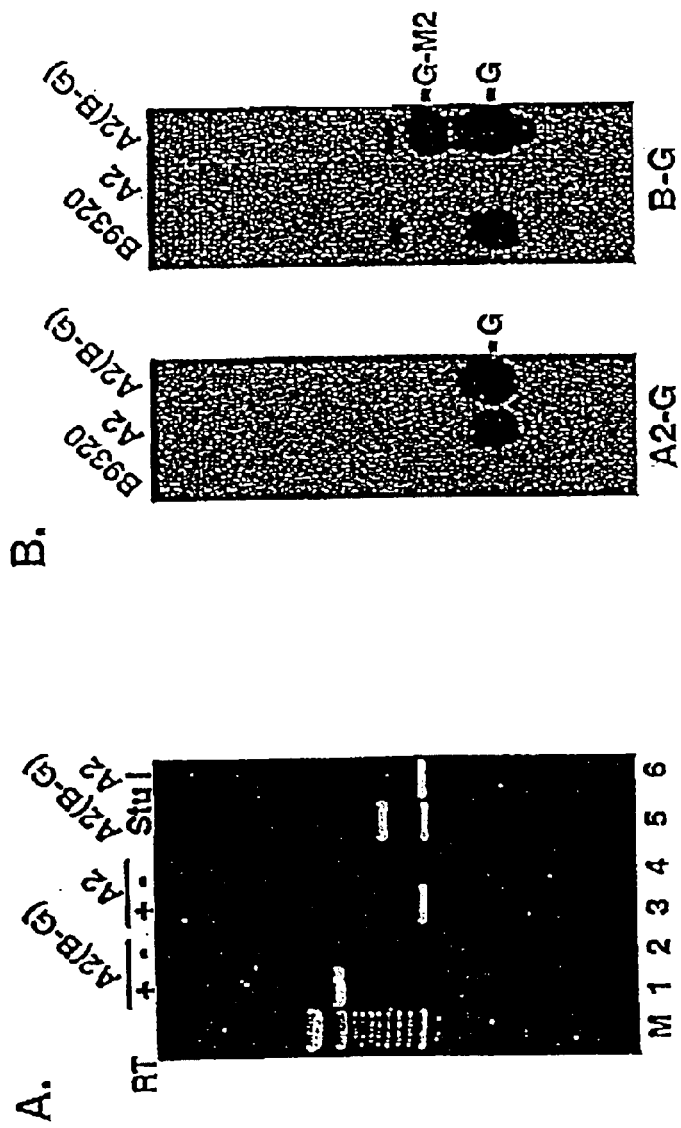

Characterization of pRSVB9320G-F/M2 virus was performed by RT/PCR using B9320G specific primers. A predicted PCR product of 410 bp was seen in RT/PCR sample using pRSVB9320G-F/M2 RNA as template, indicating the rescued virus contained G gene derived from B9320. (FIG. 6)

Expression of the inserted RSV B9320 G gene was analyzed by Northern blot using a $^{32}$P-labeled oligonucleotide specific to A2-G or B-G MRNA. Total cellular RNA was extracted from Hep-2 cells infected with wild-type RSVB 9320, rRSVA2, or rRSVB9320G-F/M2 48 hours postinfection using an RNA extraction kit (RNA stat-60, Tel-Test). RNA as electrophoresed on a 1.2% agarose gel containing formaldehyde and transferred to a nylon membrane (Amersham). An oligonucleotide specific to the G gene of the A2 stain (5'TCTTGACTGTTGTGGA TTGCAGGGTTGACTTGACTCCGATCGATCC-3') (SEQ ID NO:46) and an oligonucleotide specific to the B9320 G gene (5'CTTGTGTTGTTGTTGTATGGTGTGTTT CTGATTTTGTATTGATCGATCC-3') (SEQ ID NO:47) were labeled with $^{32}$P-ATP by a kinasing reaction known to those of ordinary skill in the art. Hybridization of the membrane with one of the $^{32}$P-labeled G gene specific oligonucletodies was performed at 65° C. and washed according to standard procedure. Both A2-G and B9320-G specific RNA were detected in the rRSVB9320G-F/M2 infected Hep-2 Cells. (FIG. 6B) These results demonstrate subtype specific RNA expression.

Protein expression of the chimeric rRSVA2(B-G) was compared to that of RSV B9320 and rRSV by immunoprecipitation of $^{35}$S-labeled infected Hep-2 cell lysates. Briefly, the virus infected cells were labeled with $^{35}$S-promix (100 µCi/ml $^{35}$S-Cys and $^{35}$S-Met, Amersham, Arlington Heights, Ill.) at 14 hours to 18 hours post-infection according to a protocol known to those of ordinary skill in the art. The cell monolayers were lysed by RIPA buffer and the polypeptides were immunoprecipitated with either polyclonal antiserum raised in goat against detergent disrupted RSV A2 virus (FIG. 7, lanes 1–4) or antiserum raised in mice against undisrupted B9320 virions (FIG. 7, lanes 5–8). The radio labeled immunoprecipitated polypeptides were electrophoresed on 10% polyacrylamide gels containing 0.1% SDS and detected by autoradiography. Anti-RSV A2 serum immunoprecipitated the major polypeptides of the RSV A2 strain, whereas anti-B9320 serum mainly reacted with RSV B9320 G protein and the conserved F protein of both A and B subgroups. As shown in FIG. 7, a protein which is identical to the A2-G protein (lane 3), was immunoprecipitated from the rRSVA2(B-G) infected cells (lane 4) by using an antiserum against RSV A2. The G protein of RSV B9320 strain was not recognized by the anti-A2 antiserum. A protein species, smaller than A2-G protein, was immunoprecipitated from both B9320 (lane 6) and rRSV A2(B-G) (lane 9) infected cells using the antiserum raised in mice against B9320 virions. This polypeptide was not present in the uninfected and RSV A2 infected cells and likely is to represent the G protein specific to the RSV B 9320 strain. Amino acid sequence comparison of both A2 and B9320 RSV G proteins indicated that two additional potential N-glycosylation sites (N-X-S/t) are present in the RSV A2G protein, which may contribute to slower migration of the A2 G protein under the conditions used. The F protein of RSV B9320 also migrated slightly faster than RSV A2 F protein. The P and M proteins also showed mobility differences between the two virus subtypes. The identity of the polypeptide near the top of the protein gel present in FSV B9320 and rRSVA2(B-G) infected cells is not known. Antisera raised in mice against the RSV B9320 virions poorly recognized the N, P and M proteins are compared to the goat antiserum raised against the RSV A2 strain. The data described above clearly indicate that chimeric rRSV A2(B-G) expresses both the RSV A2 and B9320 specific G proteins.

8.2.1 Replication of Recombinant RSV in Tissue Culture

Recombinant RS viruses were plaque purified three times and amplified in Hep-2 cells. Plaque assays were performed in Hep-2 cells in 12-well plates using an overlay of 1% methylcellulose and 1×L15 medium containing 2% fetal bovine serum (FBS). After incubation at 35° C. for 6 days, the monolayers were fixed with methanol and plaques were identified by immunostaining. Plaque size and morphology of rRSV was very similar to that of wild-type A2 RSV (FIG. 8). However, the plaques formed by rRSVC4G were smaller than rRSV and wild-type A2 virus. The only genetic difference between rRSV and rRSVC4 was a single nucleotide substitution in the RSV leader region. Therefore, the smaller plaque size of rRSV A2(B-G) was not distinguishable from that of rRSVC4G.

The growth curves of rRSV, rRSVC4G and rRSV A2 (B-G) were compared to that of the biologically derived wild-type A2 virus. Hep-2 cells were grown in T25 culture flasks and infected with rRSV, rRSVC4G, rRSVA2(B-G), or wild-type RSV A2 strain at a moi of 0.5. After 1 hour adsorption at 37° C., the cells were washed three times with MEM containing 2% FBS and incubated at 37° C. in 5% $CO_2$. At 4 hour intervals post-infection, 250 µl of the culture supernatant was collected, and stored at −70° C. until virus titration. Each aliquot taken was replaced with an equal amount of fresh medium. The titer of each virus was determined by plaque assay on Hep-$^2$ cells and visualized by immunostaining (vide supra). As shown in FIG. 9, the growth kinetics of rRSV is very similar to that of wild-type A2 virus. Maximum virus titer for all the viruses were achieved between 48 hr to 72 hr. The virus titer of rRSVC4G was about 2.4-fold (at 48 hr) and 6.6-fold (at 72 hr) lower than rRSV and wild-type A2 RSV. The poor growth of rRSVC4G may also be due to the single nucleotide change in the leader region. The chimeric rRSV A2(B-G) showed slower kinetics and lower peak titer (FIG. 9).

9. EXAMPLE

Generation of RSV L Gene Mutants

The strategy for generating L gene mutants is to introduce defined mutations or random mutations into the RSV L gene. The functionality of the L gene cDNA mutants can be screened in vitro by a minigenome replication system. The recovered L gene mutants are then further analyzed in vitro and in vivo.

9.1 Mutagenesis Strategies 9.1.1 Scanning Mutagenesis to Change the Clustered Charged Amino Acids to Alanine This mutagenesis strategy has been shown to be particularly effective in systematically targeting functional domains exposed on protein surfaces. The rationale is that clusters of charged residues generally do not lie buried in the protein structure. Making conservative substitutions of these charged residues with alanines will therefore remove the charges without grossly changing the structure of the protein. Disruption of charged clusters may interfere with the interaction of RSV L protein with other proteins and make its activity thermosensitive, thereby yielding temperature-sensitive mutants.

A cluster was originally defined arbitrarily as a stretch of 5 amino acids in which two or more residues are charged residues. For scanning mutagenesis, all the charged residues in the clusters can be changed to alanines by site directed mutagenesis. Because of the large size of the RSV L gene, there are many clustered charged residues in the L protein. Therefore, only contiguous charged residues of 3 to 5 amino acids throughout the entire L gene were targeted (FIG. 10). The RSV L protein contains 2 clusters of five contiguous charged residues, 2 clusters of four contiguous charged residues and 17 clusters of three contiguous charge residues. Two to four of the charged residues in each cluster were substituted with alanines.

The first step of the invention was to introduce the changes into pCITE-L which contains the entire RSV L-gene, using a QuikChange site-directed mutagenesis kit (Stratagene). The introduced mutations were then confirmed by sequence analysis.

9.1.2. Cysteine Scanning Mutagenesis

Cysteines are good targets for mutagenesis as they are frequently involved in intramolecular and intermolecular bond formations. By changing cysteines to glycines or alanines, the stability and function of a protein may be altered because of disruption of its tertiary structure. Thirty-nine cysteine residues are present in the RSV L protein (FIG. 11). Comparison of the RSV L protein with other members of paramyxoviruses indicates that some of the cysteine residues are conserved.

Five conserved cysteine residues were changed to either valine (conservative change) or to aspartic acids (nonconservative change) using a QuikChange site-directed mutagenesis kit (Stratagene) degenerate mutagenic oligonucleotides. It will be apparent to one skilled in the art that the sequence of the mutagenic oligonucleotides is determined by the protein sequence desired. The introduced mutations were confirmed by sequence analysis.

9.1.3. Random Mutagenesis

Random mutagenesis may change any residue, not simply charged residues or cysteines. Because of the size of the RSV L gene, several L gene cDNA fragments were mutagenized by PCR mutagenesis. This was accomplished by PCR using exo Pfu polymerase obtained from Strategene. Mutagenized PCR fragments were then cloned into a pCITE-L vector. Sequencing analysis of 20 mutagenized CDNA fragments indicated that 80%–90% mutation rates were achieved. The functionality of these mutants was then screened by a minigenome replication system. Any mutants showing altered polymerase function were then further cloned into the full-length RSV cDNA clone and virus recovered from transfected cells.

9.2. Functional Analysis of RSV L Protein Mutants by Minigenome Replication System The functionality of the L-genes mutants were tested by their ability to replicate a RSV minigenome containing a CAT gene in its antisense and flanked by RSV leader and trailer sequences. Hep-2 cells were infected with MVA vaccinia recombinants expressing T7 RNA polymerase. After one hour, the cells were transfected with plasmids expressing mutated L protein together with plasmids expressing N protein and P protein, and pRSV/CAT plasmid containing CAT gene (minigenome). CAT gene expression from the transfected cells was determined by a CAT ELISA assay (Boehringer Mannheim) according to the manufacturer's instruction. The amount of CAT activity produced by the L gene mutant was then compared to that of wild-type L protein.

9.3. Recovery of Mutant Recombinant RSV

To recover or rescue mutant recombinant RSV, mutations in the L-gene were engineered into plasmids encoding the entire RSV genome in the positive sense (antigenome). The L gene cDNA restriction fragments (BamH I and Not I) containing mutations in the L-gene were removed from pCITE vector and cloned into the full-length RSV cDNA clone. The cDNA clones were sequenced to confirm that each contained the introduced mutations.

Each RSV L gene mutant virus was rescued by co-transfection of the following plasmids into subconfluent Hep-2 cells grown in six-well plates. Prior to transfection, the Hep-2 cells were infected with MVA, a recombinant vaccinia virus which expresses T7 RNA polymerase. One hour later, cells were transfected with the following plasmids:

pCITE-N: encoding wild-type RSV N gene, 0.4 µg
pCITE-P: encoding wild-type RSV P gene, 0.4 µg
pCITE-L mutant: encoding mutant RSV L gene, 0.2 µg
pRSVL mutant: full-length genomic RSV of the positive sense (antigenome) containing the same L-gene mutations as pCITE-L mutant, 0.6 µg DNA was introduced into cells by lipofecTACE (Life Technologies) in OPTI-MEM. After five hours or overnight transfection, the transfection medium was removed and replaced with 2% MEM. Following incubation at 35° C. for three days, the media supernatants from the transfected cells were used to infect Vero cells. The virus was recovered from the infected Vero cells and the introduced mutations in the recovered recombinant viruses confirmed by sequencing of the RT/PCR DNA derived from viral RNA.

Examples of the L gene mutants obtained by charged to alanine scanning mutagenesis are shown in the Table 2. Mutants were assayed by determining the expression of CAT by pRSV/CAT minigenome following co-transfection of plasmids expressing N, P and either wild-type or mutant L. Cells were harvested and lysed 40 hours post-transfection after incubation at 33° C. or 39° C. The CAT activity was monitored by CAT ELISA assay (Boehringer Mannheim). Each sample represents the average of duplicate transfections. The amount of CAT produced for each sample was determined from a linear standard curve.

From the above preliminary studies, different types of mutations have been found.

9.3.1. Detrimental Mutations

Seven L protein mutants displayed a greater than 99% reduction in the amount of CAT produced compared to that of wild-type L protein. These mutations drastically reduced the activity of the RSV polymerase and are not expected to be viable.

TABLE 2

CAT Expression levels of Mutant RSV L-gene

| Mut. | Conc. of CAT (ng/mL) 33° C. | 39° C. | Cluster | Charge Charge to Alanine Change | Rescued Virus |
|---|---|---|---|---|---|
| A33 | 0.246 | Bkg | 5 | 135E, 136K | No |
| A73 | 3.700 | 0.318 | 3 | 146D, 147E, 148D | Yes |
| A171 | 3.020 | Bkg | 3 | 157K, 158D | Yes |
| A81 | 1.000 | 0.280 | 3 | 255H, 256K | Yes |
| A185 | Bkg | Bkg | 3 | 348E, 349E | No |
| A91 | Bkg | Bkg | 3 | 353R, 355R | No |
| A101 | Bkg | Bkg | 3 | 435D, 436E, 437R | No |
| A192 | 1.960 | Bkg | 3 | 510E, 511R | Yes |
| A11 | 0.452 | Bkg | 1 | 520R | Yes |
| A111 | 2.320 | 0.267 | 4 | 568H, 569E | Yes |
| A121 | 0.772 | Bkg | 2 | 587L, 588R | No |
| A133 | Bkg | Bkg | 4 | 620E, 621R | No |
| A141 | 2.800 | Bkg | 3 | 1025K, 1026D | Yes |
| A25 | 0.169 | Bkg | 3 | 1033D, 1034D | Yes |
| A45 | 5.640 | 0.478 | 5 | 1187D, 1188K | Yes |
| A153 | 4.080 | 0.254 | 5 | 1187D, 1188K, 1189R, 1190E | Yes |
| A162 | 10.680 | Bkg | 3 | 1208E, 1209R | No |
| A201 | Bkg | Bkg | 3 | 1269E, 1270K | No |
| A211 | 2.440 | 0.047 | 3 | 1306D, 1307E | Yes |
| A221 | 0.321 | Bkg | 3 | 1378D, 1379E | No |
| A231 | Bkg | Bkg | 3 | 1515E, 1516K | No |
| A241 | 1.800 | 0.308 | 3 | 1662H, 1663K | Yes |
| A57 | 5.660 | 0.706 | 3 | 1725D, 1726K | Yes |
| A65 | 3.560 | 0.168 | 2 | 1957R, 1958K | Yes |
| A251 | 0.030 | Bkg | 3 | 2043D, 2044K | Yes |
| A261 | Bkg | Bkg | 3 | 2102K, 2103H | No |
| AD11 | 2.800 | 0.456 | 5 and 3 | 1187D, 1188K, 1725D, 1726K | No |
| AD21 | 2.640 | 0.226 | 5 and 2 | 1187D, 1188K, 1957R, 1958K | No |
| AD31 | 1.280 | 0.192 | 3 and 2 | 1725D, 1726K, 1957R, 1958K | No |
| F1 | Bkg | Bkg | — | 521 F to L | Yes |
| F13 | 0.13 | Bkg | — | 521 F to L | Yes |
| Lwt | 3.16 | — | — | no amino acid changes | Yes |

9.3.2. Intermediate Mutations

Several L mutants showed an intermediate level of CAT production which ranged from 1% to 50% of that wild-type L protein. A subset of these mutants were introduced into virus and found to be viable. Preliminary data indicated that mutant A2 showed 10–to 20–fold reduction in virus titer when grown at 40° C. compared 33° C. Mutant A25 exhibited a smaller plaque formation phenotype when grown at both 33° C. and 39° C. This mutant also had a 10-fold reduction in virus titer at 40° C. compared to 33° C.

9.3.3. Mutants With L Protein Function Similar or Higher Than Wild Type L Protein Some L gene mutants produced CAT gene expression levels similar to or greater than the wild-type L protein in vitro and the recovered virus mutants have phenotypes indistinguishable from wild-type viruses in tissue culture.

Once mutations in L that confer temperature sensitivity and attenuation have been identified, the mutations will be combined to test for the cumulative effect of multiple temperature-sensitivity markers. The L mutants bearing more than one temperature sensitive marker are expected to have lower permissive temperature and to be genetically more stable than single-marker mutants.

The generated L gene mutants may also be combined with mutations present in other RSV genes and/or with non-essential RSV gene deletion mutants (e.g., SH, NS1 and NS2 deletion). This will enable the selection of safe, stable and effective live attenuated RSV vaccine candidates.

10. Generation of Human Respiratory Syncytial Virus Vaccine (RSV) Candidate by Deleting the Viral SH AND M20RF2 Genes

10.1. M2-2 Deletion Mutant

To delete M2-2 genes, two Hind III restriction enzyme sites were introduced at RSV nucleotides 8196 and 8430, respectively, in a cDNA subclone pET(S/B) which contained an RSV restriction fragment from 4478 to 8505. The RSV restriction fragment had been previously prepared by Quikchange site-directed mutagenesis (Strategene, Lo Jolla, Calif.). Digestion of pET(S/B) with Hind III restriction enzyme removed a 234 nucleotide sequence which contained the majority of the M2-2 open reading frame (SEQ ID NO:49). The nucleotides encoding the first 13 amino acids at the N-terminus of the M2-2 gene product were not removed because this sequence overlaps M2-1. The cDNA fragment which contained M2-2 gene deletion was digested with SacI and BamHI and cloned back into a full-length RSV cDNA clone, designated pRSVAM2-2

Infectious RSV with this M2-2 deletion was generated by transfecting pRSVΔM2-2 plasmid into MVA-infected Hep-2 cells expressing N, P and L genes. Briefly, pRSVAM2-2 was transfected, together with plasmids encoding proteins N, P and L, into Hep-2 cells which had been infected with a recombinant vaccinia virus (MVA) expressing the T7 RNA polymerase. Transfection and recovery of recombinant RSV was performed as follows. Hep-2 cells were split five hours or a day before the transfection in six-well dishes. Monolayers of Hep-2 cells at 70%–80% confluence were infected with MVA at a multiplicity of infection (moi) of 5 and incubated at 35° C. for 60 min. The cells were then washed once with OPTI-MEM (Life Technologies, Gaithersburg, M.D.). Each dish was replaced with 1 ml of OPTI-MEM and 0.2 ml transfection medium was added. The transfection medium was prepared by mixing 0.5–0.6 µg of RSV antigenome, 0.4 µg of N plasmid, 0.4 µg of P plasmid, and 0.2 µg of L plasmid in a final volume of 0.1 ml OPTI-MEM medium. This was combined with 0.1 ml of OPTI-MEM containing 10 µl lipofecTACE (Life Technologies). After a 15 minute incubation at room temperature, the DNA/lipofecTACE mixture was added to the cells. The medium was replaced one day later with MEM containing 2% FBS. Cultures were further incubated at 35° C. for 3 days and the supernatants harvested. Three days post-transfection, 0.3–0.4 ml culture supernatants were passaged onto fresh Hep-2 cells and incubated with MEM containing 2% FBS. After incubation for six days, the supernatant was harvested and the cells were fixed and stained by an indirect horse-radish peroxidase method using goat anti-RSV antibody (Biogenesis) followed by a rabbit anti-goat antibody linked to horseradish peroxidase. The virus infected cells were then detected by addition of substrate chromogen (DAKO) according to the manufacturer's instructions. Recombinant RSV which contained M2-2 gene deletion was recovered from the transfected cells. Identification of rRSVAM2-2 was performed by RT/PCR using primers flanking the deleted region. As shown in FIG. 12A, a cDNA fragment which is 234 nucleotides shorter than the wild-type RSV was detected in rRSVΔM2-2 infected cells. No cDNA was detected in the RT/PCR reaction which did not contain reverse transcriptase in the RT reaction. This indicated that the DNA product was derived from viral RNA and not from contamination. The properties of the M2-2 deletion RSV are currently being evaluated.

10.2. SH Deletion Mutant.

To delete the SH gene from RSV, a Sac I restriction enzyme site was introduced at the gene start signal of SH gene at position of nt 4220. A unique SacI site also exists at the C-terminus of the SH gene. Site-directed mutagenesis was performed in subclone pET(A/S), which contains an AvrII(2129) SacI (4478) restriction fragment. Digestion of pET(A/S) mutant with SacI removed a 258 nucleotide fragment of the SH gene. Digestion of the pET(A/S) subclone containing the SH deletion was digested with Avr II and SacI and the resulting restriction fragment was then cloned into a full-length RSV cDNA clone. The full-length cDNA clone containing the SH deletion was designated pRSVΔSH.

Generation of the pRSVΔSH mutant was performed as described above (see 10.1). SH-minus RSV (rRSVΔSH) was recovered from MVA-infected cells that had been co-transfected with pRSVΔSH together with N, P and L expression plasmids. Identification of the recovered rRSVΔSH was performed by RT/PCR using a pair of primers which flanked the SH gene. As shown in FIG. 12A, a cDNA band which is about 258 nucleotides shorter than the wild-type virus was detected in the rRSVΔSH infected cells. No DNA was detected in the RT/PCR reaction which did not have reverse transcriptase in the RT reaction. This indicated that the PCR DNA was derived from viral RNA and was not artifact, and that the virus obtained was truly SH-minus RSV.

10.3. Generation of Both SH and M2-2 Deletion Mutant.

Both SH and M2-2 genes were deleted from the full-length RSV cDNA construct by cDNA subcloning. A Sac I to Bam HI fragment containing M2-2 deletion removed from cDNA subclone pET(S/B)ΔM2-2RSV was cloned into pRSVΔSH cDNA clone. The double gene deletion plasmid pRSVΔSHΔM2-2 was confirmed by restriction enzyme mapping. As shown in FIG. 12B, the SH/M2-2 double deletion mutant is shorter than the wild-type pRSV cDNA.

Recovery of infectious RSV containing both the SH and M2-2 deletion was performed as described earlier. Infectious virus with both SH and M2-2 deleted was obtained from transfected Hep-2 cells.

11. EXAMPLE

Generation of a Human Respiratory Syncytial Virus Vaccine (RSV) Candidate by Deleting a Viral Accessory Gene(S) Either Singly or in Combination Rationale:

Human respiratory syncytial virus is the major course of pneumonia and bronchiolitis in infants under one year of age. RSV is responsible for more than one in five pediatric hospital admissions due to respiratory tract disease and causes 4,500 deaths yearly in the USA alone. Despite decades of investigation to develop an effective vaccine against RSV, no safe and effective vaccine has been achieved to prevent the severe morbidity and significant mortality associated with RSV infection. Various approaches have been used to develop RSV vaccine candidates: formalin-inactivated virus, recombinant subunit vaccine of expressed RSV glycoproteins, and live attenuated virus. Recently, generation of live attenuated RSV mutants has been the focus for the RSV vaccine development. In the past, generation of live attenuated RSV mutant can only be achieved by in vitro passage and/or chemical mutagenesis. Virus was either underattenuated or overattenuated and was not genetically stable. The present investigation provides an immediate approach to generate genetically stable live attenuated RSV vaccines by deleting an accessory gene(s) individually or in combination. Gene deletions are considered to be a very powerful strategy for attenuating RSV because such deletions will not revert and the recombinant RSV deletion mutants are thus expected to be genetically very stable.

RSV is unique among the paramyxoviruses in its gene organization. In addition to the N, P, L, M, G and F genes which are common to all the paramyxoviruses, RSV contains four additional genes which encode five proteins: NS1, NS2, SH, M2-1 and M2-2. M2-1 and M2-2 are translated from two open reading frames that overlap in the middle of the M2 mRNA. M2-1 enhances mRNA transcriptional processivity and also functions as an antitermination factor by increasing transcriptional readthrough at the intergenic junctions (Collins, P. L. et al. *Proc. Natl. Acad Sci. USA* 93, 81–85 (1996); Hardy, R. W. et al. *J. ViroL* 72, 520–526 (1998)). However, the M2-2 protein was found to inhibit RSV RNA transcription and replication in vitro (Collins, P. L. et al.*Proc. Natl. Acad. Sci. USA* 93, 81–85 (1996)). The accessory protein NS1 was reported to be a potent transcription inhibitor (Atreya, P. L. et al., *J. Virol.* 72, 1452–1461 (1998)). The 9H gene has been shown to be dispensable for RSV growth in tissue culture in a naturally occurring virus and in a recombinant RSV harboring an engineered SH deletion (Bukreyev, A. et al., *J. Virol* 71(12), 8973–82 (1997); Karron, R. A. et al. *J. Infect. Dis.* 176, 1428–1436 (1997)). SH minus RSV replicates as well as the wild type RSV in vitro. Recently, it was reported that the NS2 gene could also be deleted (Teng, M. N., et al *J Virol* 73(1), 466–73 (1999); Buchholz, U. J.et al. *J Virol* 73(1), 251–9 (1999)). Deletion of M2-1, M2-2, and NS1 has not been reported, neither was deletion of more than two nonessential genes reported. Traditionally, live attenuated virus mutants were generated by passaging of RSV at lower temperature for many times and/or mutagenized by chemical reagents. The mutations are introduced randomly and the virus phenotype is difficult to maintain because revertants may develop. The ability to produce virus from an infectious cDNA makes it possible to delete gene or genes that are associated with virus pathogenesis. Gene deletion alone or in combination with mutations in the other viral genes (G, F, M, N, P and L) may yield a stably attenuated RSV vaccine to effectively protect RSV infection.

11.1 Generation of a Human Respiratory Syncytial Virus Vaccine (RSV) Candidate by Deleting the Viral M2-2 Gene This example describes production of a recombinant RSV in which expression of the M2-2 gene has been ablated by removal of a polynucleotide sequence encoding the M2-2 gene and its encoded protein. The RSV M2-2 gene is encoded by M2-2 gene and its open reading frame is partially overlapped with the 5'-proximal M2-1 open reading frame by 12 amino acids (Collins, P. L. et al. *Proc. NatlAcad Sci. USA* 93, 81–85 (1996)). The predicted M2-2 polypeptide contains 90 amino acids, but the M2-2 protein has not yet been identified intracelluarly. The M2-2 protein downregulates RSV RNA transcription and replication in a minigenome model system (Collins, P. L. et al. *Proc. Natl. Acad. Sci. USA* 92, 11563–11567 (1995)). The significance of this negative effect on RSV RNA transcription and replication in the viral replication cycle is not known.

11.1.1 Recovery of Recombinant RSV That Lacks the M2-2 Gene

To produce a recombinant RSV that no longer expresses the M2-2 protein, the M2-2 gene was deleted from a parental RSV cDNA clone (Jin, H. et al. *Virology* 251, 206–214 (1998)). The antigenomic cDNA clone encodes a complete antigenomic RNA of strain A2 of RSV, which was used successfully to recover recombinant RSV. This antigenomic cDNA contains a single nucleotide change in the leader region at position 4 from C to G in its antigenomic sense. The construction of plasmid pA2ΔM2-2 involved a two step cloning procedure. Two Hind III restriction enzyme sites were introduced at RSV sequence of 8196 nt and 8430 nt respectively in a cDNA subclone (pET-SIB) that contained RSV Sac I (4477 nt) to BamH I (8504 nt) cDNA fragment using Quickchange mutagenesis kit (Strategene). Digestion of this cDNA clone with Hind III restriction enzyme removed the 234 nt Hind III cDNA fragment that contained the M2-2 gene. The remaining Sac I to BamH I fragment that did not contain the M2-2 gene was then cloned into a RSV antigenomic cDNA pRSVC4G. The resulting plasmid was designated as pA2ΔM2-2.

To recover recombinant RSV with the M2-2 open reading frame deleted, pA2ΔM2-2 sas transfected, together with plasmids encoding the RSV N, P, and L proteins under the control of 17 promoter, into Hep-2 cells which had been infected with a modified vaccinia virus encoding the T7 RNA polymerase (MVA-T7). After 5 hours incubation of the transfected Hep-2 cells at 35° C., the medium was replaced with MEM containing 2% FBS and the cells were further incubated at 35° C. for 3 days. Culture supernatants from the transfected Hep-2 cells were used to infect the fresh Hep-2 or Vero cells to amplify the rescued virus. Recovery of rA2ΔM2-2 was indicated by syncytial formation and confirmed by positive staining of the infected cells using polyclonal anti-RSV A2 serum. Recovered rA2ΔM2-2 was plaque purified three times and amplified in Vero cells. To confirm that rA2M2-2 contained the M2-2 gene deletion, viral RNA was extracted from virus and subjected to RT/PCR using a pair of primers spanning the M2-2 gene. Viral RNA was extracted from rA2ΔM2-2 and rA2 infected cell culture supernatant by an RNA extraction kit (RNA STAT-50, Tel-Test, Friendswood, Tex.). Viral RNA was reverse transcribed with reverse transcriptase using a primer complementary to viral genome from 7430 nt to 7449 nt. The cDNA fragment spanning the M2-2 gene was amplified by PCR with primer V1948 (7486 nt to 7515 nt at positive-sense) and primer V1581 (8544 nt to 8525 nt at negative sense). The PCR product was analyzed on a 1.2% agarose gel and visualized by EtBr staining. As shown in FIG. 13B, wild type rA2 yielded a PCR DNA product corresponding to the predicted 1029 nt fragment, whereas rA2ΔM2-2 yielded a PCR product of 795 nt, 234 nt shorter. Generation of RT/PCR product was dependent on the RT step, indicating that they were derived from RNA rather than from DNA contamination.

11.1.2 RNA Synthesis of rA2 μM2-2 mRNA expression from cells infected with rA2ΔM2-2 or rA2 was analyzed by Northern blot hybridization analyses. Total cellular RNA was extracted from rA2ΔM2-2 or rA2 infected cells by an RNA extraction kit (RNA STAT-60, Tel-Test, Friendswood, Tex.). RNA was electrophoresed on a 1.2% agarose gel containing formaldehyde and transferred to a nylon membrane (Amersham Pharmacia Biotech, Piscataway, N.J.). The membrane was hybridized with a RSV gene specific riboprobe labeled with digoxigenin (Dig). The hybridized RNA bands were visualized by using Dig-Luminescent Detection Kit for Nucleic Acids (Boehringer Mannheim, Indianapolis, Ind.). Hybridization of the membranes with riboprobes was done at 65° C., membrane washing and signal detection were performed according to the standard procedures. To examine mRNA synthesis from rA2ΔM2-2 and rA2, accumulation of the M2 mRNA and the other viral mRNA products in infected Vero cells was analyzed by Northern blot hybridization. Hybridization of the blot with a probe specific to the M2-2 open reading frame did not detect any signal in rA2ΔM2-2 infected cells. Instead, a shorter M2 mRNA was detected in rA2ΔM2-2 infected cells using a riboprobe specific to the M2-1 gene (FIG. 14A). These observations confirmed that the M2-2 gene was deleted from rA2ΔM2-2. Accumulation of the other nine RSV mRNA transcripts was also examined and the amounts of each mRNA were found to be comparable between rA2ΔM2-2 and rA2 infected cells. Examples of Northern blots probed with N, SH, G and F are also shown in FIG. 14A. Slightly faster migration of F-M2 bicistronic MRNA was also discernible due to the deletion of the M2-2 region.

The M2-2 protein was previously reported to be a potent transcriptional negative regulator in a minigenome replication assay. However, deletion of the M2-2 gene from virus did not appear to affect viral mRNA production in infected cells. To determine if levels of viral antigenome and genome RNA of rA2ΔM2-2 were also similar to rA2, the amount of viral genomic and antigenomic RNA produced in infected Vero and Hep-2 cells was examined by Northern hybridization. Hybridization of the infected total cellular RNA with a $^{32}$P-labeled F gene riboprobe specific to the negative genomic sense RNA indicated that much less genomic RNA was produced in cells infected with rA2ΔM2-2 compared to rA2 (FIG. 14B). A duplicate membrane was hybridized with a $^{32}$P-labeled F gene riboprobe specific to the positive sense RNA. Very little antigenomic RNA was detected in cells infected with rA2ΔM2-2, although the amount of the F mRNA in rA2ΔM2-2 infected cells was comparable to rA2. Therefore, it appears that RSV genome and antigenome synthesis was down-regulated due to deletion of the M2-2 gene. This down-regulation was seen in both Vero and Hep-2 cells and thus was not cell type dependent.

11.1.3 Protein Synthesis of rA2ΔM2-2

Since the putative M2-2 protein has not been identified in RSV infected cells previously, it was thus necessary to demonstrate that the M2-2 protein is indeed encoded by RSV and produced in infected cells. A polygonal antiserum was produced against the M2-2 fusion protein that was expressed in a bacterial expression system. To produce antiserum against the M2-2 protein of RSV, a cDNA fragment encoding the M2-2 open reading frame from 8155 nt to 8430 nt was amplified by PCR and cloned into the PRSETA vector (Invitrogen, Carlsbad, Calif.). pRSETA/M2-2 was transformed into BL21-Gold(DE3)plysS cells (Strategene, La Jolla, Calif.) and expression of His-tagged M2-2 protein was induced by IPTG. The M2-2 fusion protein was purified through HiTrap affinity columns (Amersham Pharmacia Biotech, Piscataway, N.J.) and was used to immunize rabbits. Two weeks after a booster immunization, rabbits were bled and the serum collected.

Viral specific proteins produced from infected cells were analyzed by immunoprecipitation of the infected cell extracts or by Western blotting. For immunoprecipitation analysis, the infected Vero cells were labeled with $^{35}$S-promix (100 μCi/ml $^{35}$S-Cys and $^{35}$S-Met, Amersham, Arlington Heights, Ill.) at 14 hr to 18 hr postinfection. The labeled cell monolayers were lysed by RIPA buffer and the polypeptides immunoprecipitated by polyclonal anti -RSV A2 serum (Biogenesis, Sandown, N.H.) or anti-M2-2 serum. Immunoprecipitation of rA2 infected Vero cell lysates with anti-M2-2 antibody produced a protein band of approximately 10 kDa, which is the predicated size for the M2-2 polypeptide. This polypeptide was not detected in rA2ΔM2-2 infected cells (FIG. 15A), confirming that M2-2 is a protein product produced by RSV and its expression was ablated from rA2ΔM2-2. The overall polypeptide pattern of rA2ΔM2-2 was indistinguishable from that of rA2. However, it was noted that slightly more P and SH proteins were produced in rA2ΔM2-2 infected Vero cells by immunoprecipitation. Nevertheless, by Western blotting analysis, a comparable amount of SH was produced in cells infected with rA2ΔM2-2 or rA2 (FIG. 15B).

Immunoprecipitated polypeptides were electrophoresed on 17.5% polyacrylamide gels containing 0.1% SDS and 4 M urea, and detected by autoradiography. For Western blotting analysis, Hep-2 and Vero cells were infected with rA2ΔM2-2 or rA2. At various times postinfection, virus infected cells were lysed in protein lysis buffer and the cell lysates were electrophoresed on 17.5% polyacrylamide gels containing 0.1% SDS and 4 M urea. The proteins were transferred to a nylon membrane. Immunoblotting was performed as described in Jin et al. (Jin, H. et al. *Embo J* 16(6), 1236–47 (1997)), using polyclonal antiserum against M2-1, NS1, or SH.

Western blotting was used to determine the protein synthesis kinetics of rA2ΔM2-2 in both Vero and Hep-2 cell lines. Hep-2 or Vero cells were infected with rA2ΔM2-2 or rA2 at moi of 0.5 and at various times of postinfection, the infected cells were harvested and the polypeptides separated on a 17.5% polyacrylamide gel containing 4 M urea. The proteins were transferred to a nylon membrane and probed with polyclonal antisera against the three accessory proteins: M2-1, NS1 and SH. Protein expression kinetics for all three viral proteins were very similar for rA2ΔM2-2 and rA2 in both Hep-2 and Vero cells (FIG. 15B). Synthesis of the NS1 protein was detected at 10 hr postinfection, which was slightly earlier than M2-1 and SH because the NS1 protein is the first gene translated and is a very abundant protein product in infected cells. Similar protein synthesis kinetics was also observed when the membrane was probed with a polyclonal antiscrunm against RSV (data not shown). Comparable M2-1 was detected in rA2ΔM2-2 infected cells, indicating that deletion of the M2-2 open reading frame did not affect the level of the M2-1 protein that is translated by the same M2 mRNA.

11.1.4 Growth Analysis of Recombinant RSV in Tissue Culture

To compare plaque morphology of rA2ΔM2-2 with rA2, Hep-2 or Vero cells were infected with each virus and overlayed with semisolid medium composed of 1% methylcellulose and 1×L15 medium with 2% FBS. Five days after infection, infected cells were immunostained with antisera against RSV A2 strain. Plaque size was determined by measuring plaques from photographed microscopic images. Plaque formation of rA2ΔM2-2 in Hep-2 and Vero cells was compared with rA2. As shown in FIG. 16, rA2ΔM2-2 formed pin point sized plaques in Hep-2 cells, with a reduction of about 5-fold in virus plaque size observed for rA2ΔM2-2 compared to rA2. However, only a slight reduction in plaque size (30%) was seen in Vero cells infected with rA2ΔM2-2.

A growth kinetics study of rA2ΔM2-2 in comparison with rA2 was performed in both Hep-2 and Vero cells. Cells grown in 6-cm dishes were infected with rA2 or rA2ΔM2-2 at a moi of 0.5. After 1 hr adsorption at room temperature, infected cells were washed three times with PBS, replaced with 4 ml of OPTI-MEM and incubated at 35° C. incubator containing 5% $CO_2$. At various times post-infection, 20011 culture supernatant was collected, and stored at −70° C. until virus titration. Each aliquot taken was replaced with an equal amount of fresh medium. Virus titer was determined by plaque assay in Vero cells on 12-well plates using an overlay of 1% methylcellulose and 1×L15 medium containing 2% FBS. As seen in FIG. 17, rA2ΔM2-2 showed very slow growth kinetics and the peak titer of rA2ΔM2-2 was about 2.5–3 log lower than that of rA2 in Hep-2 cells. In Vero cells, rA2ΔM2-2 reached a peak titer similar to rA2. To analyze virus replication in different host cells, each cell line grown in 6-well plates was infected with rA2 ΔM2-2 or rA2 at moi of 0.2. Three days postinfection, the culture supernatants were collected and virus was quantitated by plaque assay. rA2ΔM2-2 was examined for its growth properties in various cell lines that derived from different hosts with different tissue origins (Table 3). Significantly reduced replication of rA2ΔM2-2, two orders of magnitude less than rA2, was observed in infected Hep-2, MRC-5, and Hela cells, all of human origin. However, replication of rA2ΔM2-2 was only slightly reduced in MDBK and LLC-MK2 cells that are derived from bovine and rhesus monkey kidney cells, respectively.

TABLE 3

Replication levels of rA2 M2-2 and rA2 in various cell lines

| | | | Virus titer [$\log_{10}$(pfu/ml)] | |
|---|---|---|---|---|
| Cell lines | Host | Tissue origin | rA2 | rA2ΔM2-2 |
| Vero | Monkey | Kidney | 6.1 | 6.1 |
| Hep-2 | Human | Larynx | 6.2 | 4.3 |
| MDBK | Bovine | Kidney | 6.1 | 5.5 |
| MRC-5 | Human | Lung | 5.5 | 3.0 |
| Hela | Human | Cervix | 6.6 | 4.5 |
| LLC-MK2 | Monkey | Kidney | 6.7 | 6.1 |

11.15 Replication of rA2ΔM2-2 in Mice and Cotton Rats

Virus replication in vivo was determined in respiratory pathogen-free 12-week-old Balb/c mice (Simonsen Lab., Gilroy, Calif.) and S. Hispidus cotton rats (Virion Systems, Rockville, Md.). Mice or cotton rats in groups of 6 were inoculated intranasally under light methoxyflurane anesthesia with $10^6$ pfu per animal in a 0.1-ml inoculum of rA2 or rA2ΔM2-2. On day 4 postinoculation, animals were sacrificed by $CO_2$ asphyxiation and their nasal turbinates and lungs were obtained separately. Tissues were homogenized and virus titers were determined by plaque assay in Vero cells. To evaluate immunogenicity and protective efficacy, three groups of mice were inoculated intranasally with rA2ΔrA2ΔM2-2 or medium only at day 0. Three weeks later, mice were anesthetized, serum samples were collected, and a challenge inoculation of $10^6$ pfu of biologically derived wild type RSV strain A2 was administered intranasally. Four days post-challenge, the animals were sacrificed and both nasal turbinates and lungs were harvested and virus titer determined by plaque assay. Serum antibodies against RSV A2 strain were determined by 60% plaque reduction assay (Coates, H.V. et al., AM *J. Epid.* 83:299–313 (1965)) and by immunostaining of RSV infected cells.

TABLE 4

Replication of rA2ΔM2-2 and rA2 in cotton rats

| | Virus titer (mean $\log_{10}$ pfu/g tissue ± SE)[a] | |
|---|---|---|
| Virus | Nasal turbinates | Lung |
| rA2 | 4.0 ± 0.33 | 5.5 ± 0.12 |
| rA2ΔM2-2 | <1.4 | <1.4 |

[a]Groups of six cotton rats were immunized intranasally with $10^6$ pfu of the indicated virus on day 0. The level of infected virus replication at day 4 was determined by plaque assay on indicated specimens, and the mean $\log_{10}$ titer ± standard error (SE) per gram tissue were determined.

To evaluate levels of attenuation and immunogenicity of rA2ΔM2-2, replication of rA2ΔM2-2 in the upper and lower respiratory tract of mice and cotton rats was examined. Cotton rats in groups of 6 were inoculated with $10^6$pfu of rA2ΔM2-2 or rA2 intranasally. Animals were sacrificed at 4 days postinoculation, their nasal turbinates and lung tissues were harvested, homogenized, and levels of virus replication in these tissues were determined by plaque assay. rA2ΔM2-2 exhibited at least 2 log reduction of replication in both nasal turbinates and lungs of the infected cotton rats (Table 4). No virus replication was detected in cotton rats infected with rA2ΔM2-2, whereas a high level of wild type rA2 virus replication was detected in both the upper and lower respiratory tract of cotton rats. Attenuation of rA2ΔM2-2 was also observed in mice. Geometric mean titer of virus replication and standard error obtained from two experiments are shown in Table 5. rA2ΔM2-2 replication was only detected in one or two of 12 infected mice. The replication was limited, only a few plaques were observed at $10^{-1}$ dilution of the tissue homogenates. Despite its restricted replication in mice, rA2ΔM2-2 induced significant resistance to challenge with wild type A2 RSV (Table 5). When mice previously inoculated with rA2 ΔM2-2 or rA2 were inoculated intranasally with $10^6$ pfu dose of wild type A2 strain, no wild type A2 virus replication was detected in the upper and lower respiratory tract of mice. Therefore, rA2ΔM2-2 was fully protective against wild type A2 virus challenge.

The immunogenicity of rA2ΔM2-2 was also examined. Two groups of mice were infected with rA2ΔM2-2 or rA2, and three weeks later, serum samples were collected. The serum neutralization titer was determined by 50% plaque reduction titer. The neutralization titer from rA2ΔM2-2 infected mice was comparable to that of rA2, both had 60% plaque reduction titer at 1:16 dilution. The serum obtained from rA2ΔM2-2 infected mice was also able to immunostain RSV plaques, confirming that RSV-specific antibodies were produced in rA2ΔM2-2 infected mice.

TABLE 5

Replication of rA2ΔM2-2 and rA2 in mice, and protection against wild type A2 RSV challenge

| Immunizing Virus | Virus replication[a] (Mean log$_{10}$ pfu/g tissue ± SE) | | RSV A2 replication after challenge[b] (Mean log$_{10}$ pfu/g tissue ± SE) | |
|---|---|---|---|---|
| | Nasal turbinates | Lung | Nasal turbinates | Lung |
| rA2 | 3.72 ± 0.33 | 4.0 ± 0.13 | <1.4 | <1.4 |
| rA2ΔM2-2 | <1.4 | <1.4 | <1.4 | <1.4 |
| Control | <1.4 | <1.4 | 3.53 ± 0.17 | 4.10 ± 0.13 |

[a]Groups of 12 Balb/c mice were immunized intranasally with 10$^6$ pfu of the indicated virus on day 0. The level of infected virus in indicated tissues was determined by plaque assay at day 4, and the mean log$_{10}$ titer ± standard error (SE) per gram tissue were determined.
[b]Groups of 6 Balb/c Mice were intranasally administered with 10$^6$ pfu of RSV A2 on day 21 and sacrificed 4 days later. Replication of wild type RSV A2 in tissues as indicated was determined by plaques assay, and the mean log$_{10}$ titer ± standard error (SE) per gram tissue were determined.

The two RSV antigenic subgroups, A and B, exhibit a relatively high degree of conservation in M2-2 proteins, suggesting functional importance for the M2-2 protein. Transcriptional analysis for rA2 and rA2ΔM2-2 yielded important findings within the present example. Although overall mRNA transcriptional levels were substantially the same for both viruses, Northern blot analysis revealed dramatic reduction of virus genome and antigenome RNA for rA2ΔM2-2 compared to wild type rA2. This finding is contradictory with what has been reported for the negative transcriptional regulation of the M2-2 protein in a minigenome system. It thus appears that the functional role of M2-2 in the virus life cycle is more complicated than previously thought. Nevertheless, the reduction in the level of genome and antigenome of rA2ΔM2-2 did not appear to affect virus yields in infected Vero cells.

The finding that rA2ΔM2-2 exhibited host range restricted replication in different cell lines provided a good indication that deletion of a nonessential gene is a good means to create a host range mutant, which can be a very important feature for vaccine strains. rA2ΔM2-2 did not replicate well in several cell lines that are derived from human origin, lower virus yield was produced from these cell lines. However, the levels of protein synthesis in Hep-2 cells were similar to Vero cells that produced high levels of rA2ΔM2-2. This indicated that the defect in virus release was probably due to a defect in a later stage, probably during the virus assembly process.

The finding that the M2-2 minus virus grows well in Vero cells and exhibits attenuation in the upper and lower respiratory tracts of mice and cotton rats presents novel advantages for vaccine development. The reduced replication in respiratory tracts of rodents did not affect immunogenicity and protection against challenging wild type virus replication, indicating that this M2-2 minus virus may serve as a good vaccine for human use. The nature of the M2-2 deletion mutation, involving a 234 nt deletion, represents a type of mutation that will be highly refractory to reversion.

11.2 Generation of a Human Respiratory Syncytial Virus Vaccine (RSV) Candidate by Deleting the Viral SH Gene This example describes production of a recombinant RSV in which expression of the SH gene has been ablated by removal of a polynucleotide sequence encoding the SH gene and its encoded protein. The RSV SH protein is encoded by the SH mRNA which is the 5$^{th}$ gene translated by RSV. The SH protein contains 64 amino acids in the strain A2 and contains a putative transmembrane domain at amino acid positions 14–41. The SH protein only has counterparts in simian virus 5 (Hiebert, S. W. et al. 5. *J Virol* 55(3), 744–51 (1985)) and mumps virus (Elango, N. et al. *J Virol* 63(3), 1413–5 (1989)). The function of the SH protein has not been defined. This example demonstrated that the entire SH gene can be removed from RSV. Thus, SH gene deletion may provide an additional method for attenuating RSV by itself or in combination with other gene deletions or mutations.

To produce a recombinant RSV having deletion in the RSV, the entire SH open reading frame was deleted from an infectious cDNA clone that derived from the RSV A2 strain. A two step cloning procedure was performed to delete the SH gene (from 4220 nt to 4477 nt) from a cDNA subclone. A Sac I restriction enzyme site was introduced at the gene start signal of the SH gene at position of 4220 nt. A unique Sac I site also exists at the C-terminal of the SH gene at position of 4477 nt. Site-directed mutagenesis to introduce a Sac I site at the 5' of the SH gene was performed in pET(A/S) subclone, which contained Avr II (2129 nt) to Sac I (4477 nt) restriction fragment of RSV sequence. Digestion of pET(A/S) plasmid that contained the introduced Sac I site with Sac I restriction enzyme removed 258 nt fragment of the SH gene. pET(A/S) which had the SH gene deletion was digested with Avr II and Sac I and the released RSV restriction fragment was then cloned into a full length RSV cDNA clone. The full-length cDNA clone containing the SH gene deletion was designated pA2ΔSH.

Generation of pA2ΔSH mutant was performed as described above (see Section 7). SH-minus RSV (rA2ΔSH) was recovered from MVA-infected cells that had been co-transfected with pA2 ΔSH together with three plasmids that expressed the N, P and L proteins, respectively. Identification of the recovered rA2ΔSH was performed by RT/PCR using a pair of primers which flanked the SH gene. A cDNA band that is about 258 nucleotide shorter than the wild-type RSV (rA2) was detected in the rA2ΔSH infected cells. No PCR product was seen in the RT/PCR reaction that did not have reverse transcriptase in the RT reaction. This indicated that the PCR DNA was derived from viral RNA and is not artifact, and the virus obtained is truly SH-minus RSV.

To compare plaque morphology of rA2ΔSH with rA2, Hep-2 or Vero cells were infected with each virus and overlayed with semisolid medium composed of 1% methylcellulose and 1×L15 medium with 2% FBS. Five days after infection, infected cells were immunostained with antisera against RSV A2 strain. The plaque size of rA2ΔSH is similar to that of rA2 in both Hep-2 and Vero cells.

To analyze virus replication in different cell lines that were derived from various hosts with different tissue origin, each cell line grown in 6-well plates was infected with rA2ΔSH or rA2 at moi of 0.2. Three days postinfection, the culture supernatants were collected and virus was quantitated by plaque assay. As shown in Table 6, replication of rA2ΔSH was very similar to rA2 in all the cell lines examined, indicating that the growth of SH-minus RSV was not substantially affected by host range effects.

TABLE 6

Growth comparison of rA2ΔSH and rA2 in different cell lines

| | | | Virus titer [log$_{10}$(pfu/ml)] | |
|---|---|---|---|---|
| Cell lines | Host | Tissue origin | rA2 | rA2ΔSH |
| Vero | Monkey | Kidney | 5.8 | 5.7 |
| Hep-2 | Human | Larynx | 6.5 | 6.1 |
| MDBK | Bovine | Kidney | 6.3 | 6.6 |
| MRC-5 | Human | Lung | 5.5 | 5.3 |
| Hela | Human | Cervix | 6.5 | 6.0 |

Virus replication in vivo was determined in respiratory pathogen-free 12-week-old Balb/c mice (Simonsen Lab., Gilroy, Calif.). Mice in groups of 6 were inoculated intranasally under light methoxyflurane anesthesia with $10^6$ pfu per animal in a 0.1-ml inoculum of rA2 or rA2ΔSH. On day 4 postinoculation, animals were sacrificed by $CO_2$ asphyxiation and their nasal trubinates and lungs were obtained separately. Tissues were homogenized and virus titers were determined by plaque assay in Vero cells. As shown in Table 7, level of rA2ΔSH replication in lower respiratory tract was only slightly lower than rA2, indicating that SH deletion alone may not be sufficient to attenuate RSV.

TABLE 7

Replication of rA2ΔSH and rA2 in mice

| Virus | Virus titer in lung (mean $log_{10}$ pfu/g tissue ± SE)[a] |
|---|---|
| rA2 | 3.75 ± 0.07 |
| rA2ΔSH | 3.21 ± 0.25 |

[a]Groups of mice were immunized intranasally with $10^6$ pfu of the indicated virus on day 0. The level of infected virus replication at day 4 was determined by plaque assay on indicated specimens, and the mean $log_{10}$ titer ± standard error (SE) per gram tissue were determined.

11.3 Generation of a Human Respiratory Syncytial Virus Vaccine (RSV) Candidate by Deleting the Viral NS1 Gene This example describes production of a recombinant RSV in which expression of the NS1 gene has been ablated by removal of a polynucleotide sequence encoding the NS1 gene and its encoded protein. The RSV NS1 is encoded by the 3' proximal NS1 gene in the 3' to 5' direction of the RSV gene map. The NS1 protein is a small 139-amino acid polypeptide and its mRNA is most abundant of the RSV mRNA. The function of the NS1 protein has not yet been clearly identified. In the reconstituted RSV minigenome system, the NS1 protein appeared to be a negative regulatory protein for both transcription and RNA replication of a RSV minigenome (Grosfeld, H. et al. *J. Virol* 69, 5677–5686 (1995)). The NS1 protein does not have a known counterpart in other paramyxoviruses and its function in virus replication is not known. This example demonstrated that the entire NS1 gene can be removed from RSV and NS1 deletion may provide an additional method for attenuating RSV or in combination with other RSV gene deletions or mutations.

To delete the NS1 gene from RSV, two restriction enzyme sites were inserted at positions of the NS1 gene start signal and downstream of the NS1 gene end signal. A two step cloning procedure was performed to delete the entire NS1 gene from RSV. A Pst I restriction enzyme site was introduced at position of 45 nt and at position of 577 nt of RSV sequence by site-directed mutagenesis. Mutagenesis was performed in pET(X/A) cDNA subclone, which contained the first 2128 nucleotides of RSV sequences that encode the NS1, NS2 and part of the N gene of RSV. The 2128 nucleotide RSV sequence was cloned into the pET vector through the Xma I and Avr II restriction enzyme sites. Digestion of pET(X/A) plasmid that contained the introduced two Pst I restriction enzyme sites removed the 532 nucleotide fragment that contained the NS1 gene. The deletion included the NS1 gene start signal, the NS1 coding region, and the NS1 gene end signal. pET(X/A) which contained the NS1 deletion was digested with Avr II and Sac I and the released restriction fragment was then cloned into a full length RSV cDNA clone. The full-length RSV antigenomic cDNA clone containing the NS1 gene deletion was designated pA2ΔNS 1.

Generation of pA2ΔNS1 mutant was performed as described above (see Section 7). NS1-minus RSV (rA2ΔNS1) was recovered from MVA-infected cells that had been co-transfected with pA2ΔNS1 together with three plasmids that expressed the N, P and L proteins, respectively. Recovery of infectious RSV was indicated by syncytial formation and confirmed by immunostaining with an antibody against RSV. Identification of the recovered rA2ΔNS1 was performed by RTIPCR using a pair of primers flanking the NS1 gene. A cDNA band that is about 532 nt shorter than the wild-type RSV (rA2) was detected in the rA2ΔNS1 infected cells. No PCR product was seen in the RT/PCR reaction that did not have reverse transcriptase in the RT reaction. This indicated that the PCR DNA was derived from viral RNA and is not artifact, and the virus obtained is truly NS1-minus RSV.

mRNA expression from cells infected with rA2ΔNS1 or rA2 was analyzed by Northern blot hybridization analyses. Total cellular RNA was extracted from rA2ΔNS1 or rA2 infected cells by an RNA extraction kit (RNA STAT-60, Tel-Test, Friendswood, Tex.). RNA was electrophoresed on a 1.2% agarose gel containing formaldehyde and transferred to a nylon membrane (Amersham Pharmacia Biotech, Piscataway, N.J.). The membrane was hybridized with a riboprobe specific to the NS 1, NS2 or M2-2 gene. As shown in FIG. 18, no NS1 mRNA was detected in cells infected with rA2ΔNS1 using a probe that was specific to the NS1 gene. The fact that the NS1 gene can be deleted from RSV identifies that the NS1 protein is an accessory protein product that is not essential for RSV replication. rA2ΔNS1 formed very small plaques in infected Hep-2 cells, but only slight plaque size reduction was seen in Vero cells (FIG. 19). The small plaque phenotype is commonly associated with attenuating mutations.

A growth kinetics study of rA2ΔNS1 in comparison with rA2 was performed in Vero cells. Cells grown in 6-cm dishes were infected with rA2 or rA2ΔNS1 at a moi of 0.2. As seen in FIG. 20, rA2ΔNS1 showed very slow growth kinetics and its peak titer was about 1.5 log lower than that of rA2. To analyze virus replication in different host cells, each cell line grown in 6-well plates was infected with rA2ΔNS1 or rA2 at moi of 0.2. Three days postinfection, the culture supernatants were collected and virus was quantitated by plaque assay. rA2ΔNS1 had about 1-1.5 log reduction in virus titer compared to rA2 in Vero, Hep-2 and MDBK cells. About 2 log reduction in virus titer was observed in Hela and MRC5 cells (Table 8). Replication of rA2ΔNS1 in a small animal model is currently being investigated. Preliminary data indicated that rA2ΔNS 1 is attenuated in cotton rats. The NS1 deletion mutant therefore provides an additional method for attenuating RSV.

TABLE 8

Growth comparison of rA2ΔNS1 and rA2 in different cell lines

| | Virus titer [$log_{10}$(pfu/ml)] | |
|---|---|---|
| Cell lines | rA2 | rA2ΔNS1 |
| Vero | 6.4 | 5.5 |
| Hep-2 | 6.7 | 5.1 |
| MDBK | 6.7 | 5.2 |
| MRC-5 | 5.9 | 3.6 |
| Hela | 6.5 | 4.5 |

11.4 Generation of a Human Respiratory Syncytial Virus Vaccine (RSV) Candidate by Deleting the Viral NS2 Gene This example describes production of a recombinant RSV in which expression of the NS2 gene has been ablated by removal of a polynucleotide sequence encoding the NS2 gene and its encoded protein. The NS2 is a small protein that is encoded by the second 3' proximal NS2 gene in the 3' to 5' order of RSV genome. The NS2 protein might be the second most abundant RSV protein of RSV, but its function remains to be identified.

To delete the NS2 gene from RSV, two restriction enzyme sites were inserted at positions of upstream of the NS2 gene start signal and downstream of the NS2 gene end signal. A two step cloning procedure was performed to delete the entire NS1 gene from RSV. A Pst I restriction enzyme site was introduced at position of 577 nt and at position of 110 nt of RSV sequence by site-directed mutagenesis. Mutagenesis was performed in pET(X/A) cDNA subclone, which contained the first 2128 nt of RSV sequences at antigenomic sense that encode the NS1, NS2 and part of the N gene of RSV. The 2128 nt RSV sequences were cloned into the pET vector through the Xma I and Avr II restriction enzyme sites. Digestion of pET(X/A) plasmid that contained the introduced two Pst I restriction enzyme sites removed 533 nucleotide fragment of the NS2 gene. The 533 nt fragment contained the gene start signal of NS2, NS2 coding region and the gene end signal of NS2. pET(X/S) plasmid that contained the NS2 gene deletion was digested with Avr II and Sac I restriction enzymes and the released RSV restriction fragment was then cloned into a full length RSV cDNA clone. The full-length cDNA clone containing the NS2 gene deletion was designated pA2ΔNS2.

Generation of rA2ΔNS2 mutant was performed as described above (see Section 7). NS2-minus RSV (rA2ΔNS2) was recovered from MVA-infected cells that had been co-transfected with pA2ΔNS2 together with three plasmids that expressed the N, P and L proteins, respectively. Recovery of infectious RSV was indicated by syncytial formation and confirmed by immunostaining with an antibody against RSV. Identification of the recovered rRSVΔNS2 was performed by RT/PCR using a pair of primers that flanked the NS2 gene. A cDNA band that is about 533 nucleotide shorter than the wild-type RSV (rA2) was detected in the rA2ΔNS2 infected cells. No PCR product was seen in the RT/PCR reaction that did not have reverse transcriptase in the RT reaction. This indicated that the PCR DNA was derived from viral RNA and is not artifact, and the virus obtained is truly NS2-minus RSV. mRNA expression from cells infected with rA2ΔNS2 or rA2 was analyzed by Northern blot hybridization analyses as described earlier. The blot was hybridized with a riboprobe specific to the NS 1, NS2 or M2-2 gene. As shown in FIG. 18, no NS2 mRNA was detected in cells infected with rA2ΔNS2 using a probe that was specific to the NS2 gene. Comparable level of NS1 and M2 mRNA was detected in rA2ΔNS2-infected cells. The fact that the NS2 gene can be deleted from RSV indicates that the NS2 protein is an accessory protein product that is not essential for RSV replication. rA2ΔNS2 formed very small plaques in infected Hep-2 cells, but plaque size similar to rA2 was seen in rA2ΔNS2 infected Vero cells (FIG. 19). The small plaque phenotype is commonly associated with attenuating mutations.

A growth kinetics study of rA2ΔNS2 in comparison with rA2 was performed in Vero cells. Cells grown in 6-cm dishes were infected with rA2 or rA2ΔNS2 at a moi of 0.2. As seen in FIG. 21, rA2ΔNS2 showed slower growth kinetics and its peak titer was about 5-fold lower than that of rA2. To analyze virus replication in different host cells, each cell line grown in 6-well plates was infected with rA2ΔNS2 or rA2 at moi of 0.2. Three days postinfection, the culture supernatants were collected and virus was quantitated by plaque assay. rA2ΔNS2 had only slight reduction in virus titer compared to rA2 in Vero cells. About a 1 log reduction in virus titer was observed in Hep-2, MDBK, Hela and MRC5 cells (Table 9). Replication of rA2ΔNS2 in a small animal model is currently being investigated. rA2ΔNS2 exhibited about 10-fold reduction of replication in the lower respiratory tract of cotton rats (Table 10). The NS2 deletion mutant therefore provides a method to obtain attenuated RSV.

TABLE 9

Growth comparison of rA2ΔNS2 and rA2 in different cell lines

| Cell lines | Virus titer [$\log_{10}$(pfu/ml)] | |
|---|---|---|
| | rA2 | rA2 NS2 |
| Vero | 6.4 | 6.2 |
| Hep-2 | 6.7 | 5.9 |
| MDBK | 6.7 | 5.2 |
| MRC-5 | 5.9 | 4.7 |
| Hela | 6.5 | 5.5 |

TABLE 10

Replication of rA2ΔNS2 and rA2 in cotton rats

| Virus | Virus titer in lung (mean $\log_{10}$ pfu/g tissue ± SE)[a] |
|---|---|
| rA2 | 3.93 ± 0.13 |
| RA2ΔNS2 | 2.79 ± 0.47 |

[a]Groups of five cotton rats were immunized intranasally with $10^5$ pfu of the indicated virus on day 0. The level of infected virus replication at day 4 was determined by plaque assay on the indicated specimens, and the mean $\log_{10}$ titer ± standard error (SE) per gram tissue was determined.

11.5 Generation of a Human Respiratory Syncytial Virus Vaccine (RSV) Candidate by Deleting the Viral M2-2 and SH Genes This example describes production of a recombinant RSV in which expression of two RSV genes, M2-2 and SH, has been ablated by removal of polynucleotide sequences encoding the M2-2 and SH genes and their encoded proteins. As described earlier, the M2-2 or SH gene is dispensable for RSV replication in vitro. It is possible that deletion of two accessory genes will produce a recombinant RSV with a different attenuation phenotype. The degree of attenuation from deletion of two genes can be increased or decreased.

SH and M2-2 genes were deleted from the full-length RSV cDNA construct through cDNA cloning. A Sac I to BamH I fragment that contained M2-2 deletion in the pET(S/B) subclone as described earlier was removed by digestion with Sac I and BamH I restriction enzymes and was cloned into the full-length RSV antigenomic cDNA clone that contained the SH gene deletion (pA2ΔSH). The resulting plasmid that contained deletion of SH and M2-2 was designated pA2ΔSHΔM2-2. Deletion of SH and M2-2 in pA2ΔSHΔM2-2 plasmid was confirmed by restriction enzyme mapping.

Generation of rA2ΔSHΔM2-2 mutant was performed as described above (see Section 7). Recombinant RSV that contained a deletion of the SH and M2-2 genes (rA2ΔSHΔM2-2) was recovered from MVA-infected cells that had been co-transfected with pA2ΔSHΔM2-2 together with three plasmids that expressed the N, P and L proteins, respectively. Recovery of infectious RSV deletion mutant was indicated by syncytial formation and confirmed by immunostaining with an antibody against RSV.

Deletion of the SH and M2-2 genes in rA2ΔSHΔM2-2 was confirmed by RT/PCR using two sets of primers that flanked the SH gene and the M2-2 gene, respectively.

MRNA expression from cells infected with rA2ΔSHΔM2-2 or rA2 was analyzed by Northern blot hybridization analyses as described earlier. Both SH and M2-2 mRNAs were not detected in cells infected with rA2ΔSHΔM2-2 using a probe that was specific to the SH gene or M2-2 gene. The fact that two RSV genes (SH and M2-2) can be deleted from RSV indicates that the SH and M2-2 proteins are dispensable for RSV replication. In contrast to rA2ΔM2-2 that formed very small plaques in Hep-2 cells, rA2ΔSHΔM2-2 had a plaque size larger than rA2ΔM2-2 (FIG. 19).

A growth kinetics study of rA2ΔSHΔM2-2 in comparison with rA2 was performed in Vero cells. Cells grown in 6-cm dishes were infected with rA2 or rA2ΔSHΔM2-2 at a moi of 0.2. As seen in FIG. 22, rA2ΔSHΔM2-2 showed slower growth kinetics and its peak titer was about 1.5 log lower than that of rA2. This indicated that rA2ΔSHΔM2-2 is attenuated in tissue culture.

To evaluate the level of attenuation of rA2ΔSHΔM2-2, replication of rA2ΔSHΔM2-2 in the lower respiratory tracts of mice was examined. Mice in groups of 6 were inoculated with $10^6$ pfu of rA2ΔSHΔM2-2 or rA2 intranasally. Animals were sacrificed at 4 days postinoculation, their nasal turbinates and lung tissues were harvested, homogenized, and levels of virus replication in these tissues were determined by plaque assay. rA2ΔSHΔM2-2 exhibited about a 2 log reduction of replication in lungs of the infected mice (Table 11). This data indicated that rA2ΔSHΔM2-2 is attenuated in mice, although the degree of attenuation is not as significant as rA2ΔM2-2.

TABLE 11

Replication of rA2ΔSHΔM2-2 and rA2 in mice

| Virus | Virus titer in lung (mean $\log_{10}$ pfu/g tissue ± SE)[a] |
|---|---|
| rA2 | 4.2 ± 0.08 |
| rA2ΔSHΔM2-2 | 2.4 ± 1.2 |

[a]Groups of six mice were immunized intranasally with $10^6$ pfu of the indicated virus on day 0. The level of infected virus replication at day 4 was determined by plaque assay on indicated specimens, and the mean $\log_{10}$ titer ± standard error (SE) per gram tissue were determined.

11.6 Generation of a Human Respiratory Syncytial Virus Vaccine (RSV) Candidate by Deleting the Viral M2-2 and NS1 Genes This example describes production of a recombinant RSV in which expression of two different RSV genes, NS1 and M2-2, has been ablated by removal of polynucleotide sequences encoding the NS1 and M2-2 genes and their encoded proteins. As described earlier, NS1 and M2-2 gene alone is dispensable for RSV replication in vitro. This example provided a different attenuating method by deletion of two accessory genes from RSV.

NS1 and M2-2 genes were deleted from the full-length RSV cDNA construct through cDNA cloning. A Xma I to Avr II fragment that contained NS1 deletion in pET(X/A) subclone was removed by digestion with Xma I and Avr II restriction enzymes and was cloned into the full-length RSV antigenomic cDNA clone that contained the M2-2 gene deletion (pA2ΔM2-2). The resulting plasmid that contained deletion of both NS1 and M2-2 was designated pA2ΔNS1 ΔM2-2. Deletion of NS1 and M2-2 in pA2ΔNS1ΔM2-2 plasmid was confirmed by restriction enzyme mapping.

Generation rA2ΔNS1ΔM2-2 mutant was performed as described above (see section 11.2). Recombinant RSV that contained deletion of NS1 and M2-2 genes was recovered from MVA-infected cells that had been co-transfected with pA2ΔNS1 ΔM2-2 together with three plasmids that expressed the N, P and L proteins, respectively. Recovery of infectious RSV was indicated by syncytial formation and confirmed by immunostaining with an antibody against RSV. Identification of the recovered rA2ΔNS1ΔM2-2 was confirmed by RT/PCR using a pair of primers flanking the NS1 gene and the M2-2 gene.

Replication of rA2ΔNS1 ΔM2-2 in tissue culture cell lines and in small animal models is being studied. Preliminary in vitro data indicated that rA2ΔNS1ΔM2-2 is very attenuated in tissue culture cells and recombinant RSV containing deletion of NS1 and M2-2 genes is more attenuated than rA2ΔSHΔM2-2.

11.7 Generation of a Human Respiratory Syncytial Virus Vaccine (RSV) Candidate by Deleting the Viral NS2 and M2-2 Genes This example describes production of a recombinant RSV in which expression of two different RSV genes, NS2 and M2-2, has been ablated by removal of polynucleotide sequences encoding the NS2 and M2-2 genes and their encoded proteins. As described earlier, NS2 or M2-2 gene is dispensable for RSV replication in vitro. It is possible that deletion of two accessory genes from RSV will produce a recombinant RSV with a different attenuation phenotype.

NS2 and M2-2 genes were deleted from the full-length RSV cDNA construct through cDNA cloning. A Xma I to Avr II fragment that contained NS2 deletion in pET(X/A) subclone was removed by digestion with Xma I and Avr II restriction enzymes and was cloned into the full-length RSV antigenomic cDNA clone that contained the M2-2 gene deletion (pA2ΔM2-2). The resulting plasmid that contained deletion of both NS2 and M2-2 was designated pA2ΔNS2 ΔM2-2. Deletion of NS2 and M2-2 in pA2ΔNS2ΔM2-2 plasmid was confirmed by restriction enzyme mapping.

Generation of rA2ΔNS2ΔM2-2 mutant was performed as described above (see Section 7). Recombinant RSV that contained deletion in the NS2 and M2-2 genes (rA2ΔNS2ΔM2-2) was recovered from MVA-infected cells that had been co-transfected with pA2ΔNS2ΔM2-2 together with three plasmids that expressed the N, P and L proteins, respectively. Recovery of infectious RSV was indicated by syncytial formation and confirmed by immunostaining with an antibody against RSV. Identification of the recovered rA2ΔNS2ΔM2-2 was confirmed by RT/PCR using two pairs of primers flanking the NS2 or M2-2 gene, respectively.

mRNA expression from cells infected with rA2ΔNS2ΔM2-2 or rA2 was analyzed by Northern blot hybridization analyses. As shown in FIG. 23, neither NS2 nor M2-2 mRNA was detected in cells infected with rA2ΔNS2ΔM2-2 using a probe that was specific to the NS2 gene or to the M2-2 gene. Comparable levels of NS1 and SH MRNA expression was observed in cells infected with rA2ΔNS2ΔM2-2 Northern blot data confirmed that expression of both NS2 and M2-2 was ablated in rA2ΔNS2ΔM2-2.

A growth kinetics study of rA2ΔNS2ΔM2-2 in comparison with rA2 was performed in Vero cells. Cells grown in 6-cm dishes were infected with rA2 or rA2ΔNS2ΔM2-2 at a moi of 0.2. As seen in FIG. 24, rA2ΔNS2ΔM2-2 showed very slow growth kinetics and its peak titer was about 10-fold lower than that of rA2. To analyze virus replication in different host cells, each cell line grown in 6-well plates was infected with rA2ΔNS2ΔM2-2 or rA2 at moi of 0.2. Three days postinfection, the culture supernatants were collected and virus was quantitated by plaque assay. rA2ΔNS2ΔM2-2 had about a few fold reduction in virus titer compared to rA2 in Vero cells. However, a 2-3 log reduction in virus titer was observed in Hep-2, MDBK, Hela, MRC5 and LLC-MK2 cells (12). Therefore, replication of rA2ΔNS2ΔM2-2 exhibits a substantial host range effect, which is an indication of attenuation.

TABLE 12

Growth comparison of rA2ΔNS2/M2-2 and rA2 in different cell lines

| Cell lines | Virus titer [log$_{10}$ (pfu/ml)] | |
|---|---|---|
| | rA2 | rA2ΔNS2/M2-2 |
| Vero | 6.4 | 5.7 |
| Hep-2 | 6.7 | 3.5 |
| MDBK | 6.7 | 3.7 |
| MRC-5 | 5.9 | 2.0 |
| Hela | 6.5 | 2.9 |
| LLC-MK2 | 6.7 | 4.8 |

Replication of rA2ΔNS2/M2-2 in vivo was determined in respiratory pathogen-free 4-week old cotton rats. Cotton rats in groups of 5 were inoculated intranasally under light methoxyflurane anesthesia with $10^5$ pfu per animal in a 0.1-ml inoculum of rA2 or rA2ΔNS2ΔM2-2. On day 4 postinoculation, animals were sacrificed by $CO_2$ asphyxiation and their nasal turbinates and lungs were obtained separately. Tissues were homogenized and virus titers were determined by plaque assay in Vero cells. As shown in Table 13, no virus replication was detected in the upper and lower respiratory tracts of cotton rats that were infected with rA2 ΔNS2ΔM2-2. This indicated that deletion of the NS2 and M2-2 genes severely attenuated RSV. Thus, this recombinant RSV with an NS2 and M2-2 deletion might serve as a good vaccine candidate for human use.

TABLE 13

Replication of rA2ΔNS2/M2-2 and rA2 in cotton rats

| Virus | Virus titer (mean log$_{10}$ pfu/g tissue ± SE) | |
|---|---|---|
| | Nasal turbinates | Lung |
| rA2 | 2.30 ± 0.26 | 4.23 ± 0.10 |
| rA2ΔNS2/M2-2 | <1.4 | <1.4 |

[a]Groups of five cotton rats were immunized intranasally with $10^5$ pfu of the indicated virus on day 0. The level of infected virus replication at day 4 was determined by plaque assay on indicated specimens, and the mean log$_{10}$ titer ± standard error (SE) per gram tissue were determined.

11.8 Generation of a Human Respiratory Syncytial Virus Vaccine (RSV) Candidate by Deleting the Viral NS1 and NS2 Genes This example describes production of a recombinant RSV in which expression of two RSV genes, NS1 and NS2, has been ablated by removal of polynucleotide sequences encoding the NS1 and NS2 genes and their encoded proteins. As described earlier, NS1 or NS2 gene is dispensable for RSV replication in vitro. It is possible that deletion of two accessory genes from RSV will produce a recombinant RSV with alternative attenuation phenotype.

To delete the NS1 and NS2 gene from RSV, two restriction enzyme sites were inserted at positions of the gene start signal of NS1 and downstream of the gene end signal of NS2. A two step cloning procedure was performed to delete the entire NS1 and NS2 genes from RSV. A Pst I restriction enzyme site was introduced at position of 45 nt and at position of 1110 nt of RSV sequence by site-directed mutagenesis. Site-directed mutagenesis was performed in pET(X/A) cDNA subclone, which contained the first 2128 nucleotides of RSV sequence that encode the NS1, NS2 and part of the N gene of RSV. The 2128 nucleotide RSV cDNA fragment was cloned into the pET vector through the Xma I and Avr restriction sites. Digestion of pET(X/A) plasmid that contained the introduced two Pst I restriction enzyme sites removed a 1065-nt fragment that included the NS1 and NS2 genes. pET(X/S) plasmid containing NS1 and NS2 deletion was digested with Avr II and Sac I restriction enzymes and the remaining 1063 nucleotide RSV cDNA fragment was then cloned into a full length RSV antigenomic cDNA clone. The resulting plasmid that contained deletion of both NS1 and NS2 was designated pA2ΔNS1ΔNS2. Deletion of NS1 and NS2 in pA2ΔNS1ΔNS2 plasmid was confirmed by restriction enzyme mapping.

Recovery of infectious RSV that contained both NS1 and NS2 deletion (rA2 ΔNS1ΔNS2) was performed as described earlier. Infectious virus with both NS1 and NS2 deleted was obtained from transfected Hep-2 cells. RT/PCR was performed to confirm that both NS1 and NS2 genes were deleted from rA2 ΔNS1ΔNS2 using a pair of primers flanking the NS1 and NS2 genes. Deletion of NS1 and NS2 from rA2ΔNS1ΔNS2 was further confirmed by Northern blot. As shown in FIG. 18, neither NS1 nor NS2 mRNAs was detected in cells infected with rA2ΔNS1ΔNS2 using a riboprobe specific to the NS1 or NS2 gene. This indicated that expression of NS1 and NS2 was ablated from rA2ΔNS1ΔNS2. rA2ΔNS1ΔNS2 formed very small plaques in infected Hep-2 cells, but only slight plaque size reduction was seen in Vero cells (FIG. 19). The small plaque phenotype is commonly associated with attenuating mutations.

A growth kinetics study of rA2ΔNS1ΔNS2 in comparison with rA2 was performed in Vero cells. Cells grown in 6-cm dishes were infected with rA2 or rA2ΔNS1ΔNS2 at a moi of 0.2. As seen in FIG. 25, rA2ΔNS1ΔNS2 exhibited slower growth kinetics and its peak titer was about 5-fold lower than that of rA2. To analyze virus replication in different host cells, each cell line grown in 6-well plates was infected with rA2ΔNS1ΔNS2 or rA2 at moi of 0.2. Three days postinfection, the culture supernatants were collected and virus was quantitated by plaque assay. rA2ΔNS1 ΔNS2 had only slight reduction in virus titer compared to rA2 in Vero cells. About 1.5 log reduction in virus titer was observed in Hep-2, MDBK and LLC-MK2 cells. More reduction in virus (about 3 log) was seen in Hela and MRC5 cells (Table 14). Replication of rA2 ΔNS1ΔNS2 in a small animal model is currently being investigated. Preliminary data indicated that rA2ΔNS1ΔNS2 is attenuated in cotton rats. As replication of rA2 ΔNS1ΔNS2 was not detected in cotton rats, it appears that the rA2ΔNS1ΔNS2 deletion mutant is very attenuated. The NS1 and NS2 deletion mutant therefore provides an alternative method for attenuating RSV.

TABLE 14

Growth comparison of rA2ΔNS1ΔNS2 and rA2 in different cell lines

| Cell lines | Virus titer [log$_{10}$ (pfu/ml)] | |
|---|---|---|
| | rA2 | rA2ΔNS1ΔNS2 |
| Vero | 6.4 | 6.2 |
| Hep-2 | 6.7 | 5.1 |
| MDBK | 6.7 | 5.2 |
| MRC-5 | 5.9 | 3.1 |
| Hela | 6.5 | 3.8 |
| LLC-MK2 | 6.7 | 5.1 |

11.9 Generation of a Human Respiratory Syncytial Virus Vaccine (RSV) Candidate by Deleting the Viral NS1 and SH Genes This example describes production of a recombinant RSV in which expression of two different RSV genes, NS1 and SH, has been ablated by removal of polynucleotide sequences encoding the NS1 and SH genes and their encoded proteins. As described earlier, NS1 or SH genes is dispensable for RSV replication in vitro. It is possible that deletion of two accessory genes from RSV will produce a recombinant RSV with increased attenuation phenotype.

NS1 and SH genes were deleted from the full-length RSV CDNA construct through cDNA cloning. A Xma I to Avr II fragment that contained NS1 deletion in pET(X/A) subclone was removed by digestion with Xma I and Avr II restriction enzymes and was cloned into the full-length RSV antigenomic CDNA clone that contained the SH gene deletion (pA2 SH). The resulting plasmid that contained deletion of both NS1 and SH was designated pA2ΔNS1ΔSH. Deletion of NS1 and SH in pA2ΔNS1ΔSH plasmid was confirmed by restriction enzyme mapping.

Recovery of infectious RSV that contained both NS1 and SH deletion (rA2ΔNS1ΔSH) was performed as described earlier. Infectious virus with both NS1 and SH deleted was obtained from transfected Hep-2 cells. Virus was plaque purified 3 times and amplified in Vero cells. Deletion of both the NS1 and SH genes in rA2ΔNS1ΔSH was confirmed by RT/PCR using two sets of primers that flanked the NS1 or SH gene, respectively. Northern blot of rA2ΔNS1ΔSH infected total cellular RNA was performed using a riboprobe specific to the NS 1 or SH gene. As shown in FIG. 23, expression of NS1 and SH mRNA was ablated in cells infected with rA2ΔNS1ΔSH.

Replication of rA2ΔNS 1ΔSH in vitro and in vivo is currently being studied. The fact that the rA2ΔNS1ΔSH virus can grow, albeit with reduced efficiency, indicates that the NS1 and SH genes are dispensable for RSV replication. This mutant will therefore likely serve as an additional potential recombinant RSV vaccine agent.

11.10 Generation of a Human Respiratory Syncytial Virus Vaccine (RSV) Candidate by Deleting the Viral NS2 and SH Genes This example describes production of a recombinant RSV in which expression of two different RSV genes, NS2 and SH, has been ablated by removal of polynucleotide sequences encoding the NS2 and SH genes and their encoded proteins. As described earlier, NS2 or SH gene is dispensable for RSV replication in vitro. It is possible that deletion of two accessory genes from RSV will produce a recombinant RSV with different attenuation phenotype.

NS2 and SH genes were deleted from the full-length RSV cDNA construct through cDNA cloning. A Xma I to Avr II fragment that contained NS2 deletion in pET(X/A) subclone was removed by digestion with Xma I and Avr II restriction enzymes and was cloned into the full-length RSV antigenomic cDNA clone that contained the SH gene deletion (pA2ΔSH). The resulting plasmid that contained deletion of both NS2 and SH was designated pA2ΔNS2ΔSH. Deletion of NS2 and SH in pA2ΔNS2ΔSH plasmid was confirmed by restriction enzyme mapping.

Recovery of infectious RSV that contained both NS2 and SH deletion (rA2ΔNS2ΔSH) was performed as described earlier. Infectious virus with both NS2 and SH deleted was obtained from transfected Hep-2 cells. Virus was plaque purified 3 times and amplified in Vero cells. Deletion of both NS2 and SH gene in rA2ΔNS2ΔSH was confirmed by RT/PCR using two sets of primers that flanked the NS2 or SH gene, respectively. Northern blot of rA2ΔNS2ΔSH infected total cellular RNA was performed using a riboprobe specific to the NS2 or SH gene. As shown in FIG. 23, expression of NS2 and SH mRNA was ablated in cells infected with rA2 ΔNS2ΔSH.

Replication of rA2ΔNS2ΔSH in vivo was determined in respiratory pathogen-free 4-week old cotton rats. Cotton rats in groups of 5 were inoculated intranasally under light methoxyflurane anesthesia with $10^5$ pfu per animal in a 0.1-ml inoculum of rA2 or rA2ΔNS2ΔSH. On day 4 postinoculation, animals were sacrificed by $CO_2$ asphyxiation and their nasal trubinates and lungs were obtained separately. Tissues were homogenized and virus titers were determined by plaque assay in Vero cells. As shown in Table 15, reduced virus replication was observed in the upper and lower respiratory tracts of cotton rats that were infected with rA2ΔNS2ΔSH. This indicated that deletion of the NS2 and SH genes attenuated RSV and this recombinant RSV with NS2 and SH deletion might serve as a good vaccine candidate for human use.

TABLE 15

Replication of rA2ΔNS2ΔSH and rA2 in cotton rats

| | Virus titer (mean $\log_{10}$ pfu/g tissue ± SE) | |
|---|---|---|
| Virus | Nasal turbinats | Lung |
| rA2 | 2.30 ± 0.26 | 4.23 ± 0.10 |
| rA2ΔNS2ΔSH | 1.11 ± 1.34 | 2.76 ± 0.06 |

[a]Groups of five cotton rats were immunized intranasally with $10^6$ pfu of the indicated virus on day 0. The level of infected virus replication at day 4 was determined by plaque assay on indicated specimens, and the mean $\log_{10}$ titer ± standard error (SE) per gram tissue were determined.

11.11 Generation of a Human Respiratory Syncytial Virus Vaccine (RSV) Candidate by Deleting the Viral NS1, NS2, and SH Genes This example describes production of a recombinant RSV in which expression of three RSV genes, NS1, NS2 and SH, has been ablated by removal of polynucleotide sequences encoding three RSV genes (NS1, NS2 and SH) and their encoded proteins. As described earlier, NS1, NS2 or SH alone is dispensable for RSV replication in vitro. It is possible that deletion of three accessory genes from RSV will produce a recombinant RSV with a different attenuation phenotype.

NS1, NS2 and SH genes were deleted from the full-length RSV cDNA construct through cDNA cloning. A Xma I to Avr II fragment that contained NS1 and NS2 deletion in pET(X/A) subclone as described earlier was removed by digestion with Xma I and Avr II restriction enzymes and was cloned into the full-length RSV antigenomic cDNA clone that contained the SH gene deletion (pA2ΔSH). The resulting plasmid that contained deletion of three genes (NS1, NS2 and SH) was designated pA2ΔNS1 ΔNS2ΔSH. Deletion of NS1, NS2 and SH in pA2ΔNS1ΔNS2ΔSH plasmid was confirmed by restriction enzyme mapping.

Recovery of infectious RSV that contained three genes deletion (NS1, NS2 and SH), rA2ΔNS1ΔNS2ΔSH, was performed as described earlier. Infectious virus was obtained from transfected Hep-2 cells. Virus was plaque purified 3 times and amplified in Vero cells. Deletion of NS1, NS2 and SH genes in rA2ΔNS1ΔNS2ΔSH was confirmed by RT/PCR using two sets of primers that flanked the NS 1 and NS2 genes or the SH gene, respectively. Northern blot of infected total cellular RNA of rA2ΔNS1ΔNS2ΔSH was performed using a riboprobe specific to the NS1, NS2 or SH gene. As shown in FIG. 23, expression of NS1, NS2 and SH mRNA was ablated in cells infected with rA2ΔNS 1ΔNS2ΔSH. This indicated that these three genes were indeed deleted from RSV.

Replication of rA2ΔNS1ΔNS2ΔSH in vivo was determined in respiratory pathogen-free 4-week old cotton rats. Cotton rats in groups of 5 were inoculated intranasally under light methoxyflurane anesthesia with $10^5$ pfu per animal in a 0.1-ml inoculum of rA2 or rA2ΔNS1ΔNS2ΔSH. On day 4 postinoculation, animals were sacrificed by $CO_2$ asphyxiation and their nasal turbinates and lungs were obtained separately. Tissues were homogenized and virus titers were determined by plaque assay in Vero cells. As shown in Table 16, no virus replication was observed in the upper and lower respiratory tracts of cotton rats that were infected with rA2ΔNS1ΔNS2ΔSH. This indicated that deletion of the NS2 and SH genes attenuated RSV and this recombinant RSV with NS2 and M2-2 deletion might serve as a good vaccine candidate for human use.

TABLE 16

Replication of rA2ΔNS1ΔNS2ΔSH and rA2 in cotton rats

| Virus | Virus titer (mean $\log_{10}$ pfu/g tissue ± SE) | |
|---|---|---|
| | Nasal turbinates | Lung |
| rA2 | 2.30 ± 0.26 | 4.23 ± 0.10 |
| rA2ΔNS1ΔNS2ΔSH | <1.4 | <1.4 |

[a]Groups of five cotton rats were immunized intranasally with $10^5$ pfu of the indicated virus on day 0. The level of infected virus replication at day 4 was determined by plaque assay on indicated specimens, and the mean $\log_{10}$ titer ± standard error (SE) per gram tissue were determined.

In conclusion, 11 different gene deletion mutants have been obtained as sunmarized in Table 17. Four RSV accessory genes have been deleted either individually or in combination. These different deletion mutants showed different plaque formation and growth properties. A good correlation was demonstrated between plaque size in vitro and attenuation in vivo. These different RSV deletion mutants provide several choices for use as potential RSV vaccine candidates.

TABLE 17

Summary of RSV gene deletion mutants

| Virus | Recovered |
|---|---|
| ΔM2-2 | Yes |
| ΔSH | Yes |
| ΔNS1 | Yes |
| ΔNS2 | Yes |
| ΔM2-2ΔSH | Yes |
| ΔM2-2ΔNS1 | ND[a] |
| ΔM2-2ΔNS2 | Yes |
| ΔNS1ΔNS2 | Yes |
| ΔSHΔNS1 | Yes |
| ΔSHΔNS2 | Yes |
| ΔSHΔNS1ΔNS2 | Yes |

[a]ND Not determined. Replication of rA2ΔM2-2ΔNS1 was not detected in tissue culture.

12. EXAMPLE

Generation of an Attenuated Human Respiratory Syncytial Virus Vaccine (RSV) Candidate by Mutagenesis of the Viral M2-1 Gene Rationale:

The ability to generate infectious RSV from cDNA allows defined changes to be introduced into the RSV genome. The phenotype of the rescued viruses can be directly attributed to the engineered changes in the genome. Changes in the virus genome can be easily verified by sequencing the region in which mutations are introduced. Different point mutations and lesions can be combined in a single virus to create suitably attenuated and genetically stable RSV vaccine candidates. The RSV genome encodes several auxiliary proteins: NS1, NS2, SH, M2-1 and M2-2 proteins that do not have counterparts in other paramyxoviruses. The function of these genes in the viral life cycle is the subject of ongoing investigations.

The product of the M2-1 gene is a 22 kDa protein which has been shown to promote processive sequential transcription and antitermination of transcription at each gene junction of the RSV genome in vitro (Collins, P. L. et al.*Proc. Natl. Acad Sci. USA* 93, 81–85 (1996); Hardy, R. W. et al. *J. Virol.* 72, 520–526 (1998)). M2-1 is also thought to be a structural component of the viral nucleocapsid and interaction of M2-1 with the N protein has been observed in RSV infected cells (Garcia et al. *Virology* 195:243–247 (1993)). The M2-1 protein contains a putative zinc binding motif (Cys3His motif) at its N-terminus (Worthington et al., 1996, Proc. Natl. Acad. Sci. 93:13754–13759). This motif is highly conserved throughout the pneumovirus genus.

Two mutagenesis strategies are presented here to introduce mutations in the M2-1 protein. The first method involves changing each of the cysteine residues individually to glycine (cysteine scanning mutagenesis). The second method involves engineering premature stop codons at the carboxyl terminus of the protein to produce truncated M2-1 proteins of various length. These strategies provide different approaches to making attenuated RSV for use as live vaccines.

12.1 Cysteine Scanning Mutagenesis of M2-1

Four cysteine residues are present in the M2-1 protein at amino acid positions 7, 15, 21 and 96. Cys7, Cys15 and Cys21 lie in the putative zinc binding motif, the Cys3His motif. DNA oligonucleotides were designed to change these cysteine codons to that for glycine by Quickchange site-directed mutagenesis (Stratagene). Mutagenesis was performed using a cDNA subclone (pET-S/B) that contained nucleotide 4482 to nucleotide 8505 of the RSV genome. The oligonucleotides corresponding to the positive sense of the RSV genome used for the mutagenesis reactions are listed in Table 18.

The engineered changes in the pET-S/B RSV subclone were verified by DNA sequence analysis. Each Sac I to Bam HI restriction fragment that contained the mutated cysteine codon in M2-1 was individually cloned into an infectious RSV antigenomic cDNA clone that was derived from RSV strain A2 (Jin, H. et al. *Virology* 251, 206–214 (1998)). The full-length RSV antigenomic cDNA clone with an engineered cysteine to glycine codon change was designated pA2MC1, 2, 3, or 4.

TABLE 18

Primers used for changing each cysteine codon in the M2-1 gene[a]

| Primer | Position in RSV antigenome | Sequence |
|---|---|---|
| MC1 | nt 7609–7641 | 5'TCACGAAGGAATCCTGGCAAATTTGAAATTCGA (SEQ ID NO:50) |
| MC2 | nt 7633–7665 | 5'GAAATTCGAGGTCATGGTTTAAATGGTAAGAGG (SEQ ID NO:51) |
| MC3 | nt 7648–7683 | 5'TGC TTA AAT GGT AAG AGG TGT CAT TTT AGT CAT AAT (SEQ ID NO:52) |
| MC4 | nt 7876–7908 | 5'ACTAAACAATCAGCAGGTGTTGCCATGAGCAAA (SEQ ID NO:53) |

[a]The numbers correspond to nucleotides in the RSV antigenome. Nucleotides that were mutated to change cysteine codons to glycine codons are in bold and underlined.

To produce infectious RSV that contained an individual cysteine mutation in M2-1, pA2MC1, 2, 3, or 4 was transfected into cells that expressed the T7 RNA polymerase together with plasmids that expressed the N, P and L protein. Briefly, monolayers of Hep-2 cells in 6 well dishes at a confluency of 70–80% were infected with modified vaccinia virus that expressed the T7 RNA polymerase (MVA) at a moi of 5. Absorption of MVA was performed at room temperature for 1 hour. The infected cells were washed with OPTI-MEM (Life Technologies) and transfected with pA2MC1, pA2MC2, pA2MC3 or pA2MC4 antigenomic plasmids together with a mixture of plasmids encoding the RSV N, P and L proteins each under the control of the 17 promoter. The amount of plasmids used for each transfection are: 0.5 μg antigenome plasmid, 0.4 μg N plasmid, 0.4 μg P plasmid and 0.2 μg L plasmid in a final volume of 0.1 ml OPTI-MEM. The final plasmid mixture was combined with 0.1 ml OPTI-MEM containing 10 μl lipofecTACE (Life Technologies). After 15 minutes incubation at room temperature, the transfection mixture was added to the MVA infected cells. The transfection reaction was incubation at 33° C. for 5 hours. After 5 hours, the transfection medium was removed and replaced with MEM supplemented with 2% fetal bovine serum and incubated at 33° C. for 3 days. Following the 3-day incubation, medium was harvested and passaged in Vero cells for 6 days. Positive immunostaining of the infected cell monolayers using goat anti-RSV antibody (Biogenesis) was then used to identify wells containing successfully rescued viruses. RT/PCR of genomic viral RNA was performed to verify that the engineered changes were present in the rescued viruses. A recombinant RSV bearing the introduced cysteine change at position of 96, rA2C4 was obtained. Replication in vitro and in an animal model of rA2C4 is currently being studied. Preliminary results indicated that rA2C4 showed reduced plaque size at 35° C. and is therefore probably attenuated. Preliminary results indicated that rA2C4 has about a 10-fold reduction in replication of the lungs of cotton rats (See Table 19). Recovery of rA2C1, rA2C2 and rA2C3 are currently being pursued. It is quite possible that changes in any of the three cysteine residues in the putative zinc binding motif may prove to be lethal to the M2-1 protein.

TABLE 19

Replication of M2-1 mutants in cotton rats

| Virus | Virus titer (mean $\log_{10}$ pfu/g tissue ± SE) Lung |
|---|---|
| rA2 | 3.55 ± 0.07 |
| RA2C4 | 2.29 ± 0.13 |
| rA2MSCH3 | 1.97 ± 0.18 |

[a]Groups of five cotton rats were immunized intranasally with $10^5$ pfu of the indicated virus on day 0. The level of infected virus replication at day 4 was determined by plaque assay on the indicated specimens, and the mean $\log_{10}$ titer ± standard error (SE) per gram tissue was determined.

12.2 C-Terminal Truncations of the M2-1 Protein

Tandem termination codons were introduced at the C-terminus of the M2-1 protein by site-directed mutagenesis in order to create progressively longer truncations from the C-terminal end of the M2-1 protein. Mutagenesis was performed using a cDNA subclone (pET-S/B) that contained RSV sequences from nucleotide 4482 to nucleotide 8505. Oligonucleotides corresponding to the positive sense of the RSV genome that were used for creating premature tandem termination codons in M2-1 are listed in Table 20.

The engineered changes were verified by sequence analysis of the RSV subclone containing the introduced mutations. The Sac I to Bam HI restriction fragment containing the premature tandem termination codons in M2-1 was excised from RSV subclone pET-S/B and introduced into the full length infectious RSV antigenomic cDNA clone (Jin et al.,1998). Each reassembled full-length RSV antigenomic CDNA containing the engineered premature tandem termination codons along with a unique Hind III site was designated pA2MCSCH1, pA2MSCH 2 or pA2MSCH3.

TABLE 20

Primers used to introduce tandem termination codons in the C-terminus of the M2-1 protein

| Primer | Position in RSV antigenome | Sequence[a] |
|---|---|---|
| MSCH 1 | nt 7960–8011 | 5'GAGCTAAATTCACCCAAGATA*AGCTT*GTAATAA ACTGTCATATCATATATTG (SEQ ID NO:54) |

TABLE 20-continued

Primers used to introduce tandem termination codons in the C-terminus of the M2-1 protein

| Primer | Position in RSV antigenome | Sequence[a] |
|---|---|---|
| MSCH2 | nt 8035–8076 | 5'CAAACTATCCATCTGTAATAAA*GCTT*GCCAGCAGACGTATTG (SEQ ID NO:55) |
| MSCH3 | nt 8120–8169 | 5'CCATCAACAACCCAAAATAATAAA*GCTT*TAGTGATACAAATGACCATGCC (SEQ ID NO:56) |

[a]The numbers correspond to nucleotides in the RSV antigenome. Tandem stop codons are indicated in bold. Mutated nucleotides are underlined and unique Hind III sites introduced simultaneously with the tandem stop codon are shown in italics.

Recombinant RSV that contained deletion in the C-terminal of the M2-1 protein was generated by transfection of pA2MCSCH1, pA2MSCH2 or pA2MSCH3 together with plasmids expressing the N, P and L proteins as described above. Recovery of infectious RSV that contained the shortest deletion in the C-terminus of the M2-1 protein, derived from pA2MSCH3 has been obtained. This virus had a 17 amino acid truncation at the C-terminus of M2-1 because of the engineered two tandem stop codons at amino acid 178 and 179. Virus plaque purification, amplification and verification of the engineered tandem termination codons in rA2MSCH3 are currently being performed. The rescue of recombinant RSV containing longer deletions in the C-terminus of the M2-1 protein is also being pursued. Preliminary results indicate that rA2MSCH3 has about a 15-fold reduction in replication of the lungs of cotton rats (See Table 19). Viable M2-1 deletion mutants provide an alternative method to attenuating RSV by itself or in combination with other mutations in the RSV genome for vaccine use.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Various publications are cited herein, the disclosures of which are incorporated herein by reference in their entireties.

What is claimed is:

1. An isolated live-attenuated respiratory syncytial virus particle which comprises a respiratory syncitial virus antigenome or genome containing a C-terminal truncation of the M2-1 protein, wherein the virus exhibits a lower degree of virulence as compared to a wild type RSV, and wherein the truncation is less than 46 amino acids in length.

2. The isolated live-attenuated respiratory syncytial virus particle of claim 1, wherein a stop codon causing said C-terminal truncation is at a position selected from a group consisting of nucleotide position 8053–8055, 8137–8139, and 8140–8142.

3. The virus particle of claim 2, wherein the stop codon causing said C-terminal trunication is at nucleotide position 8137–8139.

4. An isolated live-attenuated respiratory syncytial virus particle which comprises a respiratory syncytial virus antigenome or genome containing at least one M2-1 gene mutation, wherein (i) one M2-1 gene mutation encodes an amino acid exchange from a cysteine to an amino acid selected from a group consisting of glycine, valine, aspartic acid, and alanine at amino acid position 96, (ii) wherein cysteine residues at positions 7, 15, and 21 are retained, and (iii) wherein the virus exhibits a lower degree of virulence as compared to a wild type RSV.

5. An isolated live-attenuated respiratory syncytial virus particle which comprises a respiratory syncytial virus antigenome or genome comprising an M2-1 gene mutation at amino acid position 96, wherein the virus exhibits a lower degree of virulence as compared to a wild type RSV, and wherein the Cys3His motif at the N-terminus of the M2-1 protein is maintained.

6. The isolated live-attenuated respiratory virus particle of claim 5, wherein the M2-1 gene mutation at amino acid position 96 encodes an amino acid exchange from a cysteine to an amino acid selected from a group consisting of glycine, valine, aspartic acid, and alanine.

7. The virus particle of claim 5, wherein the respiratory syncytial virus antigenome or genome further comprises a truncation of the M2-1 gene.

8. The virus particle of claim 6, wherein a stop codon causing said C-terminal truncation is at a position selected from a group consisting of nucleotide position 8053–8055, 8137–8139, and 8140–8142.

* * * * *

UNITED STATES PATENT AND TRADEMARK OFFICE
CERTIFICATE OF CORRECTION

PATENT NO. : 6,830,748 B1
DATED : December 14, 2004
INVENTOR(S) : Hong Jin et al.

It is certified that error appears in the above-identified patent and that said Letters Patent is hereby corrected as shown below:

Column 99,
Line 2, "syncitial" should read -- syncytial --.

Signed and Sealed this

Twenty-third Day of August, 2005

JON W. DUDAS
*Director of the United States Patent and Trademark Office*